(12) United States Patent
Desai et al.

(10) Patent No.: US 11,883,397 B2
(45) Date of Patent: Jan. 30, 2024

(54) SUBSTITUTED PYRIDO[1,2-A]PYRROLO[1,2-D]PYRAZINES FOR TREATING VIRAL INFECTIONS

(71) Applicant: Gilead Sciences, Inc., Foster City, CA (US)

(72) Inventors: Manoj C. Desai, Martinez, CA (US); Mingzhe Ji, Union City, CA (US); Haolun Jin, Foster City, CA (US); Hyung-Jung Pyun, Fremont, CA (US); Teresa Alejandra Trejo Martin, Belmont, CA (US)

(73) Assignee: Gilead Sciences, Inc., Foster City, CA (US)

( * ) Notice: Subject to any disclaimer, the term of this patent is extended or adjusted under 35 U.S.C. 154(b) by 32 days.

(21) Appl. No.: 17/532,148

(22) Filed: Nov. 22, 2021

(65) Prior Publication Data
US 2022/0233525 A1    Jul. 28, 2022

Related U.S. Application Data

(60) Continuation of application No. 16/572,159, filed on Sep. 16, 2019, now Pat. No. 11,213,523, which is a continuation of application No. 15/982,197, filed on May 17, 2018, now Pat. No. 10,456,395, which is a continuation of application No. 15/257,528, filed on Sep. 6, 2016, now abandoned, which is a division of application No. 14/329,697, filed on Jul. 11, 2014, now Pat. No. 9,458,159.

(60) Provisional application No. 61/845,807, filed on Jul. 12, 2013.

(51) Int. Cl.
| A61K 31/4985 | (2006.01) |
| C07D 487/22 | (2006.01) |
| C07D 471/18 | (2006.01) |
| C07D 471/14 | (2006.01) |

(52) U.S. Cl.
CPC ........ *A61K 31/4985* (2013.01); *C07D 471/14* (2013.01); *C07D 471/18* (2013.01)

(58) Field of Classification Search
CPC .......................... A61K 31/4985; C07D 487/22
USPC .......................................... 514/250; 544/343
See application file for complete search history.

(56) References Cited

U.S. PATENT DOCUMENTS

| 5,814,639 A | 9/1998 | Liotta et al. |
| 5,914,331 A | 6/1999 | Liotta et al. |
| 5,922,695 A | 7/1999 | Arimilli et al. |
| 5,935,946 A | 8/1999 | Munger, Jr. et al. |
| 5,977,089 A | 11/1999 | Arimilli et al. |
| 6,043,230 A | 3/2000 | Arimilli et al. |
| 6,620,841 B1 | 9/2003 | Fujishita et al. |
| 6,642,245 B1 | 11/2003 | Liotta et al. |
| 6,703,396 B1 | 3/2004 | Liotta et al. |
| 7,176,220 B2 | 2/2007 | Satoh et al. |
| 7,419,969 B2 | 9/2008 | Naidu et al. |
| 7,550,463 B2 | 6/2009 | Yoshida |
| 7,635,704 B2 | 12/2009 | Satoh et al. |
| 7,858,788 B2 | 12/2010 | Yoshida et al. |
| 8,129,385 B2 | 3/2012 | Johns et al. |
| 8,148,374 B2 | 4/2012 | Desai et al. |
| 8,188,271 B2 | 5/2012 | Yoshida et al. |
| 8,410,103 B2 | 4/2013 | Johns et al. |
| 8,592,397 B2 | 11/2013 | Dahl et al. |
| 8,633,219 B2 | 1/2014 | Matsuzaki et al. |
| 8,716,264 B2 | 5/2014 | Dahl et al. |
| 8,778,943 B2 | 7/2014 | Johns et al. |
| 8,981,103 B2 | 3/2015 | Ando et al. |
| 8,987,441 B2 | 3/2015 | Takahashi et al. |
| 9,051,337 B2 | 6/2015 | Johns et al. |
| 9,216,996 B2 | 12/2015 | Jin et al. |
| 2005/0054645 A1 | 3/2005 | Miyazaki et al. |
| 2005/0137224 A1 | 6/2005 | Shima et al. |
| 2007/0072831 A1 | 3/2007 | Cai et al. |
| 2007/0117848 A1 | 5/2007 | Puerta et al. |
| 2008/0020010 A1 | 1/2008 | Nair et al. |

(Continued)

FOREIGN PATENT DOCUMENTS

| DE | 2244012 A1 | 3/1973 |
| DE | 2552871 A1 | 7/1976 |

(Continued)

OTHER PUBLICATIONS

Advanced Organic Chemistry: Reactions, 15 Mechanisms, and Structure, 5th edition (Wiley, Dec. 2000)).

Agrawal, A. et al. (2012) "Probing Chelation Motifs in HIV Integrase Inhibitors" Proc. Natl. Acad. Sci. U.S.A. 109(7):2251-2256.

Agrawal, et al., Protocols for Oligonucleotide Conjugates, Eds, Humana Press; New Jersey, 1994; vol. 26 pp. 1-72.

(Continued)

*Primary Examiner* — Douglas M Willis

(57) ABSTRACT

Compounds for use in the treatment of human immunodeficiency virus (HIV) infection are disclosed. The compounds have the following Formula (I):

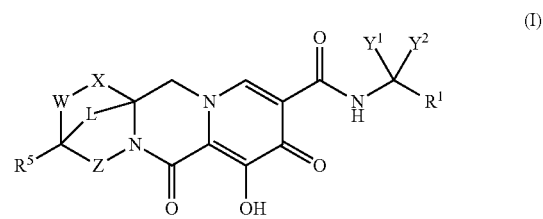

including stereoisomers and pharmaceutically acceptable salts thereof, wherein L, $R^1$, $R^5$, W, X, $Y^1$, $Y^2$, and Z are as defined herein. Methods associated with preparation and use of such compounds, as well as pharmaceutical compositions comprising such compounds, are also disclosed.

22 Claims, No Drawings

(56) References Cited

U.S. PATENT DOCUMENTS

| | | |
|---|---|---|
| 2008/0139579 A1 | 6/2008 | Morrissette et al. |
| 2008/0161271 A1 | 7/2008 | Yoshida et al. |
| 2008/0280945 A1 | 11/2008 | Lohani et al. |
| 2009/0036684 A1 | 2/2009 | Matsuda et al. |
| 2009/0143356 A1 | 6/2009 | Yoshida et al. |
| 2009/0253677 A1 | 10/2009 | Beaulieu et al. |
| 2009/0318702 A1 | 12/2009 | Matsuda et al. |
| 2010/0068695 A1 | 3/2010 | Kiyama et al. |
| 2012/0022251 A1 | 1/2012 | Sumino et al. |
| 2012/0108564 A1 | 5/2012 | Miyazaki et al. |
| 2012/0232117 A1 | 9/2012 | Bae et al. |
| 2013/0165489 A1 | 6/2013 | Cocklin et al. |
| 2014/0011995 A1 | 1/2014 | Sumino et al. |
| 2014/0094605 A1 | 4/2014 | Yoshida et al. |
| 2014/0221355 A1 | 8/2014 | Lazerwith et al. |
| 2014/0221356 A1 | 8/2014 | Jin et al. |
| 2014/0221378 A1 | 8/2014 | Myazaki et al. |
| 2014/0243521 A1 | 8/2014 | Yoshida et al. |
| 2014/0256937 A1 | 9/2014 | Akiyama |
| 2015/0232479 A1 | 8/2015 | Johns et al. |

FOREIGN PATENT DOCUMENTS

| | | |
|---|---|---|
| DE | 2658401 A1 | 7/1978 |
| EP | 0154199 A2 | 9/1985 |
| EP | 0378067 A2 | 7/1990 |
| EP | 0456073 A2 | 11/1991 |
| EP | 1544199 A1 | 6/2005 |
| EP | 1874117 A1 | 1/2008 |
| EP | 2412709 A1 | 2/2012 |
| EP | 1422218 B1 | 3/2012 |
| EP | 2465580 A1 | 6/2012 |
| EP | 2527007 A1 | 11/2012 |
| EP | 2602260 A1 | 6/2013 |
| GB | 2345058 A | 6/2000 |
| WO | WO-94/17090 A1 | 8/1994 |
| WO | WO-1999/005142 A1 | 2/1999 |
| WO | WO-1999/025345 A1 | 5/1999 |
| WO | WO-2000/027823 A1 | 5/2000 |
| WO | WO-2003/030897 A1 | 4/2003 |
| WO | WO-03035077 A1 | 5/2003 |
| WO | WO-2004004657 A2 | 1/2004 |
| WO | WO-2004024078 A2 | 3/2004 |
| WO | WO-2005016927 A1 | 2/2005 |
| WO | WO-2005/042533 A2 | 5/2005 |
| WO | WO-2005074513 A2 | 8/2005 |
| WO | WO-2005/110399 A2 | 11/2005 |
| WO | WO-2005110414 A2 | 11/2005 |
| WO | WO-2005112930 A1 | 12/2005 |
| WO | WO-2005113508 A1 | 12/2005 |
| WO | WO-2005113509 A1 | 12/2005 |
| WO | WO-2006/028523 A2 | 3/2006 |
| WO | WO-2006030807 A1 | 3/2006 |
| WO | WO-2006066414 A1 | 6/2006 |
| WO | WO-2006088173 A1 | 8/2006 |
| WO | WO-2006116764 A1 | 11/2006 |
| WO | WO-2007/014352 A2 | 2/2007 |
| WO | WO-2007049675 A1 | 5/2007 |
| WO | WO-2007079260 A1 | 7/2007 |
| WO | WO-2007/089030 A1 | 8/2007 |
| WO | WO-2007/092681 A2 | 8/2007 |
| WO | WO-2007/102512 A1 | 9/2007 |
| WO | WO-2007102499 A1 | 9/2007 |
| WO | WO-2008002959 A2 | 1/2008 |
| WO | WO-2008/033836 A2 | 3/2008 |
| WO | WO-2008048538 A1 | 4/2008 |
| WO | WO-2009/006199 A1 | 1/2009 |
| WO | WO-2009/006203 A1 | 1/2009 |
| WO | WO-2009/018320 A1 | 2/2009 |
| WO | WO-2009/018350 A1 | 2/2009 |
| WO | WO-2009/036161 A1 | 3/2009 |
| WO | WO-2009062285 A1 | 5/2009 |
| WO | WO-2009/103950 A1 | 8/2009 |
| WO | WO-2010/011813 A1 | 1/2010 |
| WO | WO-2010011812 A1 | 1/2010 |
| WO | WO-2010011814 A1 | 1/2010 |
| WO | WO-2010011815 A1 | 1/2010 |
| WO | WO-2010011816 A1 | 1/2010 |
| WO | WO-2010011818 A1 | 1/2010 |
| WO | WO-2010011819 A1 | 1/2010 |
| WO | WO-2010/068262 A1 | 6/2010 |
| WO | WO-2010068253 A1 | 6/2010 |
| WO | WO-2010/110231 A1 | 9/2010 |
| WO | WO-2010/110409 A1 | 9/2010 |
| WO | WO-2010130034 A1 | 11/2010 |
| WO | WO-2010147068 A1 | 12/2010 |
| WO | WO-2011094150 A1 | 8/2011 |
| WO | WO-2011105590 A1 | 9/2011 |
| WO | WO-2011119566 A1 | 9/2011 |
| WO | WO-2012/009009 A2 | 1/2012 |
| WO | WO-2012003497 A1 | 1/2012 |
| WO | WO-2012003498 A1 | 1/2012 |
| WO | WO-2012018065 A1 | 2/2012 |
| WO | WO-2012/039414 A1 | 3/2012 |
| WO | WO-2012/106534 A2 | 8/2012 |
| WO | WO-2012-145728 A1 | 10/2012 |
| WO | WO-2012/151361 A1 | 11/2012 |
| WO | WO-2012/151567 A1 | 11/2012 |
| WO | WO-2013/006738 A1 | 1/2013 |
| WO | WO-2013/006792 A1 | 1/2013 |
| WO | WO-2013/038407 A1 | 3/2013 |
| WO | WO-2013054862 A1 | 4/2013 |
| WO | WO-2013/087581 A1 | 6/2013 |
| WO | WO-2013/159064 A1 | 10/2013 |
| WO | WO-2014/011769 A1 | 1/2014 |
| WO | WO-2014/018449 A1 | 1/2014 |
| WO | WO-2014008636 A1 | 1/2014 |
| WO | WO-2014014933 A1 | 1/2014 |
| WO | WO-2014/022707 A1 | 2/2014 |
| WO | WO-2014/074675 A1 | 5/2014 |
| WO | WO-2014/093941 A1 | 6/2014 |
| WO | WO-2014/100077 A1 | 6/2014 |
| WO | WO-2014099586 A1 | 6/2014 |
| WO | WO-2014100323 A1 | 6/2014 |
| WO | WO-2014/104279 A1 | 7/2014 |
| WO | WO-2014200880 A1 | 12/2014 |
| WO | WO-2015006731 A1 | 1/2015 |
| WO | WO-2015006733 A1 | 1/2015 |
| WO | WO-2015039348 A1 | 3/2015 |
| WO | WO-2015048363 A1 | 4/2015 |
| WO | WO-2015/095258 A1 | 6/2015 |
| WO | WO-2015089847 A1 | 6/2015 |
| WO | WO-2015/110897 A2 | 7/2015 |

OTHER PUBLICATIONS

AIDS Info (2013) "AIDSinfo Guidelines for the Use of Antiretroviral Agents in HIV-1-Infected Adults and Adolescents" [downloaded from http://aidsinfo.nih.gov/guidelines on Mar. 15, 2013], 267 pages.

Akiyama, T. et al. (2013) "Discovery of Novel HIV Integrase Inhibitors Part 2. Selection and Evaluation of an Azabicyclic Carbamoyl Pyridone as a Pre-Clinical Candidate" Poster, 245th American Chemical Society National Meeting and Exposition; Apr. 7-11; New Orleans, LA.

Andrews, C. et al. (2014) "Long-Acting Integrase Inhibitor Protects Macaques from Intrarectal Simian/Human Immunodeficiency Virus" Science 343:1151-1154.

Angelov, P. et al. (2012) "Biomimetic synthesis, antibacterial activity and structure-activity properties of the pyroglutamate core of oxazolomycin" Org. Biomol. Chem. 10(17):3472-3485.

Aoki, Y. et al. (2015) "Dioxanone-Fused Dienes Enable Highly Endo-Selective Intramolecular Diels-Alder Reactions" Org. Lett. 17(11):2756-2759.

Barrow, J.C. et al. (2000) "Preparation and Evaluation of 1,3-Diaminocyclopentane-Linked Dihydropyrimidinone Derivatives as Selective alpha1a-Receptor Antagonists" Bioorganic & Medicinal Chemistry Letters 10(17):1917-1920.

Bisel, P. et al. (1998) "Diastereoselective .alpha.-iminoamine rearrangement: asymmetric synthesis of (R)-(-)-and (S)-(-)-2-benzyl-2-hydroxycyclohexanone" Tetrahedron: Asymmetry 9:4027-4034.

Brehm, W.J. et al. (1954) "The Relative Acidifying Influence of Oxygen and Sulfur Atoms on ?-Hydrogen Atoms" 76:5389-5391.

(56) References Cited

OTHER PUBLICATIONS

Brinson, C. et al. (2013) "Dolutegravir Treatment Response and Safety by Key Subgroups in Treatment Naive HIV Infected Individuals" Poster, 20th Conference on Retroviruses and Opportunistic Infections; Mar. 3-6; Atlanta, GA.
Brocklehurst, C.E. et al. (2011) "Diastereoisomeric Salt Formation and Enzyme-Catalyzed Kinetic Resolution as Complementary Methods for the Chiral Separation of cis-/ trans—Enantiomers of 3-Aminocyclohexanol" Organic Process Research and Development 15(1):294- 300.
Cahn, P. et al. (2013) "Dolutegravir (DTG) is Superior to Raltegravir (RAL) in ART-Experienced, Integrase-Naive Subjects: Week 48 Results From Sailing (ING111762)" Presentation, 7th IAS Conference on HIV Pathogenesis, Treatment and Prevention; Jun. 30-Jul. 3; Kuala Lumpur, Malaysia.
Canducci, F. et al. (2013) "In vitro phenotypes to elvitegravir and dolutegravir in primary macrophages and lymphocytes of clonal recombinant viral variants selected in patients failing raltegravir" J Antimicrob Chemother. 68(11):2525-2532.
Castagna, A. et al. (2014) "Dolutegravir in Antiretroviral-Experienced Patients With Raltegravir-and/or Elvitegravir-Resistant HIV-1: 24-Week Results of the Phase III VIKING-3 Study" Journal of Infectious Diseases 210:354-362.
Castellino, S. et al. (2013) "Metabolism, Excretion, and Mass Balance of the HIV-1 Integrase Inhibitor Dolutegravir in Humans" Antimicrobial Agents and Chemother. 57:3536-3546.
Chen, D-L. et al. (2003) "New C19-diterpenoid alkaloids from the roots of Aconitum transsecutum" Huaxue Xuebao 61(6):901-906 (Abstract).
Chen, S. et al. (2014) "Evaluation of the effect of UGT1A1 polymorphisms on dolutegravir pharmacokinetics" Pharmacogenomics 15(1):9-16.
Chorell, E et al. (2012) "Design and Synthesis of Fluorescent Pilicides and Curlicides: Bioactive Tools to Study Bacterial Virulence Mechanisms" Chem. Eur. J. 18(15):4522-4532.
Clotet, G. et al. (2014) "Once-daily dolutegravir versus darunavir plus ritonavir in antiretroviral-naive adults with HIV-1 infection (FLAMINGO) 48 week results from the randomised open-label phase 3b study" Lancet 383:2222-2231.
Cohen, J. et al. (2014) "A Bid to Thwart HIV With Shot of Long-Lasting Drug" Science 343:1067.
Cottrell, M. et al. (2013) "Clinical Pharmacokinetic, Pharmacodynamic and Drug-Interaction Profile of the Integrase Inhibitor Dolutegravir" Clin Pharmacokinet 52:981-994.
Culp, A. et al. (2014) "Metabolism, Excretion, and Mass Balance of the HIV Integrase Inhibitor, Cabotegravir (GSK1265744) in Humans" Presentation H-1010, 54th Intersience Conference on Antimicrobial Agents and Chemotherapy; Sep. 5-9; Washington, DC.
Curtis, L. et al. (2013) "Once-Daily Dolutegravir (DTG; GSK1349572) Has a Renal Safety Profile Comparable to Raltegravir (RAL) and Efavirenz in Antiretroviral (ART)-Naive Adults: 48 Week Results From SPRING-2 (ING113086) and Single (ING114467)" Poster No. CUPE 282, 7th IAS Conference on HIV Pathogenesis, Treatment and Prevention; Jun. 30-Jul. 3; Kuala Lumpur, Malaysia.
Dauvergne, J. et al. (2004) "Synthesis of 4-azacyclopent-2-enones and 5,5-dialkyl-4-azacyclopent-2-enones" Tetrahedron 60(11):2559-2567.
Deanda, F. et al. (2013) "Dolutegravir Interactions with HIV-1 Integrase-DNA: Structural Rationale for Drug Resistance and Dissociation Kinetics" Plos One 8(10):e77448.
Disclosed Anonymously (2014) "Preparation of Methyl 3-(benzyloxy)-5-992,4-difluorobenzyl)carbamoyl)-1-(2,2-dimethoxy ethyl)-4-oxo1,4-dihydropyridine-2-carboxylate" IP.com Prior Art Database Technical Disclosure, the whole document.
Disclosed Anonymously (2014) "Process for the Preparation of 4H-PYRAN-4-ONE Derivatives" IP.com Prior Art Database Technical Disclosure, the whole document.
DTG Clinical Data Summary (2013) Presentation of Posters; Raffi, F. et al. (#TULBPE17), Curtis, L.D et al. (#TUPE282), Nichols, G. et al. (#TULBPE19), IAS Kuala Lumpur, Jul. (Spring 2), 18 slides.

Enright, B. et al. (2010) "Assessment of Hydroxypropyl Methylcellulose, Propylene Glycol, Polysorbate 80, and Hydroxypropyl-beta-Cyclodextrin for Use in Developmental and Reproductive Toxicology Studies" Birth Defects Research (Part B)89:504-516.
European Search Report dated Mar. 31, 2015 for EP application No. 13815937.1.
Examination Report dated Nov. 8, 2017 for Australian Appl. No. 2014286995.
Examination Report dated Apr. 4, 2019 for Australian Appl. No. 2018236701.
FDA DDI Guidance for Industry—Drug Interaction Studies—Study Design, Data Analysis, Implications for Dosing, and Labeling Recommendations, 2012, 79 pages.
FDA DTG Pharmacology Review—Center For Drug Evaluation And Research; DTG PharmTox Review 2013, 103 pages.
Feinberg, J. et al. (2013) "Once-Daily Dolutegravir (DTG) is Superior to Darunavir/Ritonavir (DRV)/f) in Antiretroviral-Naive Adults: 48 Week Results from Flamingo (ING114915)" Presentation, 53rd ICAAC Interscience Conference on AntimicrobialAgents and Chemotherapy; Sep. 10-13; Denver, CO.
Final Office Action dated Jan. 19, 2018 for U.S. Appl. No. 15/257,528.
Gad, S. et al. (2006) "Nonclinical Vehicle Use in Studies by Multiple Routes in Multiple Species" International Journal of Toxicology 25:499-521.
Gao, Y. et al. (2007) "Attenuating Pregnane X Receptor (PXR Activiatin: A Molecular Modeling Approach" Xenobiotica 37(2):124-138.
Gein, V. L. et al. (1992) "Synthesis of 4-Substituted 1-Methyl-5-Aryl-and 1,5-Diaryltetrahydropyrrole-2,3-Diones and their Antiviral Action" translated from Khimik-farmatsevticheskii Zhurnal 25(12):37-40.
Gould, S. et al. (2005) "2-Hydroxypropyl-.beta.-cyclodextrin (HP-.beta.-CD): A toxicology review" Food and Chemical Toxicology 43:1451-1459.
Gouverneur, V. et al. (1998) "New Acylnitroso Compounds for the Asymmetric Oxyamination of Dienes" Tetrahedron 54:10537-10554.
Greene and Wuts, Protective Groups in Organic Synthesis, 3rd edition, John Wiley & Sons, New York (1999).
Grobler, J.A. et al. (2002) "Diketo Acid Inhibitor Mechanism and HIV-1 Integrase: Implications for Metal Binding in the Active Site of Phosphotransferase Enzymes" Proc. Natl. Acad. Sci. U.S.A. 99(10):6661-6666.
Grygorenko, O.O. et al. (2006) "Stereoselective synthesis of 2,4-methanoproline homologues" Tetrahedron: Asymmetry 17:252-258.
Gutierrez, M. et al. (2014) "Drug safety profile of integrase strand transfer inhibitors" Expert Opin. Drug Saf. 13(4):431-445.
Hackam, D.G. et al. (2006) "Translation of Research Evidence From Animals to Humans" JAMA 296(14):1731-1732.
Hare, S. et al. (2011) "Structural and Functional Analyses of the Second-Generation Integrase Strand Transfer Inhibitor Dolutegravir (S/GSK1349572)" Molecular Pharmacology 80(4):565-572.
Hightower, K. et al. (2011) "Dolutegravir (S/GKS1349572) Exhibits Siginifcantly Slower Dissociation than Raltegrvir and Elvitegravir from Wild-Type and Integrase Inhibitor-Resistant HIV-1 Integrase-DNA Complexes" Antimicrobial Agents and Chemotherapy 55(10):4552-4559.
Huang, W. et al. (2014) "Impact of Raltegravir/Elvitegravir Selected Mutationson Dolutegravir Cross-Resistance" Poster 595, 21st Conference on Retroviruses and Opportunistic Infection; Mar. 3-6; Boston, MA.
Hurt, C.B. et al. (2013) "Characterization of Resistance to Integrase Strand Transfer Inhibitors among Clinical Specimens in the United States, 2009-2012" Poster 591, 20th Conference on Retroviruses and Opportunistic Infections; Mar. 3-6; Atlanta, GA.
Hurt, C.B. et al. (2014) "Resistance to HIV Integrase Strand Transfer Inhibitors Among Clinical Specimens in the United States, 2009-2012" Clin Infect Dis. 58:423-431.
International Preliminary Report on Patentability dated Jun. 23, 2015 for PCT/US2013/076367.
Intl Search Report—Written Opinion dated Sep. 18, 2006 for PCT/US2006/016604.

(56) References Cited

OTHER PUBLICATIONS

Intl. Search Report—Written Opinion dated Feb. 9, 2016 for PCT/US2015/026017.
Intl. Search Report—Written Opinion dated Sep. 18, 2014 for PCT/US2014/046415.
Intl. Search Report dated Mar. 12, 2014 for PCT/US2013/076367.
Johns, B.A. et al. (2010) "The Discovery of S/GSK1349572: A Once Daily Next Generation Integrase Inhibitor with a Superior Resistance Profile" Presentation, 17th Conference on Retroviruses and Opportunistic Infections; Feb. 16-19; San Francisco, CA.
Johns, B.A. et al. (2013) "Carbamoyl Pyridone HIV?1 Integrase Inhibitors 3. A Diastereomeric Approach to Chiral Nonracemic Tricyclic Ring Systems and the Discovery of Dolutegravir (S/GSK1349572) and (S/GSK1265744)" J. Med. Chem. 56:5901-5916.
Johns, B.A. et al. (2013) "HIV Integrase Inhibitors" Successful Strategies for Discovery of Antiviral Drugs 32(6):149-188.
Jordan, V.C. (2003) "Tamoxifen: A Most Unlikely Pioneering Medicine" Nature Reviews: Drug Discovery 2:205-213.
Kawasuji, T. et al. (2007) "3-Hydroxy-1,5-dihydro-pyrrol-2-one Derivatives as Advanced Inhibitors of HIV Integrase" Bioorganic & Medicinal Chemistry 15:5487-5492.
Kawasuji, T. et al. (2012) "Carbamoyl Pyridone HIV-1 Integrase Inhibitors. 2. Bi-and Tricyclic Derivatives Result in Superior Antiviral and Pharmacokinetic Profiles" J. Med. Chem. 56:1124- 1135.
Kliewer, S. et al. (2002) "The Nuclear Pregnane X Receptor: A Key Regulator of Xenobiotic Metabolism" Endocrine Reviews 23(5):687-702.
Kobayashi, M. et al. (2011) "In Vitro Antiretroviral Properties of S/GSK1349572, a Next-Generation HIV Integrase Inhibitor" Antimicrob. Agents Chemother. 55(2):813-821.
Krow, G. et al. (2008) "Selectfluor as a Nucleofuge in the Reactions of Azabicyclo[n. 2.1]alkane beta.-Halocarbamic Acid Esters (n = 2,3)" J. Org. Chem. 73:2122-2129.
Lepist, E-I. et al. (2011) "Effect of Cobicistat and Ritonavir on Proximal Renal Tubular Cell Uptake and Efflux Tansporters" Poster A1-1724, 51st Interscience Conference on Antimicrobial Agents and Chemotherapy (ICAAC); Sep. 17-20; Chicago, IL.
Letendre, S. et al. (2013) "Distribution and Antiviral Activity in Cerebrospinal Fluid (CSF) of the Integrase Inhibitor, Dolutegravir (DTG): ING116070 Week 16 Results" Poster 178LB, 20th Conference on Retroviruses and Opportunistic Infections; Mar. 3-6; Atlanta, GA.
Llyod, J. et al. (2009) "Dihydropyrazolopyrimidines containing benzimidazoles as KV1.5 potassium channel antagonistics" Bioorganic & Medicinal Chemistry Letters 19(18):5469-5473.
Lou, Y. et al. (2013) "Meta-Analysis of Safety Data From 8 Clinical Studies With GSK1265744, an HIV Integrase Inhibitor, Dosed Orally or as Injection of Long-Acting Parenteral Nanosuspension (LAP)" Poster H-672, 53rd Interscience Conference onAntimicrobial Agents and Chemotherapy; Sep. 10-13; Denver, CO.
Maggi, P. et al. (2014) "The Problem of Renal Function Monitoring in Patients Treated With the Novel Antiretroviral Drugs" HIV Clin Trials 15(3):87-91.
Malet, I. et al. (2014) "New raltegravir resistance pathways induce broad cross-resistance to all currently used integrase inhibitors" J Antimicrob Chemother. 69:2118-2122.
Margolis, D.A. et al. (2014) "744 and Rilpivirine As Two Drug Oral Maintenance Therapy: LAI116482 (LATTE) Week 48 Results" Presentation, 21st Conference on Retroviruses and Opportunistic Infections; Mar. 3-6; Boston, MA.
Menendez-Arias, L. et al. (2014) "Antiretroviral therapy and drug resistance in human immunodeficiency virus type 2 infection" Antiviral Res. 102:70-86.
Metifiot, M. et al. (2013) "HIV Integrase Inhibitors: 20-Year Landmark and Challenges" Advances in Pharmacology 67:75-105.
Min, S. et al. (2010) "Pharmacokinetics and Safety of S/GSK1349572, a Next-Generation HIV Integrase Inhibitor, in Healthy Volunteers" Antimicrob Agents and Chemother 54(1):254-258.

Min, S. et al. (2011) "Antiviral activity, safety, and pharmacokinetics/pharmacodynamics of dolutegravir as 10-day monotherapy in HIV-1-infected adults" AIDS 25(14):1737-1745.
Mori, A. et al. (2001) "Regioselective Oxygenations of S-Trans Dienes, Silyl Dienol Ethers (SDEs), by Triphenyl Phosphite Ozonide (TPPO) and Its Mechanistic Study" J. Org. Chem. 66(10):3548-3553.
Mulvihill, M.J. et al. (1998) "Enzymatic Resolution of Aminocyclopentenols as Precursors to D-and Lcarbocyclic nucleosides" J. Org. Chem. 63(10):3357-3363.
Nair, V. et al. (2014) "Pharmacokinetics and Dose-Range Finding Toxicity of a Novel Anti-HIV Active Integrase Inhibitor" Antiviral Res. 108:5-29, Supplementary Materials.
Nichols, G. et al.(2013) "Phase 3 Assessment of Dolutegravir (DTG) 50 mg Twice Daily (BID) in HIV-1—Infected Subjects With Raltegravir (RAL) and/or Elvitegravir (EVG) Resistance in VIKING-3: Week 24 Results of All 183 Subjects Enrolled" PosterTULBPE19; 7.sup.th IAS Conference on HIV Pathogenesis, Treatment and Prevention Jun. 30-Jul. 3; Kuala Lumpur, Malaysia.
Nichols, G. et al. (2012) "Antiviral Activity of Dolutegravir in Subjects With Failure on an Integrase Inhibitor-Based Regimen: Week 24 Phase 3 Results From VIKING-3" Presentation O232, 11th International Congress on Drug Therapy in HIV Infection; Nov. 11-15; Glasgow, UK.
Nishioka, K. et al. (1992) "C-Labeling of a Tetrahydroacridine, a Novel CNS-Selective Cholinesterase Inhibitor" Journal of Labelled Compounds and Radiopharmaceuticals XXXI(7):553-560.
Non-Final Office Action dated Mar. 23, 2015 for U.S. Appl. No. 14/329,697.
Non-Final Office Action dated Sep. 11, 2017 for U.S. Appl. No. 15/257,528.
Notice of Opposition dated Jun. 20, 2017 for Colombian Appl. No. 15-265-717.
Office Action dated Mar. 30, 2015 for Pakistan Appl. No. 908/2013.
Office Action dated Aug. 16, 2016 for Canadian Appl. No. 2,918,055.
Office Action dated May 14, 2018 for Japanese Appl. No. 2016-525820.
Opposition Decision in European patent application No. 02749384.0, dated Mar. 12, 2015.
Pace, P. et al. (2007) "Dihydroxypyrimidine-4-carboxamides as Novel Potent and Selective HIV Integrase Inhibitors" J. Med. Chem. 50:2225-2239.
Palella, F.J., Jr. et al. (1998) "Declining Morbidity and Mortality Among Patients With Advanced Human Immunodeficiency virus Infection" N Engl. J Med 338(13):853-860.
Panel on 25 Antiretroviral Guidelines for Adults and Adolescents. Guidelines for the use of antiretroviral agents in HIV-1-infected adults and adolescents. Department of Health and Human Services. Available at http://aidsinfo.nih.gov/ContentFiles/AdultandAdolescentGL.pdf. Section accessed Mar. 14, 2013.
Park, B. et al. (2001) "Metabolism of Fluorine-Containing Drugs" Annu. Rev. Pharmacol. Toxicol. 41:443-470.
Patel, P. et al. (2011) "Pharmacokinetics of the HIV integrase inhibitor S/GSK1349572 co-administered with acid-reducing agents and multivitamins in healthy volunteers" J Antimicrob Chemother 66:1567-1572.
Patel, P. et al. (2014) "Relative Bioavailability of a Paediatric Granule Formulation of the HIV Integrase Inhibitor, Dolutegravir, in Healthy Adult Subjects" Antiviral Therapy 19(3):229-233.
PCT Application dated Dec. 19, 2013, [ --- pages].
Peng, C.S. et al. (2002) "Norditerpenoid alkaloids from the roots of Aconitum hemsleyanum Pritz. var. pengzhouense" Chinese Chemical Letters 13(3):233-236 (Abstract).
Petrocchi, A. et al. (2007) "From Dihydroxypyrimidine Carboxylic Acids to Carboxamide HIV-1 Integrase Inhibitors: SAR Around the Amide Moiety" Bioorg. Med. Chem. Lett. 17:350-353.
Pozniak, A. et al. (2013) "Dolutegravir (DTG) Versus Raltegravir (RAL) in ART-Experienced, Integrase-Naive Subjects: 24-Week Interim Results from Sailing (ING111762)" Poster 179LB, 20th Conference on Retroviruses and Opportunistic Infections; Mar. 3-6; Atlanta, GA.
PXR Background and data, 2 pages.

(56) References Cited

OTHER PUBLICATIONS

Quashie, P. et al. (2013) "Evolution of HIV integrase resistance mutations" Curr Opin Infect Dis 26:43-49.
Raffi, F. et al. (2012) "Once-daily Dolutegravir (DTG; S/GSK1349572) is Non-inferior to Raltegravir (RAL) in Antiretroviral-naive Adults. 48 Week Results from SPRING-2 (ING113086)" Presentation THLBB04; XIX International AIDS Conference; Jul. 22-27; Washington, DC.
Raffi, F. et al. (2013) "Dolutegravir is Non-Inferior to Raltegravir and Shows Durable Response Through 96 Weeks: Results From the SPRING-2 Trial" Poster TULBPE17; 7.sup.th IAS Conference on HIV Pathogenesis, Treatment and Prevention; Jun. 30-Jul.3; Kuala Lumpur, Malaysia.
Raffi, F. et al. (2013) "Once-daily dolutegravir versus raltegravir in antiretroviral-naive adults with HIV-1 infection: 48 week results from the randomised, double-blind, non-inferiority SPRING-2 study" Lancet 381:735-743.
Raffi, F. et al. (2013) "Once-daily dolutegravir versus twice-daily raltegravir in antiretroviral-naive adults with HIV-1 infection (SPRING-2; study): 96 week results from a randomised, double-blind, non-inferiority trial" Lancet Infect Dis 13:927-935.
Ragan, J.A. et al. (1995) "Studies of the Alkylation of Chiral, Non-Racemic, Tricyclic Pyrrolidinones" Heterocycles 41(1):57-70.
Reese, M.J. et al. (2013) "In Vitro Investigations into the Roles of Drug Transporters and Metabolizing Enzymes in the Disposition and Drug Interactions of Dolutegravir, a HIV Integrase Inhibitor" Drug Metab Dispos 41:353-361.
Remington: The Science and Practice of Pharmacy, 20th Edition (Philadelphia College of Pharmacy and Science, 2000).
Rhodes, M. et al. (2012) "Assessing a Theoretical Risk of Dolutegravir-Induced Developmental Immunotoxicity in Juvenile Rats" Toxicological Sciences 130(1):70-81.
Richman, D.D. (2001) "HIV chemotherapy" Nature 410:995-1001 (Abstract).
Saag, M.S. (2006) "Emtricitabine, a New Antiretroviral Agent with Activity against HIV and Hepatitis B Virus" Clin Infect Dis. 42:126-131.
Schenone, P. et al. (1990) "Reaction of 2-Dimethylaminomethylene-1,3-diones with Dinucleophiles. VIII. Synthesis of Ethyl and Methyl 2,4-Disubstituted 5-Pyrimidinecarboxylates" J. Heterocyclic Chem. 27(2):295-305.
SciFinder Journal (2013) "Bridged Oxazine Search" CAS Registry 248280-06-0, American Cancer Society:1-3.
Search Report dated Nov. 8, 2017 for European Appl. No. 17177428.4.
Song, I. et al. (2010) "Lack of Interaction Between the HIV Integrase Inhibitor S/GSK1349572 and Tenofovir in Healthy Subjects" J Acquir Immune Defic Syndr 55(3):365-367.
Song, I. et al. (2012) "Effect of Food on the Pharmacokinetics of the Integrase Inhibitor Dolutegravir" Antimicrob Agents and Chemother 56(3):1627-1629.
Song, I. et al. (2013) "Dolutegrvir Has No Effect on the Pharmacokinetics of Methadone or Oral Contraceptives With Norgestimate and Ethinyl Estradiol" Poster 535, 20th Conference on Retroviruses and Opportunistic Infections; Mar. 3-6; Atlanta, GA.
Song, I. et al. (2013) "Pharmacokinetics (PK) and PK.sub.—Pharmacodynamic (PD) Relationship of Dolutegravir (DTG) in Integrase Inhibitor (INI)-Naive Subjects" Poster A-1573, 53rd Interscience Conference on Antimicrobial Agents and Chemotherapy; Sep. 10-13; Denver, CO.
Soriano, V. et al. (2011) "Dolutegravir (GSK/ViiV Integrase) Treatment (with 50mg Once & Twice Daily) of HIV Subjects with Raltegravir Resistance & 3-Class ART Resistance: viral suppression at Week 24 in the VIKING Study" Presentation, EACS—European AIDS Conference; Oct.12-15; Belgrade, Serbia.
Spreen, W. et al. (2012) "Pharmacokinetics, Safety and Tolerability of the HIV Integrase Inhibitor S/GSK1265744 Long Acting Parenteral Nanosuspension Following Single Dose Administration to Healthy Adults" Presentation, 19th International AIDS Conference; Jul. 22-27; Washington, DC.
Spreen, W. et al. (2013) "First study of repeat dose co-administration of GSK1265744 and TMC278 long-acting parenteral nanosuspensions: pharmacokinetics, safety, and tolerability in healthy adults" Presentation, 7th IAS Conference on HIVPathogenesis, Treatment and Prevention; Jun. 30-Jul. 3; Kuala Lumpur, Malaysia.
Spreen, W. et al. (2013) "Pharmacokinetics, Safety, and Monotherapy Antiviral Activity of GSK1265744, an HIV Integrase Strand Transfer Inhibitor" HIV Clin Trials 14(5):192-203.
Springthorpe, B. et al. (2007) "From ATP to AZD6140: The Discovery of an Orally Active Reversible P2Y(12) Receptor Antagonist for the Prevention of Thrombosis" Biorganic & Medicinal Chemistry Letters 17(21):6013-6018.
Stellbrink, H. et al. (2013) "Dolutegravir in antiretroviral-naive adults with HIV-1: 96-week results from a randomized dose-ranging study" AIDS 27:1771-1778.
Summa, V. et al. (2006) "4,5-Dihydroxypyrimidine Carboxamides and N-Alkyl-5-hydroxypyrimidinone Carboxamides Are Potent, Selective HIV Integrase Inhibitors with Good Pharmacokinetic Profiles in Preclinical Species" J. Med. Chem. 49:6646-6649.
Summary of Product Characteristics—Annex I, Leaflet, EU—Triumeq, 62 pages [downloaded Sep. 8, 2014].
Taoda, Y. et al. (2013) "Discovery of Novel HIV Integrase Inhibitors Part 1. Molecular Design and SAR of Azabicyclic Carbamoyl Pyridone Inhibitors" Poster, 245th American Chemical Society National Meeting and Exposition; Apr. 7-11; New Orleans, LA.
Tchaparian, E. (2013) "Drug Transporters: An Overview of Their Role in Drug Interactions; Recommended Strategies to Assess Drug Transporters froma Regulatory and Industry Perspective" FDA Guidance Compliance Regulatory Information Guidances, 19 pages.
Thackaberry, E. et al. (2010) "Comprehensive Investigation of Hydroxypropyl Methylcellulose, Propylene Glycol, Polysorbate 80, and Hydroxypropyl-Beta-Cyclodextrin for use in General Toxicology Studies" Toxicological Sciences 117(2):485-492.
Thomas Reuters Drug News (2013) "Results from phase III trials of dolutegravir presented" [downloaded from http://drugnews.thomas-pharma.com/ddn/article.do? on Jul. 5, 2013], 1 page.
Thomas Reuters Drug News (2013) "Coadministration of long-acting GSK-744 and rilpivirine found feasible" [downloaded from http://drugnews.thomson-pharma.com/ddn/article.do?id=124544 on Jul. 8, 2013], 1 page.
Tivicay Highlights of Prescribing Information (Revised Sep. 2018).
Trinite, B. et al. (2013) "An HIV-1 Replication Pathway Utilizing Reverse Transcription Products That Fail To Integrate" Journal of Virology 87(23):12701-12720.
Triumeq Highlights of Prescribing Information (Revised Nov. 2017).
Tseng, A. et al. (2014) "Drug Interactions with Integrase Inhibitors" Pharm. D., 30 pages.
Van Lunzen, J. et al. (2012) "Once daily dolutegravir (S/GSK1349572) in combination therapy in antiretroviral-naive adults with HIV: planned interim 48 week results from SPRING-1, a dose-ranging, randomised, phase 2b trial" Lancet Infect Dis 12(2):111-118.
Wai, J.S. et al. (2007) "Dihydroxypyridopyrazine-1,6-dione HIV-1 Integrase Inhibitors" Bioorganic & Medicinal Chemistry Letters 17:5595-5599.
Walmsley, S. et al. (2012) "Dolutegravir (DTG; S/GSK1349572) + Abacavir/Lamivudine Once Daily Statistically Superior to Tenofovir/Emtricitabine/Efavirenz: 48-Week Results—Single (ING114467)" Presentation H-556b; 52nd Interscience Conference on Antimicrobial Agents and Chemotherapy; Sep. 9-12; San Francisco, CA.
Walmsley, S.L. et al. (2013) "Dolutegravir plus Abacavir-Lamivudine for the Treatment of HIV-1 Infection" N Engl J Med 369(19):1807-1818.
Wang, F-P. et al. (2005) "To seek an approach toward the chemical conversion of C19-diterpenoid alkaloids to taxoids" Tetrahedron 61(8):2149-2167 (Abstract).
Wang, F.P. et al. (1999) "Modifications of norditerpenoid alkaloids. I. N-deethylation reactions" Chinese Chemical Letters 10(5):375-378 (Abstract).
Wang, H. et al. (2015) "An Efficient and Highly Diastereoselective Synthesis of GSK1265744, a Potent HIV Integrase Inhibitor" Org. Lett. 17(3):564-567.

(56) References Cited

OTHER PUBLICATIONS

Wang, Y-C. et al. (2002) "Switch in asymmetric induction sense in cycloadditions using camphor-based nitroso dienophiles" Tetrahedron: Asymmetry 13:691-695.

Weller, S. et al. (2013) "Bioequivalence of a Dolutegravir, Abacavir, and Lamivudine Fixed-Dose Combination Tablet and the Effect of Food" Poster A-1572, 53rd Interscience Conference on Antimicrobial Agents and Chemotherapy; Sep. 10-13; Denver, CO.

Weller, S. et al. (2013) "Pharmacokinetics (PK) and Safety of Dolutegravir (DTG) in Subjects With Severe Renal Impairment and Healthy Controls" Poster A-1571, 53rd Interscience Conference on Antimicrobial Agents and Chemotherapy; Sep. 10-13; Denver, CO.

Wensing, A. et al. (2014) "Special Contribution. 2014 Update of the Drug Resistance Mutations in HIV-1" IAS-USA Topics in Antiviral Medicine 22(3):642-650.

Wolkowicz, U.M. et al. (2014) "Structural Basis of Mos1 Transposase Inhibition by the Anti-retroviral Drug Raltegravir" ACS Chem. Biol. 9:743-751.

Wu, B. et al. (2008) "Enantioselective Desymmetrization of meso-Aziridines with TMSN$_3$ and TMSCN Catalyzed by Discrete Yttrium Complexes" Angew. Chem. Int. Ed. 48:1126-1129, Supporting Information.

Wu, Y.Q. et al. (1993) "Preparation of the Pure Diastereomeric Forms of S-(5'-Deoxy-5'-adenosyl)-1-ammonio-4-methyl sulfonio-2 cyclopentene and Their Evaluation as Irreversible Inhibitors of S-Adenosylmethionine Decarboxylase from *Escherichia coli*" Bioorganic & Medicinal Chemistry 1(5):349-360.

Ye, T. et al. (1994) "Stereoselective Synthesis of Disubstituted 3(2H)-Furanones via Catalytic Intramolecular C-H Insertion Reactions of [alpha]-Diazo-[beta]-Keto Esters Including Asymmetric Induction" Tetrahedron Letters 35(39):7626-7272.

Zhao, X.Z. et al. (2014) "4-Amino-1-hydroxy-2-oxo-1,8-naphthyridine-Containing Compounds Having High Potency against Raltegravir-Resistant Integrase Mutants of HIV-1" J. Med. Chem. 57:5190-5202.

Zheng, X. et al. (2008) "Rapid analysis of a Chinese herbal prescription by liquid chromatography-time-of-flight tandem mass spectrometry" Journal of Chromatography A 1206(2):140-146 (Abstract).

SUBSTITUTED PYRIDO[1,2-A]PYRROLO[1,2-D]PYRAZINES FOR TREATING VIRAL INFECTIONS

CROSS-REFERENCE TO RELATED APPLICATIONS

This application is a Continuation of application Ser. No. 16/572,159, filed Sep. 16, 2019, which is a continuation of application Ser. No.15/982,197, filed May 17, 2018, which is a Continuation of application Ser. No. 15/257,528, filed Sep. 6, 2016, which is a Continuation of application Ser. No. 14/329,697, filed Jul. 11, 2014. application Ser. No. 14/329, 697 claims the benefit of U.S. Provisional Application No. 61/845,807, filed Jul. 12, 2013. The entire contents of these applications are incorporated herein by reference in their entirety.

BACKGROUND

Field

Compounds, compositions, and methods for the treatment of human immunodeficiency virus (HIV) infection are disclosed. In particular, novel polycyclic carbamoylpyridone compounds and methods for their preparation and use as therapeutic or prophylactic agents are disclosed.

Description of the Related Art

Human immunodeficiency virus infection and related diseases are a major public health problem worldwide. Human immunodeficiency virus type 1 (HIV-1) encodes three enzymes which are required for viral replication: reverse transcriptase, protease, and integrase. Although drugs targeting reverse transcriptase and protease are in wide use and have shown effectiveness, particularly when employed in combination, toxicity and development of resistant strains have limited their usefulness (Palella, et al. *N. Engl. J Med.* (1998) 338:853-860; Richman, D. D. *Nature* (2001) 410:995-1001).

A goal of antiretroviral therapy is to achieve viral suppression in the HIV infected patient. Current treatment guidelines published by the United States Department of Health and Human Services provide that achievement of viral suppression requires the use of combination therapies, i.e., several drugs from at least two or more drug classes. (Panel on Antiretroviral Guidelines for Adults and Adolescents. Guidelines for the use of antiretroviral agents in HIV-1-infected adults and adolescents. Department of Health and Human Services. Available at http://aidsinfo.nih-.gov/ContentFiles/AdultandAdolescentGL.pdf. Section accessed Mar. 14, 2013.) In addition, decisions regarding the treatment of HIV infected patients are complicated when the patient requires treatment for other medical conditions (Id. at E-12). Because the standard of care requires the use of multiple different drugs to suppress HIV, as well as to treat other conditions the patient may be experiencing, the potential for drug interaction is a criterion for selection of a drug regimen. As such, there is a need for antiretroviral therapies having a decreased potential for drug interactions.

Accordingly, there is a need for new agents that inhibit the replication of HIV and that minimize the potential for drug-drug interactions when co-administered with other drugs.

BRIEF SUMMARY

The present invention is directed to novel polycyclic carbamoylpyridone compounds, having antiviral activity, including stereoisomers and pharmaceutically acceptable salts thereof, and the use of such compounds in the treatment of HIV infections. The compounds of the invention may be used to inhibit the activity of HIV integrase and may be used to reduce HIV replication.

In one embodiment of the present invention, compounds having the following Formula (I):

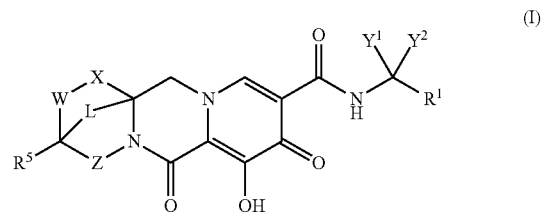

or a stereoisomer or pharmaceutically acceptable salt thereof, wherein:

$Y^1$ and $Y^2$ are each, independently, hydrogen, $C_{1-3}$alkyl or $C_{1-3}$haloalkyl;

$R^1$ is phenyl substituted with one to three halogens;

X is —$CHR^2$—;

W is a bond or —$CHR^3$—

Z is a bond or —$CHR^4$—;

$R^2$, $R^3$, and $R^4$ are each, independently, hydrogen or $C_{1-3}$alkyl;

$R^5$ is hydrogen, $C_{1-3}$alkyl or $C_{1-3}$haloalkyl;

L is —$C(R^a)_2$—, —$C(R^a)_2C(R^a)_2$— or —$C(R^a)_2C(R^a)_2C(R^a)_2$—; and each $R^a$ is, independently, hydrogen, halo, hydroxyl or $C_{1-4}$alkyl.

In another embodiment of the present invention, compounds having the following Formula (I-A) are provided:

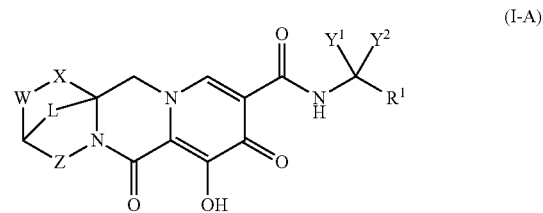

or a stereoisomer or pharmaceutically acceptable salt thereof, wherein:

$Y^1$ and $Y^2$ are each, independently, hydrogen, $C_{1-3}$alkyl or $C_{1-3}$haloalkyl, or $Y^1$ and $Y^2$, together with the carbon atom to which they are attached, form a carbocyclic ring having from 3 to 6 ring atoms or a heterocyclic ring having from 3 to 6 ring atoms, wherein the carbocyclic or heterocyclic ring is optionally substituted with one or more $R^a$;

$R^1$ is optionally substituted aryl or optionally substituted heteroaryl;

X is —O— or —$NR^2$— or —$CHR^2$—;

W is a bond, —O— or —NR— or —$CHR^3$—;

Z is a bond or —$CHR^4$—;

$R^2$, $R^3$ and $R^4$ are each, independently, hydrogen or $C_{1-3}$alkyl;

L is $-C(R^a)_2-$, $-C(R^a)_2C(R^a)_2-$, $-C(R^a)_2C(R^a)_2C(R^a)_2-$, $-C(R^a)_2C(R^a)_2C(R^a)_2C(R^a)_2-$, $-C(R^a)_2OC(R^a)_2-$, $-C(R^a)_2NR^aC(R^a)_2-$, $-C(R^a)_2SC(R^a)_2-$, $-C(R^a)_2S(O)C(R^a)_2-$, $-C(R^a)_2SO_2C(R^a)_2-$, $-C(R^a)_2OC(R^a)_2C(R^a)_2-$, $-C(R^a)_2C(R^a)_2OC(R^a)_2-$, $-C(R^a)_2NR^aC(R^a)_2C(R^a)_2-$, $-C(R^a)_2C(R^a)_2NR^aC(R^a)_2-$, $-C(R^a)_2SC(R^a)_2C(R^a)_2-$, $-C(R^a)_2C(R^a)_2SC(R^a)_2-$, $-C(R^a)_2S(O)C(R^a)_2C(R^a)_2-$, $-C(R^a)_2C(R^a)_2S(O)C(R^a)_2-$, $-C(R^a)_2SO_2C(R^a)_2C(R^a)_2-$, $-C(R^a)_2C(R^a)_2SO_2C(R^a)_2-$, $-C(R^a)_2SO_2NR^aC(R^a)_2-$ or $-C(R^a)_2NR^aSO_2C(R^a)_2-$; and each $R^a$ is, independently, hydrogen, halo, hydroxyl or $C_{1-4}$alkyl, or wherein two $R^a$ groups, together with the carbon atom to which they are attached, form C=O.

In a further embodiment, compounds are provided having the following Formula (I-B):

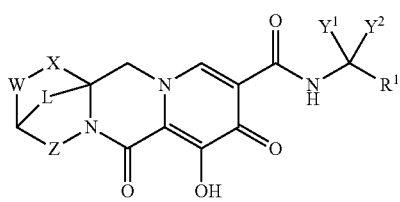

(I-B)

or a stereoisomer or pharmaceutically acceptable salt thereof, wherein:

$Y^1$ and $Y^2$ are each, independently, hydrogen, $C_{1-3}$alkyl or $C_{1-3}$haloalkyl;

$R^1$ is phenyl substituted with one to three halogens;

X is $-CHR^2-$;

W is a bond or $-CHR^3-$

Z is a bond or $-CHR^4-$;

$R^2$, $R^3$, and $R^4$ are each, independently, hydrogen or $C_{1-3}$alkyl;

L is $-C(R^a)_2-$, $-C(R^a)_2C(R^a)_2-$ or $-C(R^a)_2C(R^a)_2C(R^a)_2-$; and each $R^a$ is, independently, hydrogen, halo, hydroxyl or $C_{1-4}$alkyl.

In another embodiment, compounds are provided having the following Formula (II):

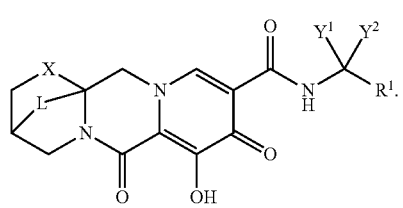

(II)

In a further embodiment, compounds are provided having the following Formula (II-A):

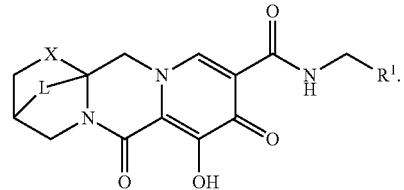

(II-A)

In another embodiment, compounds are provided having the following Formula (III):

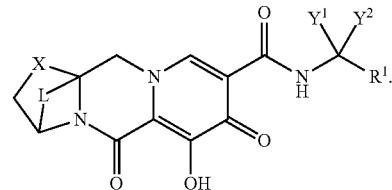

(III)

In a further embodiment, compounds are provided having the following Formula (III-A):

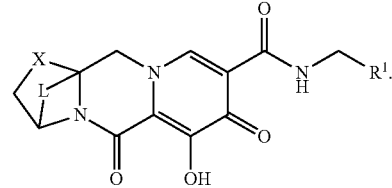

(III-A)

In another embodiment, compounds are provided having the following Formula (IV):

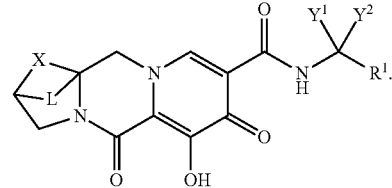

(IV)

In a further embodiment, compounds are provided having the following Formula (IV-A):

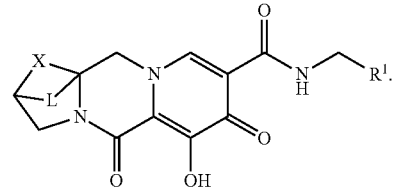

(IV-A)

In another embodiment, L is $-C(R^a)_2-$. In a further embodiment, L is $-C(R^a)_2C(R^a)_2-$. In still a further embodiment, L is —C(R$^a$)$_2$C(R$^a$)$_2$C(R$^a$)$_2$—. In still a further embodiment, each R$^a$ is hydrogen.

In another embodiment, R$^1$ is substituted with one halogen. In a further embodiment, R$^1$ is 4-fluorophenyl or 2-fluorophenyl.

In another embodiment, R$^1$ is substituted with two halogens. In a further embodiment, R$^1$ is 2,4-difluorophenyl, 2,3-difluorophenyl, 2,6-difluorophenyl, 3-fluoro-4-chlorophenyl, 3,4-difluorophenyl, 2-fluoro-4-chlorophenyl, or 3,5-difluorophenyl. In still a further embodiment, R$^1$ is 2,4-difluorophenyl.

In another embodiment, R$^1$ is substituted with three halogens. In a further embodiment, R$^1$ is 2,4,6-trifluorophenyl or 2,3,4-trifluorophenyl. In still a further embodiment, R$^1$ is 2,4,6-trifluorophenyl.

In yet another embodiment compounds are provided having the following structures:

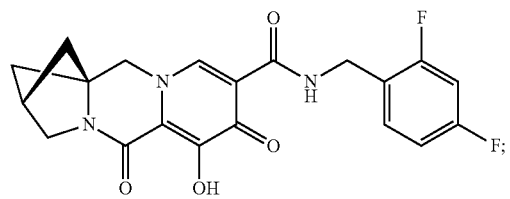

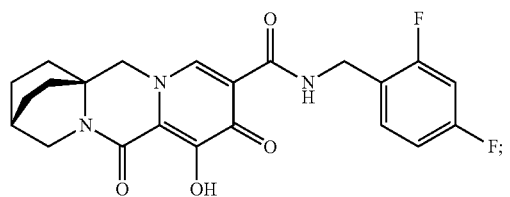

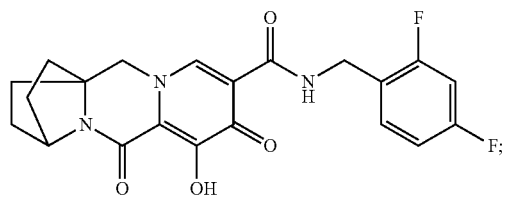

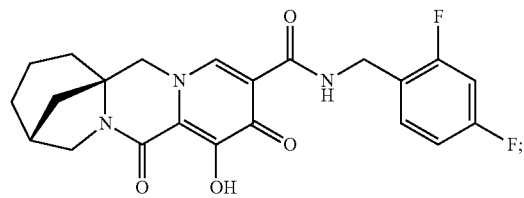

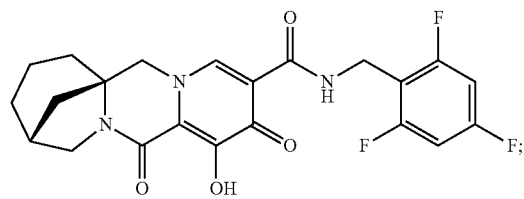

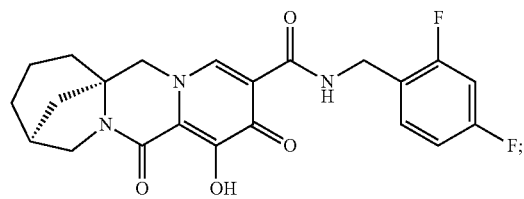

-continued

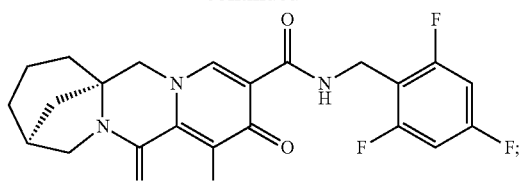

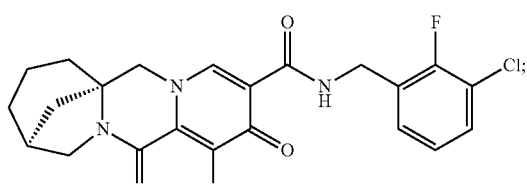

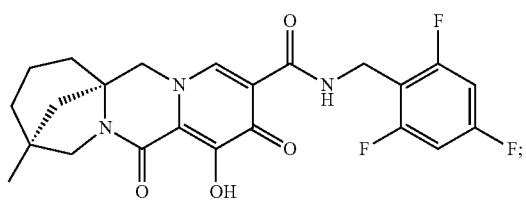

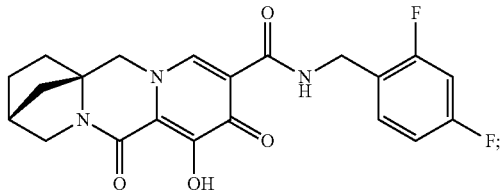

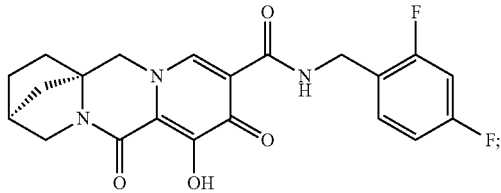

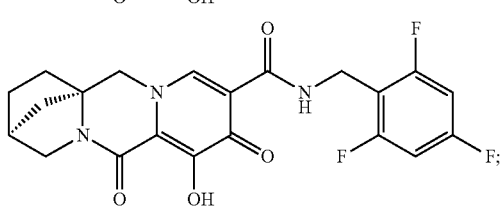

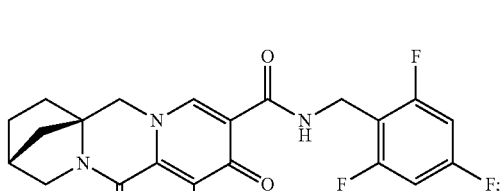

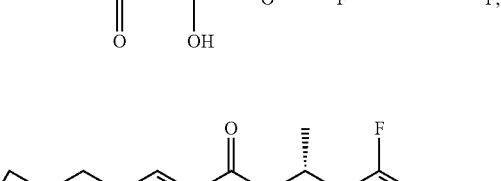

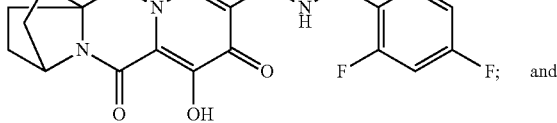

and

-continued

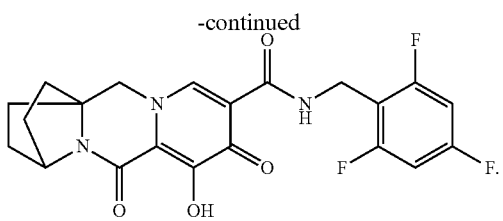

In another embodiment, a pharmaceutical composition is provided comprising a compound having Formula (I), (I-A), (I-B), (II), (II-A), (III), (III-A), (IV), (IV-A), or a stereoisomer or pharmaceutically acceptable salt thereof, and a pharmaceutically acceptable carrier, diluent or excipient.

The invention also provides the use of a pharmaceutical composition as described hereinabove for the treatment of an HIV infection in a human being having or at risk of having the infection.

In another embodiment, a method of using a compound having Formula (I), (I-A), (I-B), (II), (II-A), (III), (III-A), (IV), (IV-A), or a stereoisomer or pharmaceutically acceptable salt thereof, in therapy is provided. In particular, a method of treating the proliferation of the HIV virus, treating AIDS, or delaying the onset of AIDS or ARC symptoms in a mammal (e.g. a human) is provided, comprising administering to the mammal a compound having Formula (I), (I-A), (I-B), (II), (II-A), (III), (III-A), (IV), (IV-A), or a stereoisomer or pharmaceutically acceptable salt thereof, and a pharmaceutically acceptable carrier, diluent or excipient.

In another embodiment, use of a compound of Formula (I), (I-A), (I-B), (II), (II-A), (III), (III-A), (IV), or (IV-A), as described herein, or a pharmaceutically acceptable salt thereof, for the treatment of an HIV infection in a human being having or at risk of having the infection is disclosed.

In another embodiment, the use of a compound of Formula (I), (I-A), (I-B), (II), (II-A), (III), (III-A), (IV), or (IV-A), as described herein, or a pharmaceutically acceptable salt thereof, for the manufacture of a medicament for the treatment of an HIV infection in a human being having or at risk of having the infection is disclosed.

In another embodiment, an article of manufacture comprising a composition effective to treat an HIV infection; and packaging material comprising a label which indicates that the composition can be used to treat infection by HIV is disclosed. Exemplary compositions comprise a compound of Formula (I), (I-A), (I-B), (II), (II-A), (III), (III-A), (IV), or (IV-A), according to this invention or a pharmaceutically acceptable salt thereof.

In still another embodiment, a method of inhibiting the replication of HIV is disclosed. The method comprises exposing the virus to an effective amount of the compound of Formula (I), (I-A), (I-B), (II), (II-A), (III), (III-A), (IV), or (IV-A), or a salt thereof, under conditions where replication of HIV is inhibited.

In another embodiment, the use of a compound of Formula (I), (I-A), (I-B), (II), (II-A), (III), (III-A), (IV), (IV-A), or a pharmaceutically acceptable salt thereof to inhibit the activity of the HIV integrase enzyme is disclosed.

In another embodiment, the use of a compound of Formula (I), (I-A), (I-B), (II), (II-A), (III), (III-A), (IV), (IV-A), or a salt thereof, to inhibit the replication of HIV is disclosed.

Other embodiments, objects, features and advantages will be set forth in the detailed description of the embodiments that follows, and in part will be apparent from the description, or may be learned by practice, of the claimed invention. These objects and advantages will be realized and attained by the processes and compositions particularly pointed out in the written description and claims hereof. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

DETAILED DESCRIPTION

In the following description, certain specific details are set forth in order to provide a thorough understanding of various embodiments of the invention. However, one skilled in the art will understand that the invention may be practiced without these details. The description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

Definitions

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —$NH_2$ radical.
"Cyano" refers to the —CN radical.
"Hydroxy" or "hydroxyl" refers to the —OH radical.
"Imino" refers to the =NH substituent.
"Nitro" refers to the —$NO_2$ radical.
"Oxo" refers to the =O substituent.
"Thioxo" refers to the =S substituent.
"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. In certain embodiments, "Alkyl" refers to a straight or branched hydrocarbon chain radical consisting solely of carbon and hydrogen atoms, which is saturated, having from one to twelve carbon atoms ($C_1$-$C_{12}$ alkyl), or from one to eight carbon atoms ($C_1$-$C_8$ alkyl), or from one to six carbon atoms ($C_1$-$C_6$ alkyl), or from one to four carbon atoms ($C_1$-$C_4$ alkyl), and which is attached to the rest of the molecule by a single bond. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —$OR_A$ where $R_A$ is an alkyl radical as defined above containing one to twelve carbon atoms. Unless stated otherwise specifically in the specification, an alkoxy group may be optionally substituted.

"Alkylamino" refers to a radical of the formula —$NHR_A$ or —$NR_A R_A$ where each $R_A$ is, independently, an alkyl radical as defined above containing one to twelve carbon atoms. Unless stated otherwise specifically in the specification, an alkylamino group may be optionally substituted.

"Thioalkyl" refers to a radical of the formula —$SR_A$ where $R_A$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. In a preferred embodiment, the aryl radical is a monocyclic ring system. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_B$—$R_C$ where $R_B$ is an alkylene chain as defined above and $R_C$ is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. In certain preferred embodiments, "Cycloalkyl" or "carbocyclic ring" refers to a stable non-aromatic monocyclic hydrocarbon radical consisting solely of carbon and hydrogen atoms, having from three to fifteen carbon atoms, or having from three to ten carbon atoms, or having from three to eight carbon atoms and which is saturated or unsaturated and attached to the rest of the molecule by a single bond Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1] heptanyl, and the like. Unless otherwise stated specifically in the specification, a cycloalkyl group may be optionally substituted.

"Cycloalkylalkyl" refers to a radical of the formula —$R_B R_D$ where $R_B$ is an alkylene chain as defined above and $R_D$ is a cycloalkyl radical as defined above. Unless stated otherwise specifically in the specification, a cycloalkylalkyl group may be optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. In certain preferred embodiments, the heterocyclyl radical is a monocyclic ring system; and/or the nitrogen, carbon or sulfur atoms in the heterocyclyl radical is optionally oxidized; and/or the nitrogen atom is optionally quaternized. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, an N-heterocyclyl group may be optionally substituted.

"Heterocyclylalkyl" refers to a radical of the formula —$R_B R_E$ where $R_B$ is an alkylene chain as defined above and $R_E$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; the nitrogen, carbon or sulfur atoms in the heteroaryl radical may be optionally oxidized; and the nitrogen atom may be optionally quaternized. In certain preferred embodiments, the heteroaryl radical is a monocyclic ring system; and/or the nitrogen, carbon or sulfur atoms in the heteroaryl radical is optionally oxidized; and/or the nitrogen atom is optionally quaternized. Examples include, but are not limited to, azepinyl, acridinyl, benzimidazolyl, benzothiazolyl, benzindolyl, benzodioxolyl, benzofuranyl, benzoxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_B R_F$ where $R_B$ is an alkylene chain as defined above and $R_F$ is a heteroaryl radical as defined above. Unless stated otherwise specifically in the specification, a heteroarylalkyl group may be optionally substituted.

The term "substituted" used herein means any of the above groups (i.e., alkyl, alkylene, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_G R_H$, —$NR_G C(=O)R_H$, —$NR_G C(=O)NR_G R_H$, —$NR_G C(=O)OR_H$, —$NR_G C(=NR_g)NR_G R_H$, —$NR_G SO_2 R_H$, —$OC(=O)NR_G R_H$, —$OR_G$, —$SR_G$, —$SOR_G$, —$SO_2 R_G$, —$OSO_2 R_G$, —$SO_2 OR_G$, =$NSO_2 R_G$, and —$SO_2 NR_G R_H$. "Substituted also means any of the above groups in which one or more hydrogen atoms are replaced with —$C(=O)R_G$, —$C(=O)OR_G$, —$C(=O)NR_G R_H$, —$CH_2 SO_2 R_G$, —$CH_2 SO_2 NR_G R_H$. In the foregoing, $R_G$ and $R_H$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

The term "protecting group," as used herein, refers to a labile chemical moiety which is known in the art to protect reactive groups including without limitation, hydroxyl and amino groups, against undesired reactions during synthetic procedures. Hydroxyl and amino groups protected with a protecting group are referred to herein as "protected hydroxyl groups" and "protected amino groups", respectively. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999). Generally, groups are protected or present as a precursor that will be inert to reactions that modify other areas of the parent molecule for conversion into their final groups at an appropriate time. Further representative protecting or precursor groups are discussed in Agrawal, et al., Protocols for Oligonucleotide Conjugates, Eds, Humana Press; New Jersey, 1994; Vol. 26 pp. 1-72. Examples of "hydroxyl protecting groups" include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p-nitrobenzyl, triphenylmethyl, trimethylsilyl, triethylsilyl, t-butyldimethylsilyl, t-butyldiphenylsilyl (TBDPS), triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate. Examples of "amino protecting groups" include, but are not limited to, carbamate-protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide-protecting groups, such as 2-nitrobenzenesulfonyl; and imine and cyclic imide protecting groups, such as phthalimido and dithiasuccinoyl.

The invention disclosed herein is also meant to encompass all pharmaceutically acceptable compounds of Formula (I), (I-A), (I-B), (II), (II-A), (III), (III-A), (IV), (IV-A), and stereoisomers or pharmaceutically acceptable salts thereof, being isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$ $^{35}S$ $^{18}F$, $^{36}Cl$, $^{123}I$, and $^{125}I$, respectively. These radiolabeled compounds could be useful to help determine or measure the effectiveness of the compounds, by characterizing, for example, the site or mode of action, or binding affinity to pharmacologically important site of action. Certain isotopically-labeled compounds of Formula (I), (I-A), (I-B), (II), (II-A), (III), (III-A), (IV), (IV-A), and stereoisomers or pharmaceutically acceptable salts thereof, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability. For example, in vivo half-life may increase or dosage requirements may be reduced. Thus, heavier isotopes may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formula (I), (I-A), (I-B), (II), (II-A), (III), (III-A), (IV), (IV-A), and stereoisomers or pharmaceutically acceptable salts thereof, can generally be prepared by conventional techniques known to those skilled in the art or by processes analogous to those described in the Examples as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabeled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Examples of "pharmaceutically acceptable salts" of the compounds disclosed herein include salts derived from an appropriate base, such as an alkali metal (for example, sodium), an alkaline earth metal (for example, magnesium), ammonium and $NX_4^+$ (wherein X is $C_1$-$C_4$ alkyl). Pharmaceutically acceptable salts of a nitrogen atom or an amino group include for example salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, hydrobromic, sulfuric, phosphoric and sulfamic acids. Pharmaceutically acceptable salts of a compound of a hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds disclosed herein will typically be pharmaceutically acceptable, i.e. they will be salts derived from a physiologically acceptable acid or base. However, salts of acids or bases which are not pharmaceutically acceptable may also find use, for example, in the preparation or purification of a compound of Formula (I), (I-A), (I-B), (II), (II-A), (III), (III-A), (IV), (IV-A), a stereoisomer or pharmaceutically acceptable salt thereof, or another compound of the invention. All salts, whether or not derived from a physiologically acceptable acid or base, are within the scope of the present invention.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines. Finally, it is to be understood that the compositions herein comprise compounds disclosed herein in their un-ionized, as well as zwitterionic form, and combinations with stoichiometric amounts of water as in hydrates.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a therapeutically effective amount can be determined routinely by one of ordinary skill in the art having regard to their own knowledge, the state of the art, and this disclosure.

The term "treatment" as used herein is intended to mean the administration of a compound or composition according to the present invention to alleviate or eliminate symptoms of HIV infection and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectible levels in the blood, and the administration of a compound or composition according to the present invention to prevent perinatal transmission of HIV from mother to baby, by administration to the mother before giving birth and to the child within the first days of life.

The term "antiviral agent" as used herein is intended to mean an agent (compound or biological) that is effective to inhibit the formation and/or replication of a virus in a human being, including but not limited to agents that interfere with either host or viral mechanisms necessary for the formation and/or replication of a virus in a human being.

The term "inhibitor of HIV replication" as used herein is intended to mean an agent capable of reducing or eliminating the ability of HIV to replicate in a host cell, whether in vitro, ex vivo or in vivo.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)-for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

Compounds

As noted above, in one embodiment of the present invention, compounds are provided having the following Formula (I):

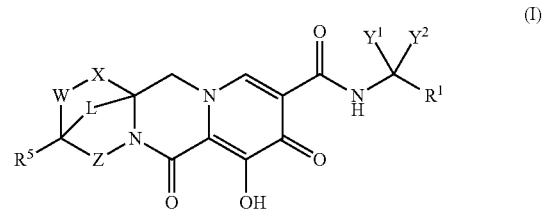

or a stereoisomer or pharmaceutically acceptable salt thereof, wherein:
$Y^1$ and $Y^2$ are each, independently, hydrogen, $C_{1-3}$alkyl or $C_{1-3}$haloalkyl;
$R^1$ is phenyl substituted with one to three halogens;
X is —$CHR^2$—;
W is a bond or —$CHR^3$—
Z is a bond or —$CHR^4$—;
$R^2$, $R^3$, and $R^4$ are each, independently, hydrogen or $C_{1-3}$alkyl;
$R^5$ is hydrogen, $C_{1-3}$alkyl or $C_{1-3}$haloalkyl;
L is —$C(R^a)_2$—, —$C(R^a)_2C(R^a)_2$— or —$C(R^a)_2C(R^a)_2C(R^a)_2$—; and
each $R^a$ is, independently, hydrogen, halo, hydroxyl or $C_{1-4}$alkyl.

In another embodiment of the present invention, compounds having the following Formula (I-A) are provided:

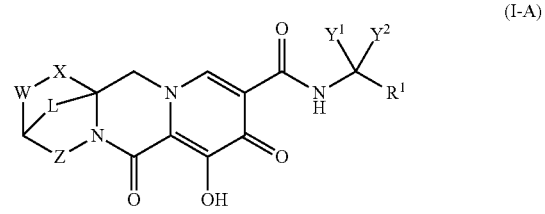

or a stereoisomer or pharmaceutically acceptable salt thereof, wherein:
- $Y^1$ and $Y^2$ are each, independently, hydrogen, $C_{1-3}$alkyl or $C_{1-3}$haloalkyl, or $Y^1$ and $Y^2$, together with the carbon atom to which they are attached, form a carbocyclic ring having from 3 to 6 ring atoms or a heterocyclic ring having from 3 to 6 ring atoms, wherein the carbocyclic or heterocyclic ring is optionally substituted with one or more $R^a$;
- $R^1$ is optionally substituted aryl or optionally substituted heteroaryl;
- X is —O— or —NR$^2$— or —CHR$^2$—;
- W is a bond, —O— or —NR— or —CHR$^3$—;
- Z is a bond or —CHR$^4$—;
- $R^2$, $R^3$ and $R^4$ are each, independently, hydrogen or $C_{1-3}$alkyl;
- L is —C(R$^a$)$_2$—, —C(R$^a$)$_2$C(R$^a$)$_2$—, —C(R$^a$)$_2$C(R$^a$)$_2$C(R$^a$)$_2$—, —C(R$^a$)$_2$C(R$^a$)$_2$C(R$^a$)$_2$C(R$^a$)$_2$—, —C(R$^a$)$_2$OC(R$^a$)$_2$—, —C(R$^a$)$_2$NR$^a$C(R$^a$)$_2$—, —C(R$^a$)$_2$SC(R$^a$)$_2$—, —C(R$^a$)$_2$S(O)C(R$^a$)$_2$—, —C(R$^a$)$_2$SO$_2$C(R$^a$)$_2$—, —C(R$^a$)$_2$OC(R$^a$)$_2$C(R$^a$)$_2$—, —C(R$^a$)$_2$C(R$^a$)$_2$OC(R$^a$)$_2$—, —C(R$^a$)$_2$NR$^a$C(R$^a$)$_2$C(R$^a$)$_2$—, —C(R$^a$)$_2$C(R$^a$)$_2$NR$^a$C(R$^a$)$_2$—, —C(R$^a$)$_2$SC(R$^a$)$_2$C(R$^a$)$_2$—, —C(R$^a$)$_2$C(R$^a$)$_2$SC(R$^a$)$_2$—, —C(R$^a$)$_2$S(O)C(R$^a$)$_2$C(R$^a$)$_2$—, —C(R$^a$)$_2$C(R$^a$)$_2$S(O)C(R$^a$)$_2$—, —C(R$^a$)$_2$SO$_2$C(R$^a$)$_2$C(R$^a$)$_2$—, —C(R$^a$)$_2$C(R$^a$)$_2$SO$_2$C(R$^a$)$_2$—, —C(R$^a$)$_2$SO$_2$NR$^a$C(R$^a$)$_2$— or —C(R a)$_2$NR$^a$SO$_2$C(R$^a$)$_2$—; and
- each $R^a$ is, independently, hydrogen, halo, hydroxyl or $C_{1-4}$alkyl, or wherein two $R^a$ groups, together with the carbon atom to which they are attached, form C=O.

In a further embodiment, compounds are provided having the following Formula (I-B):

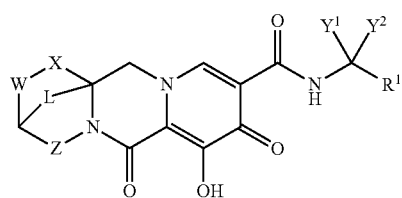

(I-B)

or a stereoisomer or pharmaceutically acceptable salt thereof, wherein:
- $Y^1$ and $Y^2$ are each, independently, hydrogen, $C_{1-3}$alkyl or $C_{1-3}$haloalkyl;
- $R^1$ is phenyl substituted with one to three halogens;
- X is —CHR$^2$—;
- W is a bond or —CHR$^3$—
- Z is a bond or —CHR$^4$—;
- $R^2$, $R^3$, and $R^4$ are each, independently, hydrogen or $C_{1-3}$alkyl;
- L is —C(R$^a$)$_2$—, —C(R$^a$)$_2$C(R$^a$)$_2$— or —C(R$^a$)$_2$C(R$^a$)$_2$C(R$^a$)$_2$—; and
- each $R^a$ is, independently, hydrogen, halo, hydroxyl or $C_{1-4}$alkyl.

In another embodiment, compounds are provided having the following Formula (II):

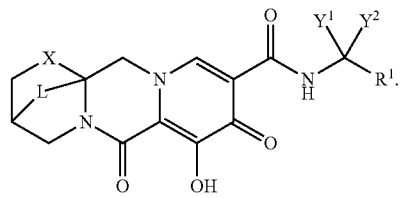

(II)

In a further embodiment, compounds are provided having the following Formula (II-A):

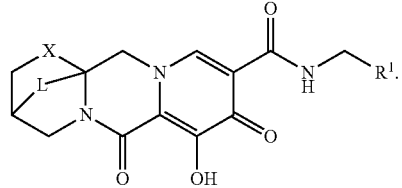

(II-A)

In another embodiment, compounds are provided having the following Formula (III):

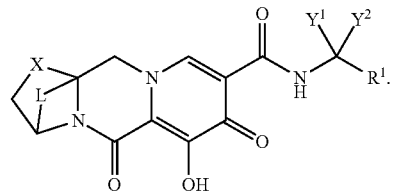

(III)

In a further embodiment, compounds are provided having the following Formula (III-A):

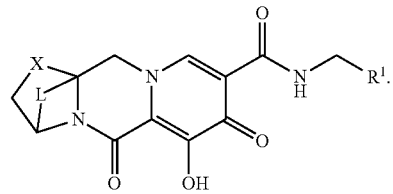

(III-A)

In another embodiment, compounds are provided having the following Formula (IV):

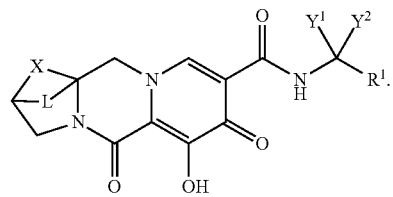

(IV)

In a further embodiment, compounds are provided having the following Formula (IV-A):

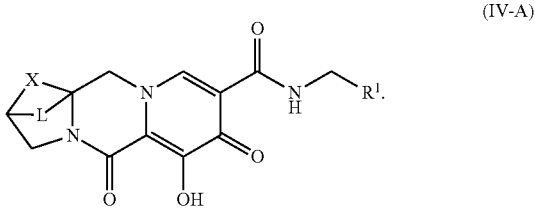

(IV-A)

In another embodiment, L is —C(R$^a$)$_2$—. In a further embodiment, L is —C(R$^a$)$_2$C(R$^a$)$_2$—. In still a further embodiment, L is —C(R$^a$)$_2$C(R$^a$)$_2$C(R$^a$)$_2$—.

In a certain embodiment, each R$^a$ is, independently, hydrogen, halo, hydroxyl or methyl. In a certain embodiment, each R$^a$ is, independently, hydrogen or methyl. In still a further embodiment, each R$^a$ is hydrogen.

In another embodiment, R$^1$ is substituted with one halogen. In a further embodiment, R$^1$ is 4-fluorophenyl or 2-fluorophenyl.

In another embodiment, R$^1$ is substituted with two halogens. In a further embodiment, R$^1$ is 2,4-difluorophenyl, 2,3-difluorophenyl, 2,6-difluorophenyl, 3-fluoro-4-chlorophenyl, 3,4-difluorophenyl, 2-fluoro-4-chlorophenyl, or 3,5-difluorophenyl. In still a further embodiment, R$^1$ is 2,4-difluorophenyl.

In another embodiment, R$^1$ is substituted with three halogens. In a further embodiment, R$^1$ is 2,4,6-trifluorophenyl or 2,3,4-trifluorophenyl. In still a further embodiment, R$^1$ is 2,4,6-trifluorophenyl.

In a certain embodiment, Y$^1$ and Y$^2$ are each, independently, hydrogen, methyl, CF$_2$ or CF$_3$. In a certain embodiment, Y$^1$ and Y$^2$ are each, independently, hydrogen or methyl.

In a certain embodiment, X is —CHR$^2$—; W is —CHR$^3$—; and Z is —CHR$^4$—. In a certain embodiment, X is —CHR$^2$—; W is a bond; and Z is —CHR$^4$—. In a certain embodiment, X is —CHR$^2$—; W is —CHR$^3$—; and Z is a bond.

In a certain embodiment, R$^2$, R$^3$, and R$^4$ are each, independently, hydrogen or methyl. In a certain embodiment, R$^2$, R$^3$, and R$^4$ are each hydrogen.

In yet another embodiment of the present invention, compounds of any one of Formulas (I), (I-A), (I-B), (II), (II-A), (III), (III-A), (IV), or (IV-A), or a stereoisomer or pharmaceutically acceptable salt thereof, having antiviral activity are provided.

In one embodiment, a pharmaceutical composition is provided comprising a compound of any one of Formulas (I), (I-A), (I-B), (II), (II-A), (III), (III-A), (IV), or (IV-A), or a stereoisomer or pharmaceutically acceptable salt thereof, and a pharmaceutically acceptable carrier, diluent or excipient.

Another embodiment is provided comprising a method of treating or preventing an HIV infection in a human having or at risk of having the infection by administering to the human a therapeutically effective amount of a compound of any one of Formulas (I), (I-A), (I-B), (II), (II-A), (III), (III-A), (IV), or (IV-A), or a pharmaceutical composition thereof.

In another embodiment, the use of a compound of any one of Formulas (I), (I-A), (I-B), (II), (II-A), (III), (III-A), (IV), or (IV-A), or a pharmaceutical composition thereof, for the treatment or prevention of an HIV infection in a human having or at risk of having the infection is provided.

In another embodiment, the use in medical therapy of a compound of any one of the Formulas (I), (I-A), (I-B), (II), (II-A), (III), (III-A), (IV), or (IV-A), or a pharmaceutical composition thereof, is provided.

In another embodiment, the use of a compound of any one of the Formulas (I), (I-A), (I-B), (II), (II-A), (III), (III-A), (IV), or (IV-A), or a pharmaceutical composition thereof, for use in the prophylactic or therapeutic treatment of an HIV infection is provided As further noted above, in another embodiment of the present invention, compounds having antiviral activity are provided, the compounds having the following Formula (I-A):

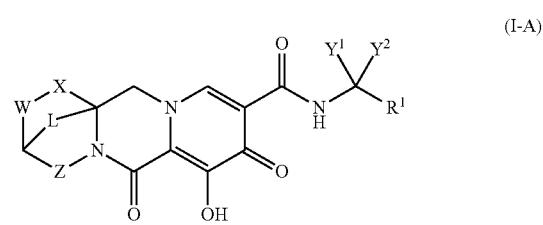

(I-A)

or a stereoisomer or pharmaceutically acceptable salt thereof,
wherein:
Y$^1$ and Y$^2$ are each, independently, hydrogen, C$_{1-3}$alkyl or C$_{1-3}$haloalkyl, or Y$^1$ and Y$^2$, together with the carbon atom to which they are attached, form a carbocyclic ring having from 3 to 6 ring atoms or a heterocyclic ring having from 3 to 6 ring atoms, wherein the carbocyclic or heterocyclic ring is optionally substituted with one or more R$^a$;
R$^1$ is optionally substituted aryl or optionally substituted heteroaryl;
X is —O— or —NR$^2$— or —CHR$^2$—;
W is a bond, —O— or —NR— or —CHR$^3$—;
Z is a bond or —CHR$^4$—;
R$^2$, R$^3$ and R$^4$ are each, independently, hydrogen or C$_{1-3}$alkyl;
L is —C(R$^a$)$_2$—, —C(R$^a$)$_2$C(R$^a$)$_2$—, —C(R$^a$)$_2$C(R$^a$)$_2$C(R$^a$)$_2$—, —C(R$^a$)$_2$C(R$^a$)$_2$C(R$^a$)$_2$C(R$^a$)$_2$—, —C(R$^a$)$_2$OC(R$^a$)$_2$-, —C(R$^a$)$_2$NR$^a$C(R$^a$)$_2$—, —C(R$^a$)$_2$SC(R$^a$)$_2$—, —C(R$^a$)$_2$S(O)C(R$^a$)$_2$—, —C(R$^a$)$_2$SO$_2$C(R$^a$)$_2$—, —C(R$^a$)$_2$OC(R$^a$)$_2$C(R$^a$)$_2$—, —C(R$^a$)$_2$C(R$^a$)$_2$OC(R$^a$)$_2$—, —C(R$^a$)$_2$NR$^a$C(R$^a$)$_2$C(R$^a$)$_2$—, —C(R$^a$)$_2$C(R$^a$)$_2$NR$^a$C(R$^a$)$_2$—C(R$^a$)$_2$SC(R$^a$)$_2$C(R$^a$)$_2$—, —C(R$^a$)$_2$C(R$^a$)$_2$SC(R$^a$)$_2$—, —C(R$^a$)$_2$S(O)C(R$^a$)$_2$C(R$^a$)$_2$—, —C(R$^a$)$_2$C(R$^a$)$_2$S(O) C(R$^a$)$_2$—, —C(R$^a$)$_2$SO$_2$C(R$^a$)$_2$C(R$^a$)$_2$—, —C(R$^a$)$_2$C(R$^a$)$_2$SO$_2$C(R$^a$)$_2$—, —C(R$^a$)$_2$SO$_2$NR$^a$C(R$^a$)$_2$— or —C(R a)$_2$NR$^a$SO$_2$C(R$^a$)$_2$—; and
each R$^a$ is, independently, hydrogen, halo, hydroxyl or C$_{1-4}$alkyl, or wherein two R$^a$ groups, together with the carbon atom to which they are attached, form C=O.

In another embodiment, compounds are provided having one of the following Formulas (II), (III), or (IV):

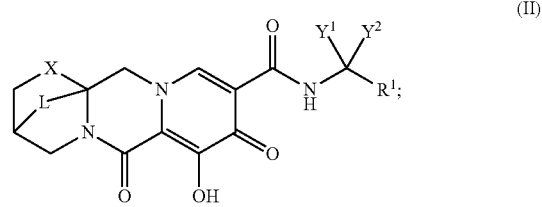

(II)

-continued (III)

(IV)

In another embodiment, compounds are provided having the following Formula (II-A):

(II-A)

In another embodiment, compounds are provided having one of the following Formulas (II-B), (II-C), (II-D) or (II-E):

(II-B)

(II-C)

(II-D)

(II-E)

In another embodiment, compounds are provided having one of the following Formulas (II-F), (II-G), (II-H), or (II-I):

(II-F)

(II-G)

(II-H)

(II-I)

In another embodiment, compounds are provided having the following Formula (III-A):

(III-A)

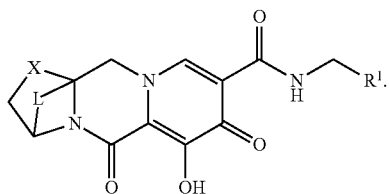

In another embodiment, compounds are provided having one of the following Formulas (III-B), (III-C), (III-D) or (III-E):

(III-B)

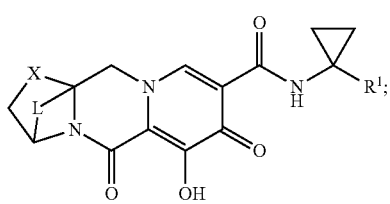

(III-C)

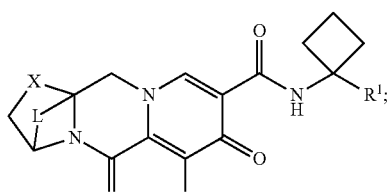

(III-D)

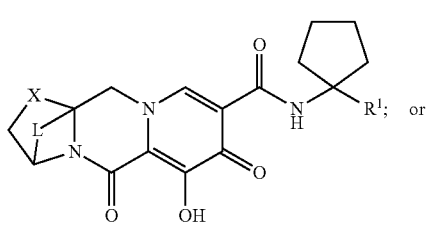

(III-E)

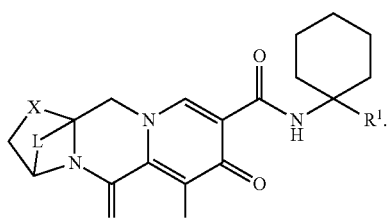

In another embodiment, compounds are provided having one of the following Formulas (III-F), (III-G), (III-H), or (III-I):

(III-F)

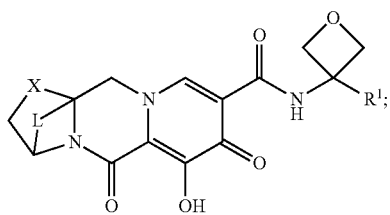

(III-G)

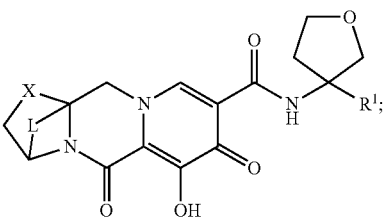

(III-H)

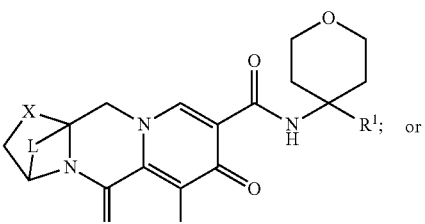

or (III-I)

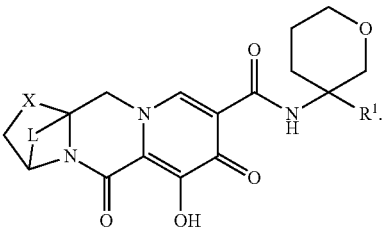

In another embodiment, compounds are provided having the following Formula (IV-A):

(IV-A)

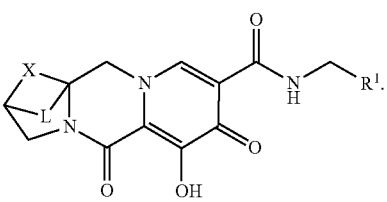

In another embodiment, compounds are provided having one of the following Formulas (IV-B), (IV-C), (IV-D) or (IV-E):

(IV-B)

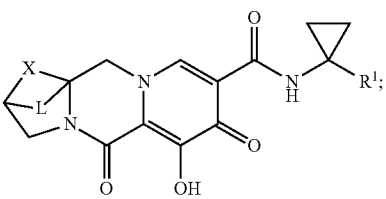

(IV-C)

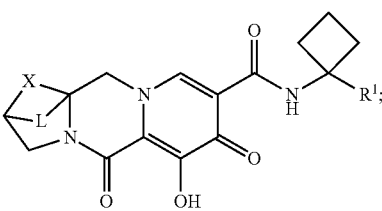

-continued

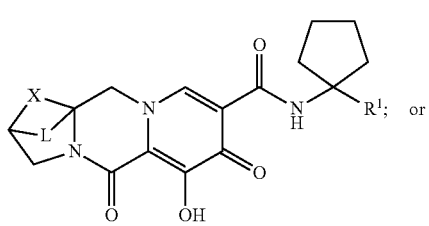
(IV-D)

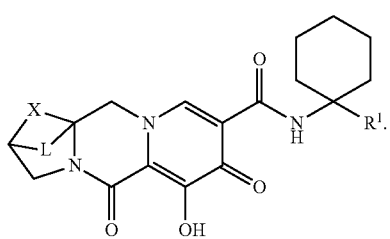
(IV-E)

In another embodiment, compounds are provided having one of the following Formulas (IV-F), (IV-G), (IV-H), or (IV-I):

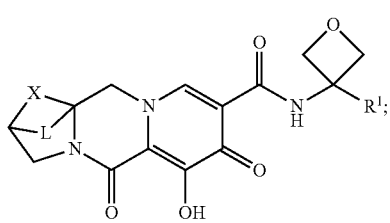
(IV-F)

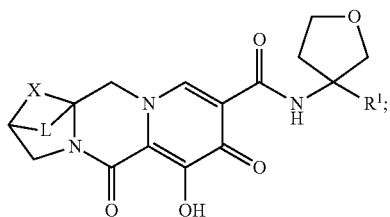
(IV-G)

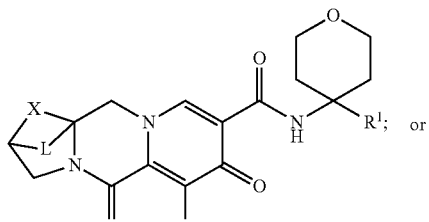
(IV-H)

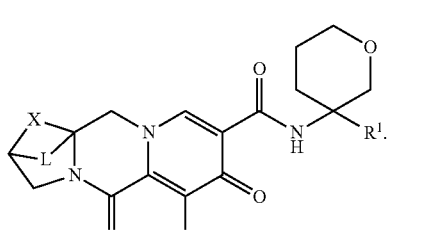
(IV-I)

In another embodiment, L is —C(R$^a$)$_2$—, —C(R$^a$)$_2$C(R$^a$)$_2$—, —C(R$^a$)$_2$C(R$^a$)$_2$C(R$^a$)$_2$—, or —C(R$^a$)$_2$C(R$^a$)$_2$C(R$^a$)$_2$C(R$^a$)$_2$—. In a further embodiment, L is —C(R$^a$)$_2$—. In still a further embodiment, L is —C(R$^a$)$_2$C(R$^a$)$_2$—. In still a further embodiment, L is —C(R$^a$)$_2$C(R$^a$)$_2$C(R$^a$)$_2$—. In still a further embodiment, each R$^a$ is hydrogen.

In another embodiment, L is —C(R$^a$)$_2$OC(R$^a$)$_2$—, —C(R$^a$)$_2$NR$^a$C(R$^a$)$_2$—, —C(R$^a$)$_2$SC(R$^a$)$_2$—, —C(R$^a$)$_2$S(O)C(R$^a$)$_2$—, or —C(R$^a$)$_2$SO$_2$C(R$^a$)$_2$—. In a further embodiment, each R$^a$ is hydrogen.

In another embodiment, X is —O—. In another embodiment, X is —NH—. In another embodiment, X is —CH$_2$—.

In another embodiment, R$^1$ is phenyl. In another embodiment, R$^1$ is pyridinyl.

In another embodiment, R$^1$ is substituted with at least one halogen.

In another embodiment, R$^1$ is substituted with one halogen. In a further embodiment, R$^1$ is 4-fluorophenyl or 2-fluorophenyl.

In another embodiment, R$^1$ is substituted with two halogens. In a further embodiment, R$^1$ is 2,4-difluorophenyl, 2,3-difluorophenyl, 2,6-difluorophenyl, 3-fluoro-4-chlorophenyl, 3,4-difluorophenyl, 2-fluoro-4-chlorophenyl, or 3,5-difluorophenyl. In still a further embodiment, R$^1$ is 2,4-difluorophenyl.

In another embodiment, R$^1$ is substituted with three halogens. In a further embodiment, R$^1$ is 2,4,6-trifluorophenyl or 2,3,4-trifluorophenyl. In still a further embodiment, R$^1$ is 2,4,6-trifluorophenyl.

In another embodiment, R$^1$ is 3-trifluoromethyl-4-fluorophenyl or 2-cyclopropoxy-4-fluorophenyl.

In one embodiment, a pharmaceutical composition is provided comprising a compound of any one of Formulas (I), (I-A), (I-B), (II), (II-A), (II-B), (II-C), (II-D), (II-E), (II-F), (II-G), (II-H), (II-I), (III), (III-A), (III-B), (III-C), (III-D), (III-E), (III-F), (III-G), (III-H), (III-I), (IV), (IV-A), (IV-B), (IV-C), (IV-D), (IV-E), (IV-F), (IV-G), (IV-H), and (IV-I), or a stereoisomer or pharmaceutically acceptable salt thereof, and a pharmaceutically acceptable carrier, diluent or excipient.

Another embodiment is provided comprising a method of treating or preventing an HIV infection in a human having or at risk of having the infection by administering to the human a therapeutically effective amount of a compound of any one of Formulas (I), (I-A), (I-B), (II), (II-A), (II-B), (II-C), (II-D), (II-E), (II-F), (II-G), (II-H), (II-I), (III), (III-A), (III-B), (III-C), (III-D), (III-E), (III-F), (III-G), (III-H), (III-I), (IV), (IV-A), (IV-B), (IV-C), (IV-D), (IV-E), (IV-F), (IV-G), (IV-H), and (IV-I), or a pharmaceutical composition thereof.

In another embodiment, the use of a compound of any one of Formulas (I), (I-A), (I-B), (II), (II-A), (II-B), (II-C), (II-D), (II-E), (II-F), (II-G), (II-H), (II-I), (III), (III-A), (III-B), (III-C), (III-D), (III-E), (III-F), (III-G), (III-H), (III-I), (IV), (IV-A), (IV-B), (IV-C), (IV-D), (IV-E), (IV-F), (IV-G), (IV-H), and (IV-I), or a pharmaceutical composition thereof for use in medical therapy. In a particular embodiment, the medical therapy is prevention or treatment of HIV infection in a patient. In a particular embodiment, the medical therapy is treatment of HIV infection in a patient.

In another embodiment, the use of a compound of any one of Formulas (I), (I-A), (I-B), (II), (II-A), (II-B), (II-C), (II-D), (II-E), (II-F), (II-G), (II-H), (II-I), (III), (III-A), (III-B), (III-C), (III-D), (III-E), (III-F), (III-G), (III-H), (III-I), (IV), (IV-A), (IV-B), (IV-C), (IV-D), (IV-E), (IV-F), (IV-G), (IV-H), and (IV-I), or a pharmaceutical composition thereof for the treatment or prevention of an HIV infection in a human having or at risk of having the infection.

In another embodiment the substituent groups of Formulas (I), (I-A), (I-B), (II), (II-A), (II-B), (II-C), (II-D), (II-E), (II-F), (II-G), (II-H), (II-I), (III), (III-A), (III-B), (III-C), (III-D), (III-E), (III-F), (III-G), (III-H), (III-I), (IV), (IV-A), (IV-B), (IV-C), (IV-D), (IV-E), (IV-F), (IV-G), (IV-H), and (IV-I), as set forth above, maybe defined as follows:

$Y^1$ and $Y^2$ are each, independently, hydrogen, $C_{1-3}$alkyl or $C_{1-3}$haloalkyl, or $Y^1$ and $Y^2$, together with the carbon atom to which they are attached, form a carbocyclic ring having from 3 to 6 ring atoms or a heterocyclic ring having from 3 to 6 ring atoms, wherein the carbocyclic or heterocyclic ring is optionally substituted with one or more $R^a$;

$R^1$ is optionally substituted aryl or optionally substituted heteroaryl;

X is —O— or —$NR^2$— or —$CHR^2$—;

W is a bond, —O— or —NR— or —$CHR^3$—;

Z is a bond or —$CHR^4$—;

$R^2$, $R^3$ and $R^4$ are each, independently, hydrogen or $C_{1-3}$alkyl;

L is —$C(R^a)_2$—, —$C(R^a)_2C(R^a)_2$—, —$C(R^a)_2C(R^a)_2C(R^a)_2$—, —$C(R^a)_2C(R^a)_2C(R^a)_2C(R^a)_2$—, —$C(R^a)_2OC(R^a)_2$-, —$C(R^a)NR^aC(R^a)_2$—, —$C(R^a)_2SC(R^a)_2$—, —$C(R^a)_2S(O)C(R^a)_2$—, —$C(R^a)_2SO_2C(R^a)_2$—, —$C(R^a)_2OC(R^a)_2C(R^a)_2$—, —$C(R^a)_2C(R^a)_2OC(R^a)_2$—, —$C(R^a)NR^aC(R^a)_2C(R^a)_2$—, —$C(R^a)_2C(R^a)_2NR^aC(R^a)_2$—, —$C(R^a)_2SC(R^a)_2C(R^a)_2$—, —$C(R^a)_2C(R^a)_2SC(R^a)_2$—, —$C(R^a)_2S(O)C(R^a)_2C(R^a)_2$—, —$C(R^a)_2C(R^a)_2S(O)C(R^a)_2$—, —$C(R^a)_2SO_2C(R^a)_2C(R^a)_2$—, —$C(R^a)_2C(R^a)_2SO_2C(R^a)_2$—, —$C(R^a)_2SO_2NR^aC(R^a)_2$— or —$C(R a)_2NR^aSO_2C(R^a)_2$—; and/or each $R^a$ is, independently, hydrogen, halo, hydroxyl or $C_{1-4}$alkyl, or wherein two $R^a$ groups, together with the carbon atom to which they are attached, form C=O.

It is understood that any embodiment of the compounds of Formulas (I), (I-A), (I-B), (II), (II-A), (II-B), (II-C), (II-D), (II-E), (II-F), (II-G), (II-H), (II-I), (III), (III-A), (III-B), (III-C), (III-D), (III-E), (III-F), (III-G), (III-H), (III-I), (IV), (IV-A), (IV-B), (IV-C), (IV-D), (IV-E), (IV-F), (IV-G), (IV-H), and (IV-I), as set forth above, and any specific substituent set forth herein for a L, $R^1$, $R^2$, $R^3$, $R^4$, $R^5$, $R^a$, W, X, $Y^1$, $Y^2$, or Z group in the compounds of Formulas (I), (I-A), (I-B), (II), (II-A), (II-B), (II-C), (II-D), (II-E), (II-F), (II-G), (II-H), (II-I), (III), (III-A), (III-B), (III-C), (III-D), (III-E), (III-F), (III-G), (III-H), (III-I), (IV), (IV-A), (IV-B), (IV-C), (IV-D), (IV-E), (IV-F), (IV-G), (IV-H), and (IV-I), as set forth herein, may be independently combined with other embodiments and/or substituents of compounds of Formulas (I), (I-A), (I-B), (II), (II-A), (II-B), (II-C), (II-D), (II-E), (II-F), (II-G), (II-H), (II-I), (III), (III-A), (III-B), (III-C), (III-D), (III-E), (III-F), (III-G), (III-H), (III-I), (IV), (IV-A), (IV-B), (IV-C), (IV-D), (IV-E), (IV-F), (IV-G), (IV-H), and (IV-I), to form embodiments of the inventions not specifically set forth above. In addition, in the event that a list of substituents is listed for any particular L, $R^1$, $R^2$, $R^3$, $R^4$, $R^5$, $R^a$, W, X, $Y^1$, $Y^2$, or Z in a particular embodiment and/or claim, it is understood that each individual substituent may be deleted from the particular embodiment and/or claim and that the remaining list of substituents will be considered to be within the scope of the invention.

As one of skill in the art will appreciate, compounds of Formulas (I), (I-A), (I-B), (II), (II-A), (II-B), (II-C), (II-D), (II-E), (II-F), (II-G), (II-H), (II-I), (III), (III-A), (III-B), (III-C), (III-D), (III-E), (III-F), (III-G), (III-H), (III-I), (IV), (IV-A), (IV-B), (IV-C), (IV-D), (IV-E), (IV-F), (IV-G), (IV-H), and (IV-I) may be shown in several different ways. For example, the following compound may be shown as:

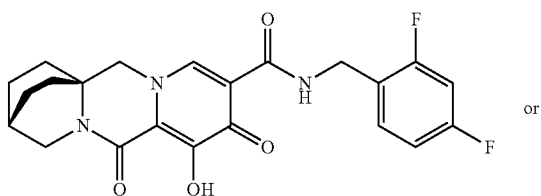

or

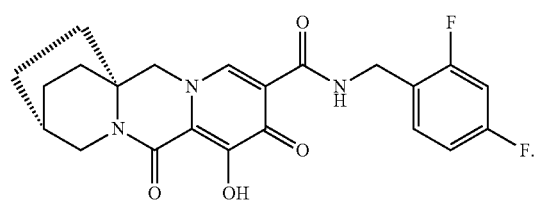

Pharmaceutical Compositions

For the purposes of administration, in certain embodiments, the compounds described herein are administered as a raw chemical or are formulated as pharmaceutical compositions. Pharmaceutical compositions of the present invention comprise a compound of Formulas (I), (I-A), (I-B), (II), (II-A), (II-B), (II-C), (II-D), (II-E), (II-F), (II-G), (II-H), (II-I), (III), (III-A), (III-B), (III-C), (III-D), (III-E), (III-F), (III-G), (III-H), (III-I), (IV), (IV-A), (IV-B), (IV-C), (IV-D), (IV-E), (IV-F), (IV-G), (IV-H), and (IV-I) I-A and a pharmaceutically acceptable carrier, diluent or excipient. The compound of Formulas (I), (I-A), (I-B), (II), (II-A), (II-B), (II-C), (II-D), (II-E), (II-F), (II-G), (II-H), (II-I), (III), (III-A), (III-B), (III-C), (III-D), (III-E), (III-F), (III-G), (III-H), (III-I), (IV), (IV-A), (IV-B), (IV-C), (IV-D), (IV-E), (IV-F), (IV-G), (IV-H), and (IV-I) I-A is present in the composition in an amount which is effective to treat a particular disease or condition of interest. The activity of compounds of Formulas (I), (I-A), (I-B), (II), (II-A), (II-B), (II-C), (II-D), (II-E), (II-F), (II-G), (II-H), (II-I), (III), (III-A), (III-B), (III-C), (III-D), (III-E), (III-F), (III-G), (III-H), (III-I), (IV), (IV-A), (IV-B), (IV-C), (IV-D), (IV-E), (IV-F), (IV-G), (IV-H), and (IV-I) I-A can be determined by one skilled in the art, for example, as described in the Examples below. Appropriate concentrations and dosages can be readily determined by one skilled in the art.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Combination Therapy

In one embodiment, a method for treating or preventing an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents. In one embodiment, a method for treating an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, one or two, or one to three) additional therapeutic agents.

In one embodiment, pharmaceutical compositions comprising a compound disclosed herein, or a pharmaceutically acceptable salt thereof, in combination with one or more (e.g., one, two, three, one or two, or one to three) additional therapeutic agents, and a pharmaceutically acceptable carrier, diluent or excipient are provided.

In one embodiment, combination pharmaceutical agents comprising a compound disclosed herein, or a pharmaceutically acceptable salt thereof, in combination with one or more (e.g., one, two, three, one or two, or one to three) additional therapeutic agents are provided.

In the above embodiments, the one or more additional therapeutic agents may be an anti-HIV agent. For example, in some embodiments, the one or more additional therapeutic agent is selected from the group consisting of HIV protease inhibitors, HIV non-nucleoside inhibitors of reverse transcriptase, HIV nucleoside or nucleotide inhibitors of reverse transcriptase, HIV integrase inhibitors, HIV non-catalytic site (or allosteric) integrase inhibitors, entry inhibitors (e.g., CCR5 inhibitors, gp41 inhibitors (i.e., fusion inhibitors) and CD4 attachment inhibitors), CXCR4 inhibitors, gp120 inhibitors, G6PD and NADH-oxidase inhibitors, compounds that target the HIV capsid ("capsid inhibitors"; e.g., capsid polymerization inhibitors or capsid disrupting compounds such as those disclosed in WO 2013/006738 (Gilead Sciences), US 2013/0165489 (University of Pennsylvania), and WO 2013/006792 (Pharma Resources), pharmacokinetic enhancers, and other drugs for treating HIV, and combinations thereof.

In some embodiments, one or more the additional therapeutic agent is selected from the group consisting of HIV protease inhibitors, HIV non-nucleoside inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In some embodiments, the one or more additional therapeutic agent is selected from the group consisting of HIV protease inhibitors, HIV non-nucleoside inhibitors of reverse transcriptase, HIV nucleoside or nucleotide inhibitors of reverse transcriptase, HIV integrase inhibitors, and combinations thereof.

In further embodiments, the one or more additional therapeutic agent is selected from one or more of:

(1) HIV protease inhibitors selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, and AG 1859;

(2) HIV non-nucleoside or non-nucleotide inhibitors of reverse transcriptase selected from the group consisting of capravirine, emivirine, delaviridine, efavirenz, nevirapine, (+) calanolide A, etravirine, GW5634, DPC-083, DPC-961, DPC-963, MIV-150, TMC-120, rilpivirene, BILR 355 BS, VRX 840773, lersivirine (UK-453061), RDEA806, KM023 and MK-1439;

(3) HIV nucleoside or nucleotide inhibitors of reverse transcriptase selected from the group consisting of zidovudine, emtricitabine, didanosine, stavudine, zalcitabine, lamivudine, abacavir, abavavir sulfate, amdoxovir, elvucitabine, alovudine, MIV-210, ±-FTC, D-d4FC, emtricitabine, phosphazide, fozivudine tidoxil, apricitibine (AVX754), KP-1461, GS-9131 (Gilead Sciences) and fosalvudine tidoxil (formerly HDP 99.0003), tenofovir, tenofovir disoproxil fumarate, tenofovir alafenamide (Gilead Sciences), tenofovir alafenamide hemifumarate (Gilead Sciences), GS-9148 (Gilead Sciences), adefovir, adefovir dipivoxil, CMX-001 (Chimerix) or CMX-157 (Chimerix);

(4) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, AR-177, L-870812, and L-870810, raltegravir, BMS-538158, GSK364735C, BMS-707035, MK-2048, BA 011, elvitegravir, dolutegravir and GSK-744;

(5) HIV non-catalytic site, or allosteric, integrase inhibitors (NCINI) including, but not limited to, BI-224436, CX0516, CX05045, CX14442, compounds disclosed in WO 2009/062285 (Boehringer Ingelheim), WO 2010/130034 (Boehringer Ingelheim), WO 2013/159064 (Gilead Sciences), WO 2012/145728 (Gilead Sciences), WO 2012/003497 (Gilead Sciences), WO 2012/003498 (Gilead Sciences) each of which is incorporated by references in its entirety herein;
(6) gp41 inhibitors selected from the group consisting of enfuvirtide, sifuvirtide, albuvirtide, FB006M, and TRI-1144;
(7) the CXCR4 inhibitor AMD-070;
(8) the entry inhibitor SP01A;
(9) the gp120 inhibitor BMS-488043;
(10) the G6PD and NADH-oxidase inhibitor immunitin;
(11) CCR5 inhibitors selected from the group consisting of aplaviroc, vicriviroc, maraviroc, cenicriviroc, PRO-140, INCB15050, PF-232798 (Pfizer), and CCR5mAb004;
(12) CD4 attachment inhibitors selected from the group consisting of ibalizumab (TMB-355) and BMS-068 (BMS-663068);
(13) pharmacokinetic enhancers selected from the group consisting of cobicistat and SPI-452; and
(14) other drugs for treating HIV selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221 HIV, DEBIO-025, BAY 50-4798, MDXO10 (ipilimumab), PBS 119, ALG 889, and PA-1050040 (PA-040), and combinations thereof.

In certain embodiments, a compound disclosed herein, or a pharmaceutically acceptable salt thereof, is combined with one, two, three, four or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The two, three, four or more additional therapeutic agents can be different therapeutic agents selected from the same class of therapeutic agents, or they can be selected from different classes of therapeutic agents. In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In a further embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In another embodiment, a compound disclosed herein, or a pharmaceutically acceptable salt thereof, is combined with two HIV nucleoside or nucleotide inhibitor of reverse transcriptase.

In a particular embodiment, a compound disclosed herein, or a pharmaceutically acceptable salt thereof, is combined with abacavir sulfate, tenofovir, tenofovir disoproxil fumarate, tenofovir alafenamide, or tenofovir alafenamide hemifumarate.

In a particular embodiment, a compound disclosed herein, or a pharmaceutically acceptable salt thereof, is combined with tenofovir, tenofovir disoproxil fumarate, tenofovir alafenamide, or tenofovir alafenamide hemifumarate.

In a particular embodiment, a compound disclosed herein, or a pharmaceutically acceptable salt thereof, is combined with a first additional therapeutic agent selected from the group consisting of: abacavir sulfate, tenofovir, tenofovir disoproxil fumarate, tenofovir alafenamide, and tenofovir alafenamide hemifumarate and a second additional therapeutic agent selected from the group consisting of emtricitibine and lamivudine.

In a particular embodiment, a compound disclosed herein, or a pharmaceutically acceptable salt thereof, is combined with a first additional therapeutic agent selected from the group consisting of: tenofovir, tenofovir disoproxil fumarate, tenofovir alafenamide, and tenofovir alafenamide hemifumarate and a second additional therapeutic agent, wherein the second additional therapeutic agent is emtricitibine.

In certain embodiments, when a compound disclosed herein is combined with one or more additional therapeutic agents as described above, the components of the composition are administered as a simultaneous or sequential regimen. When administered sequentially, the combination may be administered in two or more administrations.

In certain embodiments, a compound disclosed herein is combined with one or more additional therapeutic agents in a unitary dosage form for simultaneous administration to a patient, for example as a solid dosage form for oral administration.

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and one or more additional therapeutic agents are both present in the body of the patient.

Co-administration includes administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

The following Examples illustrate various methods of making compounds of this invention, i.e., compounds of Formula (I).

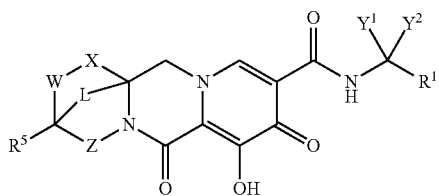

wherein L, $R^1$, $R^5$, W, X, $Y^1$, $Y^2$, and Z are as defined above. It is understood that one skilled in the art may be able to make these compounds by similar methods or by combining other methods known to one skilled in the art. It is also understood that one skilled in the art would be able to make, in a similar manner as described below, other compounds of Formulas (I), (I-A), (I-B), (II), (II-A), (II-B), (II-C), (II-D), (II-E), (II-F), (II-G), (II-H), (II-I), (III), (III-A), (III-B), (III-C), (III-D), (III-E), (III-F), (III-G), (III-H), (III-I), (IV), (IV-A), (IV-B), (IV-C), (IV-D), (IV-E), (IV-F), (IV-G), (IV-H), and (IV-I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described herein.

The following examples are provided for purposes of illustration, not limitation.

EXAMPLES

Representative Compounds

Example 1

Preparation of Compound 1

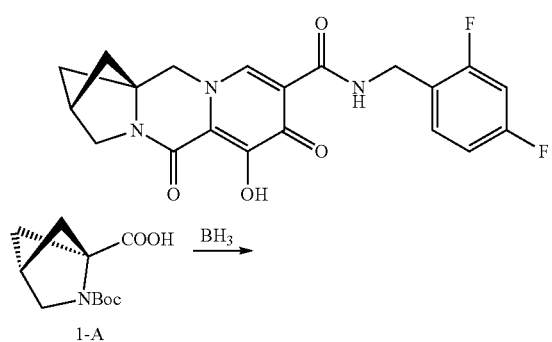

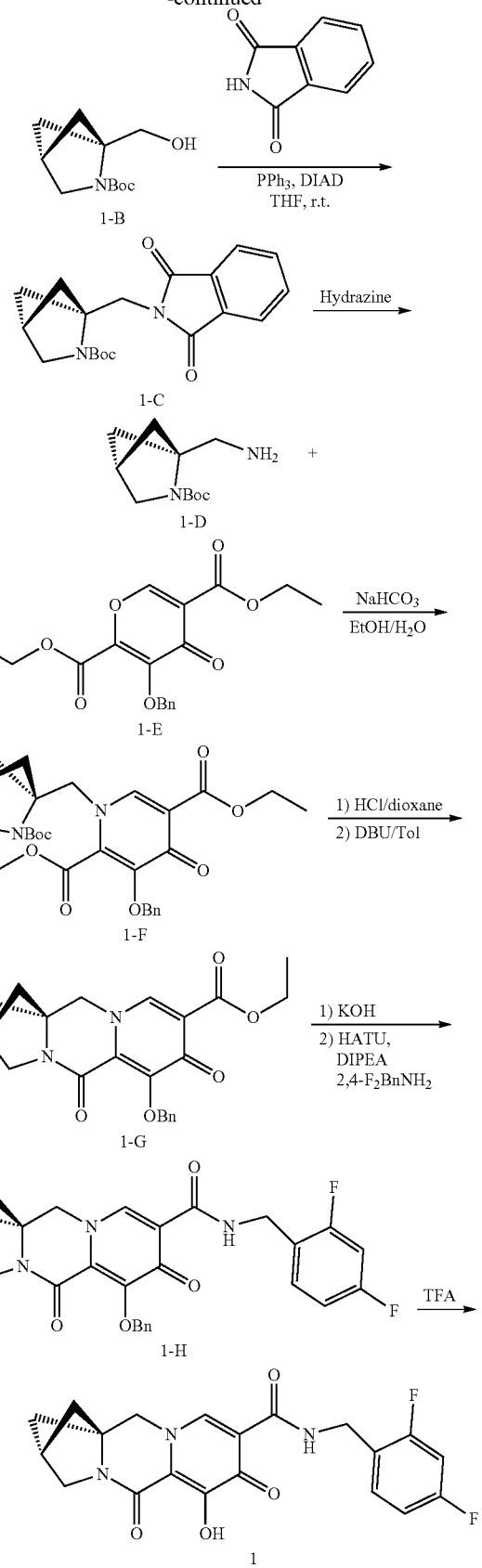

Step 1

A 100-mL 1-neck round bottom flask was charged with reactant 1-A (2.0 g, 8.8 mmol) in THF (20 mL). The reaction mixture was cooled to 0° C., and borane dimethyl sulfide (2 N in THF, 17.6 mL) was slowly added in. Then the reaction mixture was stirred at room temperature overnight. The mixture was cooled to 0° C. Methanol (8 mL) was added drop wise to quench the reaction. After concentration, the residue was purified by column chromatography on silica gel using hexanes-ethyl acetate as eluents to afford 1-B.

LCMS-ESI$^+$ (m/z): [M+H]$^+$ calculated for $C_{18}H_{19}F_2N_2O_7$: 214; found: 214.

Step 2

A 100-mL 1-neck round bottom flask was charged with reactant 1-B (1.5 g, 7.0 mmol), triphenylphosphine (4.1 g, 15.6 mmol) and phthalimide (1.7 g, 11.3 mmol) in THF (30 mL). Then the reaction mixture was cooled to 0° C. with stirring. DIAD (3.1 g, 15.6 mmol) was slowly added to the reaction mixture. The reaction mixture was stirred at room temperature overnight. After concentration, the residue was purified by column chromatography on silica gel using hexanes-ethyl acetate as eluents to afford 1-C.

LCMS-ESI$^+$ (m/z): [M+H]$^+$ calculated for $C_{18}H_{19}F_2N_2O_7$: 343; found: 343.

Step 3

To a solution of reactant 1-C (2.3 g, 6.7 mmol) in EtOH (40 mL) was added hydrazine monohydrate (1.3 mL). The reaction mixture was heated to 70° C. with stirring for 3 hours. After filtration to remove the solid, the filtrate was concentrated to afford compound 1-D.

LCMS-ESI$^+$ (m/z): [M+H]$^+$ calculated for $C_{18}H_{19}F_2N_2O_7$: 213; found: 213.

Step 4

A 100-mL 1-neck round bottom flask was charged with reactant 1-D (0.3 g, 1.4 mmol) and reactant 1-E (0.5 g, 1.4 mmol) in Ethanol (7 mL). Sodium bicarbonate (0.24 g, 2.8 mmol) in water (7 mL) was added to the reaction mixture. Then the reaction mixture was stirred at room temperature for overnight. The mixture was diluted with ethyl acetate (50 mL) and washed with water (×2). The aqueous fractions were extracted with ethyl acetate (×1), and the organic fractions were combined, dried (Na$_2$SO$_4$), and concentrated. The crude 1-F was used for next step without further purification.

LCMS-ESI$^+$ (m/z): [M+H]$^+$ calculated for $C_{18}H_{19}F_2N_2O_7$: 541; found: 541.

Step 5

A 100-mL 1-neck round bottom flask was charged with reactant 1-F (0.75 g, 1.4 mmol) in 4 N HCl in dioxane (8 mL). Then the reaction mixture was stirred at room temperature for 1 hour. After concentration, 0.65 g intermediate was obtained. The intermediate and DBU (1.0 g, 6.8 mmol) were dissolved in toluene (10 mL). The reaction mixture was heated to 110° C. with stirring for 1 hour. After concentration, the residue was purified by column chromatography on silica gel using hexanes-ethyl acetate as eluents to afford 1-G.

LCMS-ESI$^+$ (m/z): [M+H]$^+$ calculated for $C_{18}H_{19}F_2N_2O_7$: 395; found: 395.

Step 6

A 100-mL 1-neck round bottom flask was charged with reactant 1-G (0.24 g, 0.61 mmol) in THF (2 mL) and MeOH (2 mL). 1 N KOH (1.8 mL) was added to the reaction mixture. Then the reaction mixture was stirred at room temperature for 1 hour. The reaction mixture was acidified by adding 1 N HCl (1.8 mL). After concentration, the residue was co-evaporated with toluene (3×). The crude acid, 2,4-difluobenzylamine (0.17 g, 1.22 mmol), DIPEA (0.39 g, 3.04 mmol) and HATU (0.46 g, 1.22 mmol) were dissolved in DMF (10 mL). The reaction mixture was stirred at room temperature for 2 hours. The mixture was diluted with ethyl acetate (100 mL) and washed with sat NaHCO$_3$ (×2), sat NH$_4$Cl (×2) and dried (Na$_2$SO$_4$). After concentration, the crude was purified by column chromatography on silica gel with hexane-ethyl acetate to afford compound 1-H.

LCMS-ESI$^+$ (m/z): [M+H]$^+$ calculated for $C_{18}H_{19}F_2N_2O_7$: 492; found: 492.

Steps 7

A 50-mL 1-neck round bottom flask was charged with reactant 1-H (0.24 g, 0.49 mmol) in TFA (3 mL). The reaction mixture was stirred at room temperature for 30 minutes. After concentration, the crude was purified by column chromatography on silica gel with ethyl acetate-methanol to afford compound 1.

$^1$H NMR (400 MHz, Chloroform-d) δ 12.63 (s, 1H), 10.43 (s, 1H), 8.30 (s, 1H), 7.36 (d, J=10.1 Hz, 1H), 6.80 (d, J=9.0 Hz, 2H), 4.64 (d, J=5.3 Hz, 2H), 4.40 (s, 2H), 3.72 (d, J=3.7 Hz, 2H), 3.11 (d, J=4.7 Hz, 1H), 2.15 (d, J=5.4 Hz, 2H), 1.71 (d, J=4.7 Hz, 2H).

$^{19}$F NMR (376 MHz, Chloroform-d) δ −112.31-112.36 (m, 1F), −114.75 (m, 1F).

LCMS-ESI$^+$ (m/z): [M+H]$^+$ calculated for $C_{21}H_{20}F_2N_3O_5$: 402. found: 402.

Example 2

Preparation of Compound 2

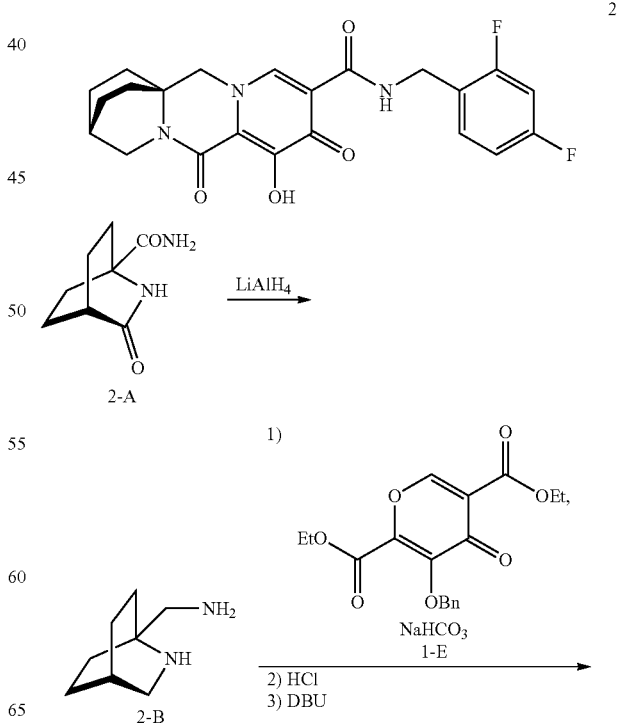

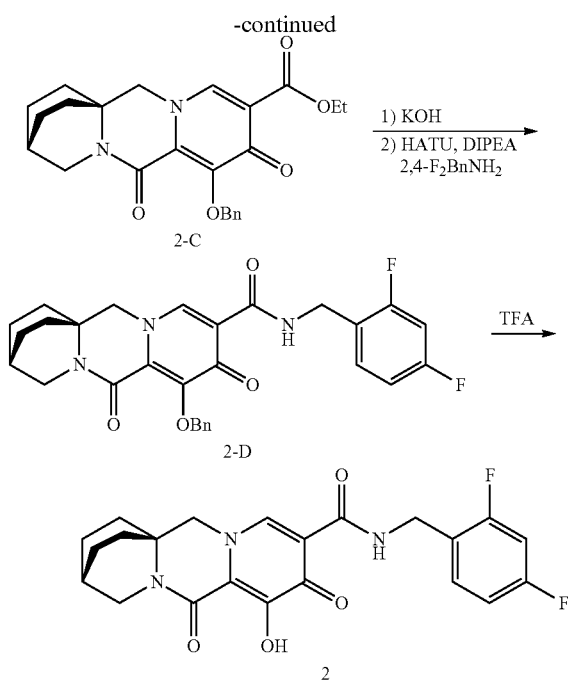

Step 1 and Step 2

To a slurry of LAH (1893 mg, 44.88 mmol) in THF (40 mL) was added compound 2-A (894 mg, 5.315 mmol) at room temperature and the resulting mixture was refluxed. After 5 hours, the mixture was cooled to 0° C. and additional LAH (1103 mg, 29.06 mmol) and THF (40 mL) were added and the resulting mixture was refluxed for 16 hours. The mixture was stirred at 0° C. as water (3 mL), 15% NaOH (3 mL), and water (9 mL) were slowly added in the sequence. After stirring for 2 hours at 0° C., the mixture was filtered and the filtrate was concentrated to a small amount, diluted with ethyl acetate, and dried (MgSO$_4$) and concentrated.

LCMS-ESI$^+$ (m/z): [M+H]$^+$ calculated for C$_8$H$_{17}$N$_2$: 141.14; found: 141.1.

The residue (crude 2-B), compound 1-E (496 mg, 1.432 mmol), and NaHCO$_3$ (326 mg, 3.881 mmol) in EtOH (~6 mL) and water (~4 mL) was stirred at room temperature for 15 hours. The mixture was concentrated, coevaporated with toluene (×2), and dried in vacuum for 30 minutes. The residue was dissolved in 4 N HCl/dioxane (10 mL) and the suspension was stirred at room temperature for 30 minutes. The resulting suspension was concentrated and dried in vacuum for 30 minutes.

To the crude residue in the above reaction, was added DBU (1 mL, 6.687 mmol) and toluene (10 mL). The resulting slurry was stirred at 110° C. bath for 1 hour. The reaction mixture was concentrated, and the residue was diluted with ethyl acetate before washing with water (×2). After the aqueous fractions were extracted with ethyl acetate (×1), the two organic fractions were combined, dried (Na$_2$SO$_4$), and concentrated. The concentrated residue was purified by column chromatography on silica gel using ethyl acetate-20% MeOH in ethyl acetate as eluent to get compound 2-C.

LCMS-ESI$^+$ (m/z): [M+H]$^+$ calculated for C$_{24}$H$_{27}$N$_2$O$_5$: 423.19; found: 423.2.

Step 3

A mixture of compound 2-C (32 mg, 0.076 mmol) in THF (1 mL) and MeOH (1 mL) was stirred at room temperature as 1 N KOH (1 mL) was added. After 15 minutes, the reaction mixture was concentrated and diluted with water before washing with ether (×1). The aqueous fraction was acidified with 1 N HCl (~1.1 mL), and extracted with CH$_2$Cl$_2$ (×2). The combined extracts were dried (Na$_2$SO$_4$) and used for the next reaction.

To the solution of the crude acid were added 2,4-difluorobenzylamine (26 mg, 0.182 mmol) and HATU (56 mg, 0.147 mmol) at room temperature followed by DIPEA (0.2 mL, 1.148 mmol). After 45 minutes at room temperature, the mixture was washed with saturated NH$_4$Cl (×1) and saturated NaHCO$_3$ (×1). After the aqueous fractions were extracted with CH$_2$Cl$_2$ (×1), the organic fractions were combined, dried (Na$_2$SO$_4$), and concentrated. The residue was purified by column chromatography on silica gel using ethyl acetate −20% MeOH/ethyl acetate as eluents to get compound 2-D.

$^1$H NMR (400 MHz, Chloroform-d) δ 10.49 (t, J=6.1 Hz, 1H), 8.31 (s, 1H), 7.60 (dt, J=6.5, 1.5 Hz, 2H), 7.44-7.27 (m, 4H), 6.87-6.75 (m, 2H), 5.28 (s, 2H), 4.64 (d, J=6.0 Hz, 2H), 3.88 (s, 2H), 3.66-3.57 (m, 2H), 2.15-2.07 (m, 1H), 1.85-1.56 (m, 8H).

$^{19}$F NMR (376 MHz, Chloroform-d) δ −112.20 (p, J=7.7 Hz), −114.73 (q, J=8.6 Hz).

LCMS-ESI$^+$ (m/z): [M+H]$^+$ calculated for C$_{29}$H$_{28}$F$_2$N$_3$O$_4$: 520.20; found: 520.2.

Step 4

Compound 2-D (26 mg, 0.050 mmol) was dissolved in TFA (2 mL) and stirred at room temperature and concentrated. The residue was purified by preparative HPLC and the collected fraction was freeze-dried to get compound 2.

$^1$H NMR (400 MHz, Chloroform-d) δ 12.60 (s, 1H), 10.48 (s, 1H), 8.26 (s, 1H), 7.36 (d, J=7.6 Hz, 1H), 6.87-6.73 (m, 2H), 4.64 (d, J=5.9 Hz, 2H), 3.90 (s, 2H), 3.69 (d, J=2.4 Hz, 2H), 2.20 (s, 1H), 2.03-1.89 (m, 2H), 1.78 (d, J=26.7 Hz, 7H).

$^{19}$F NMR (376 MHz, Chloroform-d) δ −112.36 (m, 1F), −114.73 (m, 1F).

LCMS-ESI$^+$ (m/z): [M+H]$^+$ calculated for C$_{22}$H$_{22}$F$_2$N$_3$O$_4$: 430.16; found: 430.2.

Example 3

Preparation of Compound 3

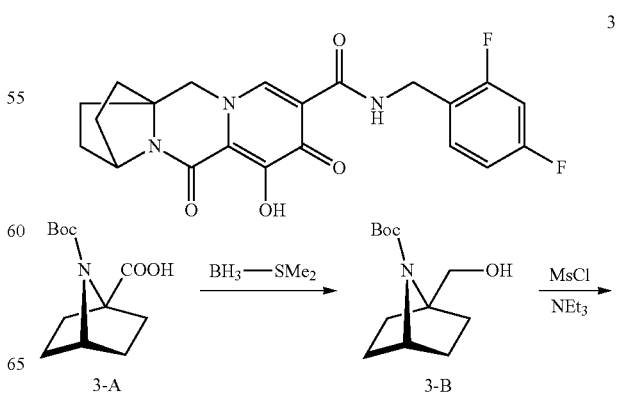

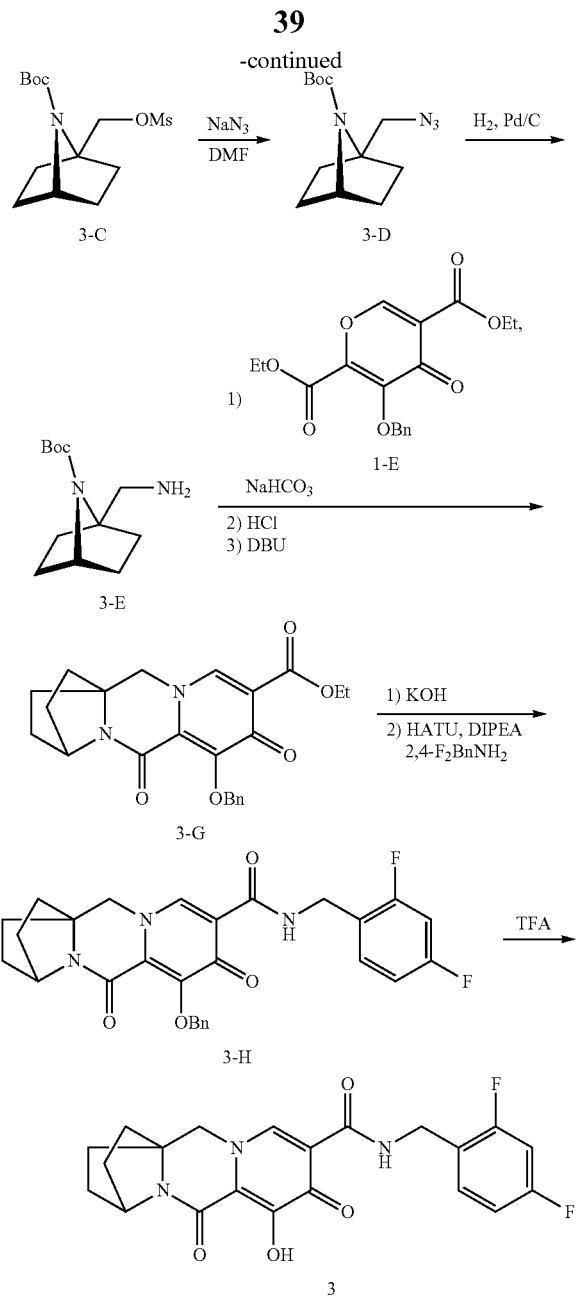

Step 1

A solution of compound 3-A (2.562 g, 10.62 mmol) in THF (26 mL) was stirred at 0° C. as 2.0 M borane dimethyl sulfide in THF (21.4 mL) was added. The reaction was stirred at room temperature. After 21 hours, the reaction mixture was cooled to 0° C. before addition of methanol to quench the reaction. The reaction mixture was concentrated and the residue was purified by column chromatography on silica gel using hexanes-ethyl acetate as eluent to get compound 3-B.

$^1$H NMR (400 MHz, Chloroform-d) δ 4.24 (t, J=4.8 Hz, 1H), 3.90 (s, 2H), 1.93-1.70 (m, 4H), 1.49-1.36 (m, 5H), 1.45 (s, 9H).

LCMS-ESI$^+$ (m/z): [M+H]$^+$ calculated for $C_{12}H_{22}NO_3$: 228.16; found: 227.8.

Step 2

A solution of compound 3-B (1106 mg, 4.866 mmol) and NEt$_3$ (0.90 mL, 6.457 mmol) in CH$_2$Cl$_2$ (11 mL) was stirred at 0° C. as MsCl (0.42 mL, 5.426 mmol) was added. After 45 minutes at 0° C., the mixture was diluted with ethyl acetate and washed with water (×2). The aqueous fractions were extracted with ethyl acetate (×1), and the organic fractions were combined, dried (Na$_2$SO$_4$), and concentrated. The residue was purified by column chromatography on silica gel using hexanes-ethyl acetate as eluents to get compound 3-C.

$^1$H NMR (400 MHz, Chloroform-d) δ 4.84 (s, 2H), 4.29 (p, J=2.4 Hz, 1H), 3.07 (s, 3H), 1.90-1.73 (m, 4H), 1.72-1.57 (m, 2H), 1.51-1.45 (m, 2H), 1.45 (s, 9H).

LCMS-ESI$^+$ (m/z): [M+H]$^+$ calculated for $C_{13}H_{24}NO_5S$: 306.14; found: 305.6.

Step 3

To a solution of compound 3-C (1398 mg, 4.578 mmol) in DMF (7 mL) was added sodium azide (1494 mg, 22.98 mmol). The mixture was stirred at 110° C. for 8 hours. The reaction mixture was diluted with 5% LiCl solution and the product was extracted with ethyl acetate (×2). After the aqueous fractions were extracted with ethyl acetate (×1), the two organic fractions were combined, dried (Na$_2$SO$_4$), and concentrated. The residue was purified by column chromatography on silica gel using hexanes-ethyl acetate as eluents to get compound 3-D.

$^1$H NMR (400 MHz, Chloroform-d) δ 4.35-4.22 (m, 1H), 3.96 (s, 2H), 1.91-1.71 (m, 4H), 1.64-1.49 (m, 2H), 1.46 (s, 9H), 1.48-1.41 (m, 2H).

Step 4

To a solution of compound 3-D (227 mg, 0.900 mmol) in EtOH (3 mL) was added 10% Pd/C (29 mg) and the mixture was stirred under H$_2$ atmosphere for 30 minutes. The mixture was filtered through celite pad and concentrated. The crude compound 3-E was used for the next reaction.

LCMS-ESI$^+$ (m/z): [M+H]$^+$ calculated for $C_{12}H_{23}N_2O_2$: 227.18; found: 226.8.

Step 5

A mixture of the crude compound 3-E, compound 1-E (328 mg, 0.947 mmol) and NaHCO$_3$ (152 mg, 1.812 mmol) in water (3 mL) and EtOH (9 mL) was stirred at room temperature for 18 hours. The mixture was concentrated to ~½ volume, diluted with water, and the product was extracted (×2). The organic fractions were washed with water (×1), combined, dried (Na$_2$SO$_4$), and concentrated. The residue was used for the next reaction.

To a solution of the above residue in CH$_2$Cl$_2$ (2 mL) was added 4 N HCl in dioxane (6 mL) at room temperature. After 2 hours, additional 4 N HCl (3 mL) was added. After 2.5 hours, the mixture was concentrated and co-evaporated with toluene (×1). The residue was used for the next reaction.

A mixture of the above residue and DBU (0.68 mL, 4.547 mmol) in toluene (10 mL) was stirred at 110° C. bath. After 3 hours at 110° C., the reaction mixture was dissolved in CH$_2$Cl$_2$ and concentrated. The residue was purified by column chromatography on silica gel using ethyl acetate-20% MeOH/ethyl acetate as eluents to get compound 3-G.

$^1$H NMR (400 MHz, Chloroform-d) δ 8.09 (s, 1H), 7.73-7.63 (m, 2H), 7.38-7.21 (m, 3H), 5.29 (s, 2H), 4.76 (t, J=4.8 Hz, 1H), 4.44-4.34 (q, J=7.2 Hz, 2H), 4.29 (s, 2H), 1.95 (m, 2H), 1.82-1.56 (m, 6H), 1.45-1.35 (t, J=7.2 Hz, 3H).

LCMS-ESI$^+$ (m/z): [M+H]$^+$ calculated for $C_{23}H_{25}N_2O_5$: 409.18; found: 409.3.

Step 6

A mixture of compound 3-G (233 mg, 0.570 mmol) in THF (3 mL) and MeOH (3 mL) was stirred at room temperature as 1 N KOH (3 mL) was added. After 30 minutes at room temperature, the reaction mixture was concentrated and diluted with water before washing with ether (×1). The aqueous fraction was acidified with 1 N HCl (~3.3 mL), and extracted with ethyl acetate (×2). The extracts were washed with brine (×1), combined, dried (Na$_2$SO$_4$), and concentrated to get 207 mg (95%) of the crude acid. The crude acid was used for the next reaction.

A mixture of the crude acid (207 mg, 0.544 mmol), 2,4-difluorobenzylamine (100 mg, 0.699 mmol), and HATU (259 mg, 0.681 mmol) in CH$_2$Cl$_2$ (5 mL) was stirred at room temperature as DIPEA (0.68 mL, 3.904 mmol) was added. After 45 minutes, the mixture was diluted with ethyl acetate, washed with saturated NH$_4$Cl (×1) and saturated NaHCO$_3$ (×1). After the aqueous fractions were extracted with ethyl acetate (×1), the organic fractions were combined, dried (Na$_2$SO$_4$), and concentrated. The residue was purified by column chromatography on silica gel using ethyl acetate-20% MeOH/ethyl acetate as eluents to get compound 3-H.

$^1$H NMR (400 MHz, Chloroform-d) δ 10.41 (s, 1H), 8.40 (s, 1H), 7.63-7.57 (m, 2H), 7.41-7.27 (m, 4H), 6.87-6.76 (m, 2H), 5.27 (s, 2H), 4.81 (t, J=4.8 Hz, 1H), 4.64 (d, J=5.8 Hz, 2H), 4.37 (s, 2H), 2.03-1.92 (m, 2H), 1.86-1.75 (m, 2H), 1.74-1.62 (m, 4H).

$^{19}$F NMR (376 MHz, Chloroform-d) δ −112.16 (q, J=8.0 Hz, 1F), −114.71 (q, J=8.5 Hz, 1F).

LCMS-ESI$^+$ (m/z): [M+H]$^+$ calculated for C$_{28}$H$_{26}$F$_2$N$_3$O$_4$: 506.19; found: 506.2.

Step 7

Compound 3-H (246 mg, 0.487 mmol) was dissolved and stirred in TFA (5 mL) at room temperature. After 30 minutes, the solution was concentrated and the residue was purified by column chromatography on silica gel using CH$_2$Cl$_2$-20% MeOH in CH$_2$Cl$_2$ as eluents. The collected fractions were concentrated and the residue was dissolved in MeCN (1 mL) at room temperature and diluted with MeOH (4 mL) which made solids. The resulting mixture was stored in 0° C. bath for 20 minutes and the solids were filtered, washed with MeOH, and dried in vacuum to get compound 3.

$^1$H NMR (400 MHz, Chloroform-d) δ 12.58 (s, 1H), 10.43 (s, 1H), 8.36 (s, 1H), 7.44-7.30 (m, 1H), 6.90-6.72 (m, 2H), 4.82 (t, J=4.7 Hz, 1H), 4.71-4.59 (d, J=5.6 Hz, 2H), 4.39 (s, 2H), 2.06-2.01 (m, 2H), 1.91-1.84 (m, 2H), 1.81-1.71 (m, 4H).

$^{19}$F NMR (376 MHz, Chloroform-d) δ −112.34 (m, 1F), −114.73 (m, 1F).

LCMS-ESI$^+$ (m/z): [M+H]$^+$ calculated for C$_{21}$H$_{19}$F$_2$N$_3$O$_4$: 416.14; found: 416.20.

Example 4

Preparation of Compound 4

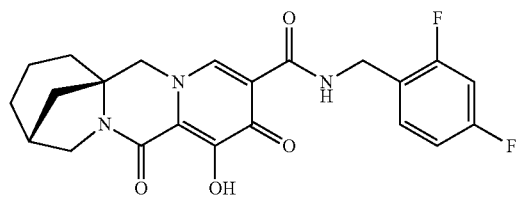

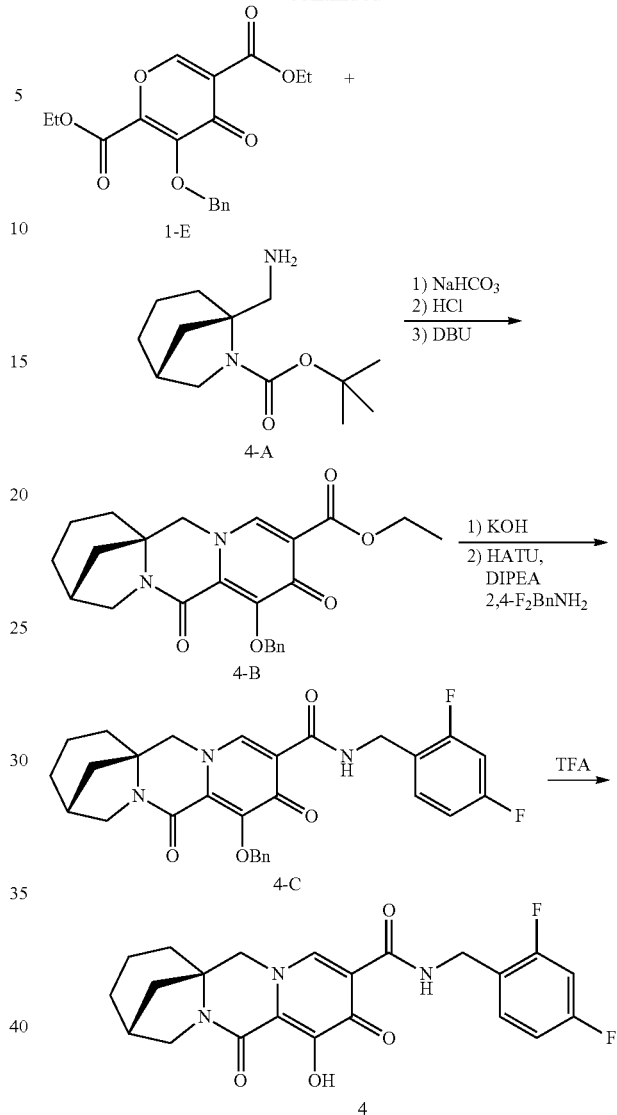

Step 1

The mixture of compound 1-E (320 mg, 0.924 mmol), compound 4-A (*Tetrahedron: Asymmetry* 2006, 17, 252-258; 220 mg, 0.915 mmol), and NaHCO$_3$ (156 mg, 1.857 mmol) in water (3 mL) and EtOH (3 mL) was stirred at room temperature. After 2 hours, the reaction mixture was diluted with water and extracted with ethyl acetate (twice). After the extracts were washed with water, the organic fractions were combined, dried (Na$_2$SO$_4$), and concentrated. The residue was dried under vacuum and used for the next reaction.

To a solution of the residue in CH$_2$Cl$_2$ (2 mL) was added 4 N HCl in dioxane (4 mL) at room temperature. After 1.5 hours, the solution was concentrated and dried under vacuum for 1 hour. A suspension of the residue and DBU (0.55 mL, 3.678 mmol) in toluene (5 mL) was stirred at 110° C. bath for 30 min. After the mixture was concentrated, the residue was purified by column chromatography on silica gel using ethyl acetate-20% MeOH/ethyl acetate as eluents to obtain compound 4-B.

$^1$H NMR (400 MHz, Chloroform-d) δ 8.06 (s, 1H), 7.71-7.63 (m, 2H), 7.33 (ddt, J=8.0, 6.6, 1.1 Hz, 2H), 7.30-7.26 (m, 1H), 5.54 (d, J=9.9 Hz, 1H), 5.18 (d, J=9.9 Hz, 1H), 4.40 (qd, J=7.1, 2.3 Hz, 2H), 4.03-3.92 (m, 2H), 3.78-3.67 (m, 1H), 3.52 (d, J=12.2 Hz, 1H), 2.66 (d, J=5.1 Hz, 1H), 1.82 (d, J=2.6 Hz, 2H), 1.75-1.43 (m, 6H), 1.40 (t, J=7.1 Hz, 3H).

LCMS-ESI⁺ (m/z): [M+H]⁺ calculated for $C_{24}H_{27}N_2O_5$: 423.19; found: 423.3.

Step 2

A mixture of compound 4-B (70 mg, 0.166 mmol) in THF (2 mL) and MeOH (2 mL) was stirred at room temperature as 1 N KOH (0.35 mL) was added. After 2.25 hours, the reaction mixture was concentrated, acidified with 1 N HCl (~0.4 mL), and diluted with brine before extraction with $CH_2Cl_2$ (thrice). The combined extracts was dried ($Na_2SO_4$) and concentrated. The residual crude acid was used for the next reaction.

A mixture of the crude acid, 2,4-difluorobenzylamine (33 mg, 0.231 mmol), and HATU (93 mg, 0.245 mmol) in $CH_2Cl_2$ (3 mL) was stirred at room temperature as DIPEA (0.20 mL, 1.148 mmol) was added. After ~30 min, the reaction mixture was diluted with ethyl acetate, and washed with saturated $NH_4Cl$, water, saturated $NaHCO_3$, and brine. After the aqueous fractions were extracted with ethyl acetate, the two organic fractions were combined, dried ($Na_2SO_4$) and concentrated. The residue was purified by column chromatography on silica gel using ethyl acetate-20% MeOH/ethyl acetate as eluents to obtain compound 4-C.

¹H NMR (400 MHz, Chloroform-d) δ 10.61-10.40 (m, 1H), 8.37 (s, 1H), 7.66-7.54 (m, 2H), 7.44-7.22 (m, 4H), 6.89-6.74 (m, 2H), 5.42 (d, J=10.0 Hz, 1H), 5.20 (d, J=9.9 Hz, 1H), 4.73-4.54 (m, 2H), 4.11-3.97 (m, 2H), 3.72 (dd, J=12.4, 5.4 Hz, 1H), 3.51 (d, J=12.3 Hz, 1H), 2.65 (dt, J=5.7, 3.1 Hz, 1H), 1.88-1.77 (m, 2H), 1.77-1.31 (m, 6H).

¹⁹F NMR (376 MHz, Chloroform-d) δ −112.19 (p, J=8.0 Hz, 1F), −114.73 (q, J=8.5 Hz, 1F).

LCMS-ESI⁺ (m/z): [M+H]⁺ calculated for $C_{29}H_{28}F_2N_3O_4$: 520.20; found: 520.3.

Step 3

Compound 4-C (76 mg, 0.146 mmol) was dissolved in TFA (1 mL) and stirred at room temperature. After 30 min, the solution was concentrated and the residue was purified by column chromatography on silica gel using $CH_2Cl_2$-20% MeOH in $CH_2Cl_2$ as eluents to obtain compound 4.

¹H NMR (400 MHz, Chloroform-d) δ 10.50 (t, J=6.0 Hz, 1H), 8.39 (s, 1H), 7.34 (td, J=8.7, 6.5 Hz, 1H), 6.86-6.71 (m, 2H), 4.68-4.53 (m, 2H), 4.20 (d, J=12.8 Hz, 1H), 4.06 (d, J=12.8 Hz, 1H), 3.73-3.56 (m, 2H), 2.72 (t, J=3.9 Hz, 1H), 1.99-1.82 (m, 2H), 1.83-1.67 (m, 3H), 1.62 (td, J=12.7, 4.5 Hz, 1H), 1.56-1.39 (m, 2H).

¹⁹F NMR (376 MHz, Chloroform-d) δ −112.16 (p, J=7.7 Hz, 1F), −114.77 (q, J=8.5 Hz, 1F).

LCMS-ESI⁺ (m/z): [M+H]⁺ calculated for $C_{22}H_{22}F_2N_3O_4$: 430.16; found: 430.3.

Example 5

Preparation of Compound 5

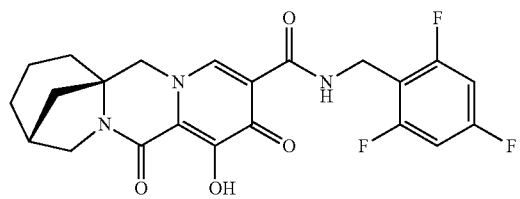

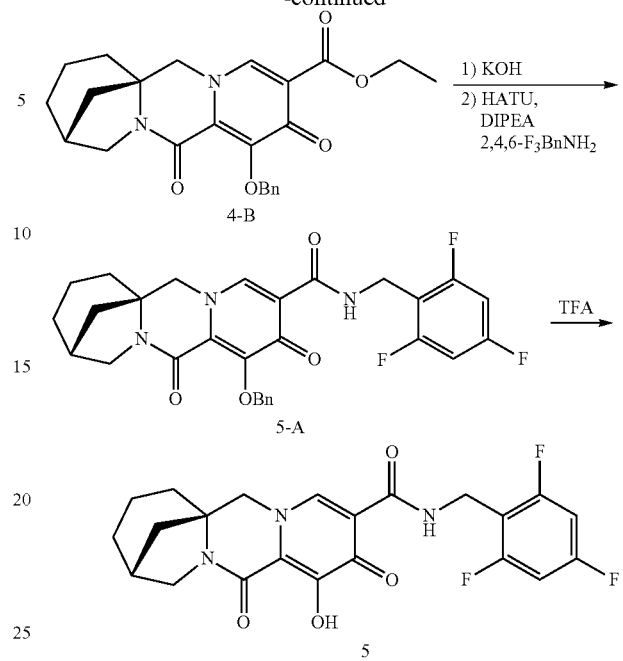

Step 1

A mixture of compound 4-B (70 mg, 0.166 mmol) in THF (2 mL) and MeOH (2 mL) was stirred at room temperature as 1 N KOH (0.35 mL) was added. After 2.25 hours, the reaction mixture was concentrated, acidified with 1 N HCl (~0.4 mL), and diluted with brine before extraction with $CH_2Cl_2$ (thrice). The combined extracts was dried ($Na_2SO_4$) and concentrated. The residual crude acid was used for the next reaction.

A mixture of the crude acid, 2,4,6-trifluorobenzylamine (41 mg, 0.254 mmol), and HATU (97 mg, 0.255 mmol) in $CH_2Cl_2$ (3 mL) was stirred at room temperature as DIPEA (0.20 mL, 1.148 mmol) was added. After ~30 min, the reaction mixture was diluted with ethyl acetate, and washed with saturated $NH_4Cl$, water, saturated $NaHCO_3$, and brine. After the aqueous fractions were extracted with ethyl acetate, two organic fractions were combined, dried ($Na_2SO_4$) and concentrated. The residue was purified by column chromatography on silica gel using ethyl acetate-20% MeOH/ethyl acetate as eluents to obtain compound 5-A.

¹H NMR (400 MHz, Chloroform-d) δ 10.40 (t, J=5.7 Hz, 1H), 8.35 (s, 1H), 7.64-7.53 (m, 2H), 7.35-7.23 (m, 3H), 6.74-6.57 (m, 2H), 5.41 (d, J=10.0 Hz, 1H), 5.19 (d, J=10.0 Hz, 1H), 4.76-4.54 (m, 2H), 4.03 (d, J=2.5 Hz, 2H), 3.76-3.63 (m, 1H), 3.50 (d, J=12.3 Hz, 1H), 2.64 (dq, J=5.0, 2.4 Hz, 1H), 1.87-1.76 (m, 2H), 1.76-1.30 (m, 6H).

¹⁹F NMR (376 MHz, Chloroform-d) δ −109.10 (tt, J=8.8, 6.3 Hz, 1F), −111.87 (t, J=7.0 Hz, 2F).

LCMS-ESI⁺ (m/z): [M+H]⁺ calculated for $C_{29}H_{27}F_3N_3O_4$: 538.20; found: 538.3.

Step 2

Compound 5-A (78 mg, 0.145 mmol) was dissolved in TFA (1 mL) and stirred at room temperature. After 30 min, the solution was concentrated and the residue was purified by column chromatography on silica gel using $CH_2Cl_2$-20% MeOH in $CH_2Cl_2$ as eluents to obtain compound 5.

¹H NMR (400 MHz, Chloroform-d) δ 10.42 (s, 1H), 8.31 (s, 1H), 6.65 (dd, J=8.7, 7.5 Hz, 2H), 4.66 (d, J=5.8 Hz, 2H), 4.13-3.96 (m, 2H), 3.72-3.60 (m, 2H), 2.73 (d, J=4.9 Hz, 1H), 1.92 (s, 2H), 1.84-1.41 (m, 6H).

$^{19}$F NMR (376 MHz, Chloroform-d) δ −109.18 (tt, J=8.7, 6.3 Hz, 1F), −111.98 (t, J=6.9 Hz, 2F).

LCMS-ESI$^+$ (m/z): [M+H]$^+$ calculated for $C_{22}H_{21}F_3N_3O_4$: 448.15; found: 448.3.

Example 6

Preparation of Compound 6

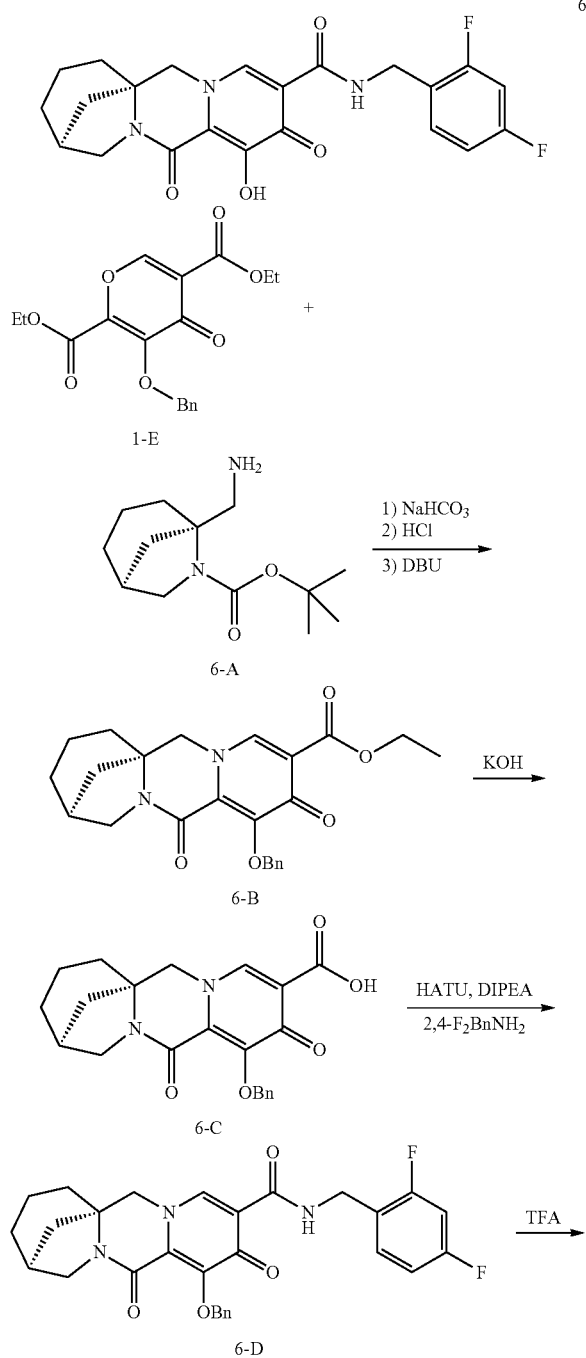

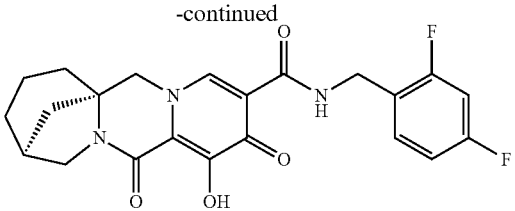

Step 1

The mixture of compound 1-E (970 mg, 2.801 mmol), compound 6-A (*Tetrahedron: Asymmetry* 2006, 17, 252-258; 778 mg, 2.811 mmol), and NaHCO$_3$ (472 mg, 1.857 mmol) in water (5 mL) and EtOH (5 mL) was stirred at room temperature. After 2 hours, the reaction mixture was diluted with water and extracted with ethyl acetate (twice). After the extracts were washed with water, the organic fractions were combined, dried (Na$_2$SO$_4$), and concentrated. The residue was dried under vacuum and used for the next reaction.

To a solution of the residue in CH$_2$Cl$_2$ (3 mL) was added 4 N HCl in dioxane (7 mL) at room temperature. After 2 hours, the solution was concentrated and co-evaporated with toluene (×1). A suspension of the residue and DBU (1.75 mL, 11.70 mmol) in toluene (17.5 mL) was stirred at 110° C. bath for 1 hour. After the mixture was concentrated, the residue was purified by column chromatography on silica gel using ethyl acetate-20% MeOH/ethyl acetate as eluents to obtain compound 6-B.

$^1$H NMR (400 MHz, Chloroform-d) δ 8.07 (s, 1H), 7.71-7.64 (m, 2H), 7.37-7.27 (m, 3H), 5.54 (d, J=9.9 Hz, 1H), 5.18 (d, J=9.9 Hz, 1H), 4.41 (qd, J=7.2, 2.4 Hz, 2H), 3.98 (d, J=1.3 Hz, 2H), 3.73 (dd, J=12.1, 5.6 Hz, 1H), 3.52 (d, J=12.3 Hz, 1H), 2.65 (s, 1H), 1.82 (d, J=2.7 Hz, 2H), 1.75-1.43 (m, 6H), 1.40 (t, J=7.1 Hz, 3H).

LCMS-ESI$^+$ (m/z): [M+H]$^+$ calculated for $C_{24}H_{27}N_2O_5$: 423.19; found: 423.3.

Step 2 and Step 3

A mixture of compound 6-B (962 mg, 2.277 mmol) in THF (5 mL) and MeOH (5 mL) was stirred at room temperature as 1 N KOH (4.85 mL) was added. After 1 hour, the reaction mixture was concentrated to ~5 mL, acidified with 1 N HCl (~5 mL), and diluted with brine before extraction with CH$_2$Cl$_2$ (50 mL×2). The combined extracts was dried (Na$_2$SO$_4$) and concentrated to provide compound 6-C.

A mixture of compound 6-C (102 mg, 0.259 mmol), 2,4-difluorobenzylamine (58 mg, 0.405 mmol), and HATU (152 mg, 0.400 mmol) in CH$_2$Cl$_2$ (5 mL) was stirred at room temperature as DIPEA (0.35 mL, 2.009 mmol) was added. After 1 hour, the reaction mixture was diluted with ethyl acetate, and washed with saturated NH$_4$Cl, water, saturated NaHCO$_3$, and brine. After the aqueous fractions were extracted with ethyl acetate, two organic fractions were combined, dried (Na$_2$SO$_4$) and concentrated. The residue was purified by column chromatography on silica gel using ethyl acetate-20% MeOH/ethyl acetate as eluents to obtain compound 6-D.

$^1$H NMR (400 MHz, Chloroform-d) δ 10.50 (t, J=6.0 Hz, 1H), 8.38 (s, 1H), 7.66-7.52 (m, 2H), 7.42-7.20 (m, 4H), 6.90-6.72 (m, 2H), 5.41 (d, J=10.0 Hz, 1H), 5.20 (d, J=10.0 Hz, 1H), 4.74-4.53 (m, 2H), 4.05 (q, J=12.9 Hz, 2H), 3.71 (dd, J=12.3, 5.4 Hz, 1H), 3.50 (d, J=12.3 Hz, 1H), 2.64 (dt, J=5.7, 2.9 Hz, 1H), 1.86-1.78 (m, 2H), 1.78-1.30 (m, 6H).

$^{19}$F NMR (376 MHz, Chloroform-d) δ −112.20 (p, J=7.6 Hz, 1F), −114.76 (q, J=8.6 Hz, 1F).

LCMS-ESI$^+$ (m/z): [M+H]$^+$ calculated for $C_{29}H_{28}F_2N_3O_4$: 520.20; found: 520.3.

Step 4

Compound 6-D (122 mg, 0.235 mmol) was dissolved in TFA (1.5 mL) and stirred at room temperature. After 30 min, the solution was concentrated and the residue was dissolved in $CH_2Cl_2$ before washing with 0.1 N HCl. After the aqueous fraction was extracted with $CH_2Cl_2$ (twice), the organic fractions were combined, dried ($Na_2SO_4$), and concentrated. The residue was purified by column chromatography on silica gel using $CH_2Cl_2$-20% MeOH in $CH_2Cl_2$ as eluents to obtain compound 6.

$^1$H NMR (400 MHz, Chloroform-d) δ 12.16 (s, 1H), 10.46 (s, 1H), 8.30 (s, 1H), 7.36 (td, J=8.7, 6.3 Hz, 1H), 6.88-6.70 (m, 2H), 4.64 (d, J=6.0 Hz, 2H), 4.06 (q, J=12.8 Hz, 2H), 3.75-3.62 (m, 2H), 2.74 (s, 1H), 1.93 (d, J=2.6 Hz, 2H), 1.87-1.70 (m, 3H), 1.70-1.42 (m, 3H).

$^{19}$F NMR (376 MHz, Chloroform-d) δ −112.40 (p, J=7.7 Hz, 1F), −114.76 (q, J=8.6 Hz, 1F).

LCMS-ESI$^+$ (m/z): [M+H]$^+$ calculated for $C_{22}H_{22}F_2N_3O_4$: 430.16; found: 430.2.

Example 7

Preparation of Compound 7

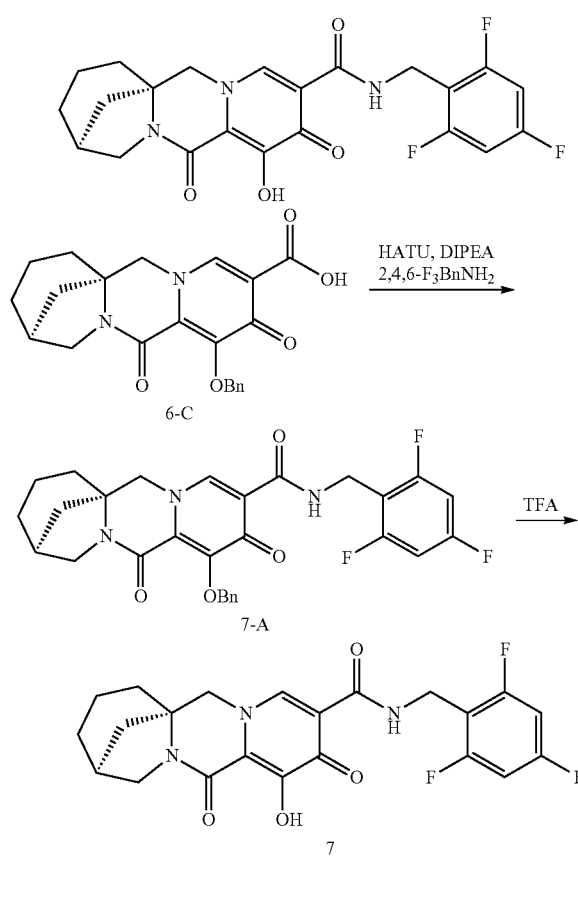

Step 1

A mixture of compound 6-C (266 mg, 0.674 mmol), 2,4,6-trifluorobenzylamine (150 mg, 0.931 mmol), and HATU (390 mg, 1.026 mmol) in $CH_2Cl_2$ (10 mL) was stirred at room temperature as DIPEA (0.82 mL, 4.708 mmol) was added. After 1 hour, the reaction mixture was diluted with ethyl acetate, and washed with saturated $NH_4Cl$, water, saturated $NaHCO_3$, and water. After the aqueous fractions were extracted with ethyl acetate, two organic fractions were combined, dried ($Na_2SO_4$) and concentrated. The residue was purified by column chromatography on silica gel using ethyl acetate-20% MeOH/ethyl acetate as eluents to obtain compound 7-A.

$^1$H NMR (400 MHz, Chloroform-d) δ 10.40 (t, J=5.9 Hz, 1H), 8.34 (s, 1H), 7.65-7.51 (m, 2H), 7.38-7.20 (m, 3H), 6.74-6.58 (m, 2H), 5.41 (d, J=10.0 Hz, 1H), 5.18 (d, J=10.0 Hz, 1H), 4.66 (qd, J=14.5, 5.8 Hz, 2H), 4.03 (s, 2H), 3.71 (dd, J=12.4, 5.5 Hz, 1H), 3.50 (d, J=12.3 Hz, 1H), 2.64 (dt, J=6.0, 3.2 Hz, 1H), 1.88-1.77 (m, 2H), 1.77-1.51 (m, 3H), 1.40 (m, 3H).

$^{19}$F NMR (376 MHz, Chloroform-d) δ −109.12 (ddd, J=15.2, 8.9, 6.4 Hz, 1F), −111.87 (t, J=7.0 Hz, 2F).

LCMS-ESI$^+$ (m/z): [M+H]$^+$ calculated for $C_{29}H_{27}F_3N_3O_4$: 538.20; found: 538.3.

Step 2

Compound 7-A (266 mg, 0.495 mmol) was dissolved in TFA (3 mL) and stirred at room temperature. After 20 min, the solution was concentrated and the residue was dissolved in $CH_2Cl_2$ before washing with 0.1 N HCl. After the aqueous fraction was extracted with $CH_2Cl_2$ (twice), the organic fractions were combined, dried ($Na_2SO_4$), and concentrated. The residue was purified by column chromatography on silica gel using $CH_2Cl_2$-20% MeOH in $CH_2Cl_2$ as eluents to obtain compound 7. The obtained product was further purified by trituration in methanol (1.5 mL) at room temperature for 1 hour and then 0° C. for 1 hour. The solids were filtered, washed with methanol, and dried under vacuum overnight.

$^1$H NMR (400 MHz, Chloroform-d) δ 12.11 (s, 1H), 10.39 (t, J=5.9 Hz, 1H), 8.28 (s, 1H), 6.74-6.57 (m, 2H), 4.73-4.58 (m, 2H), 4.12-3.97 (m, 2H), 3.73-3.61 (m, 2H), 2.73 (s, 1H), 1.98-1.85 (m, 2H), 1.85-1.69 (m, 3H), 1.69-1.42 (m, 3H).

$^{19}$F NMR (376 MHz, Chloroform-d) δ −109.26 (tt, J=8.9, 6.3 Hz, 1F), −111.99 (t, J=6.9 Hz, 2F).

LCMS-ESI$^+$ (m/z): [M+H]$^+$ calculated for $C_{22}H_{21}F_3N_3O_4$: 448.15; found: 448.3.

Example 8

Preparation of Compound 8

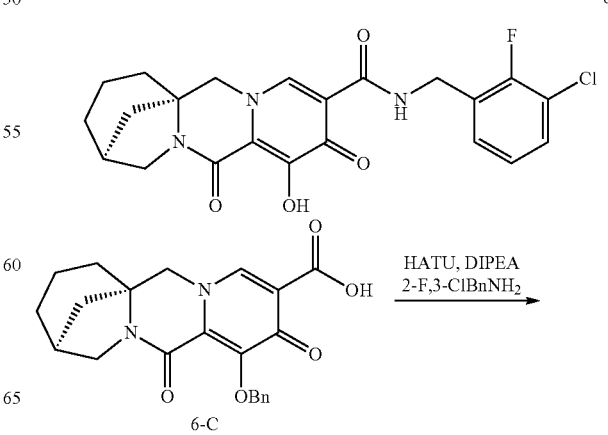

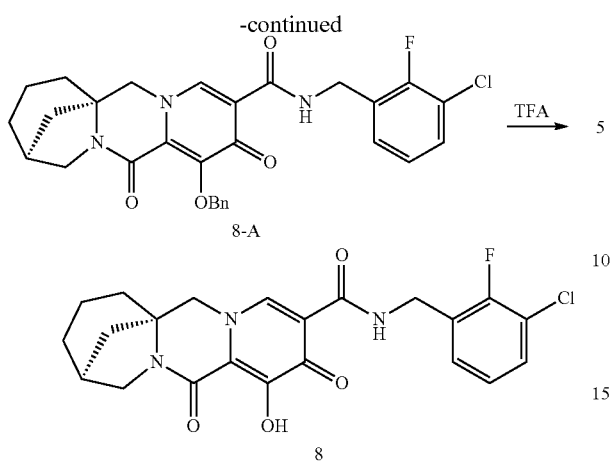

8-A

8

Step 1

A mixture of compound 6-C (151 mg, 0.383 mmol), 3-chloro-2-fluorobenzylamine (91 mg, 0.570 mmol), and HATU (239 mg, 0.629 mmol) in $CH_2Cl_2$ (5 mL) was stirred at room temperature as DIPEA (0.5 mL, 2.871 mmol) was added. After 1 hour, the reaction mixture was diluted with ethyl acetate, and washed with saturated $NH_4Cl$ (twice), saturated $NaHCO_3$ (twice), and water. After the aqueous fractions were extracted with ethyl acetate, the two organic fractions were combined, dried ($Na_2SO_4$) and concentrated. The residue was purified by column chromatography on silica gel using ethyl acetate-20% MeOH/ethyl acetate as eluents to obtain compound 8-A.

$^1$H NMR (400 MHz, Chloroform-d) δ 10.57 (t, J=6.1 Hz, 1H), 8.40 (s, 1H), 7.67-7.51 (m, 2H), 7.41-7.15 (m, 5H), 7.03 (td, J=7.9, 1.2 Hz, 1H), 5.42 (d, J=10.0 Hz, 1H), 5.20 (d, J=10.0 Hz, 1H), 4.80-4.56 (m, 2H), 4.16-4.06 (m, 2H), 4.01 (d, J=12.8 Hz, 1H), 3.71 (dd, J=12.4, 5.3 Hz, 1H), 3.51 (d, J=12.3 Hz, 1H), 2.64 (s, 1H), 1.74-1.29 (m, 7H).

$^{19}$F NMR (376 MHz, Chloroform-d) δ -120.95 (t, J=6.9 Hz).

LCMS-ESI$^+$ (m/z): [M+H]$^+$ calculated for $C_{29}H_{28}ClFN_3O_4$: 536.18; found: 536.2.

Step 2

Compound 8-A (73 mg, 0.136 mmol) was dissolved in TFA (3 mL) and stirred at room temperature. After 1 hour, the solution was concentrated and the residue was dissolved in $CH_2Cl_2$ before washing with 0.1 N HCl. After the aqueous fraction was extracted with $CH_2Cl_2$ (twice), the organic fractions were combined, dried ($Na_2SO_4$), and concentrated. The residue was purified by column chromatography on silica gel using $CH_2Cl_2$-20% MeOH in $CH_2Cl_2$ as eluents to obtain compound 8. The obtained product was further purified by trituration in methanol (1 mL) at 0° C. for 1 hour. The solids were filtered, washed with methanol, and dried in vacuum overnight.

$^1$H NMR (400 MHz, Chloroform-d) δ 12.18 (s, 1H), 10.51 (s, 1H), 8.31 (s, 1H), 7.32-7.26 (m, 2H), 7.06-6.98 (m, 1H), 4.71 (d, J=5.3 Hz, 2H), 4.16-3.97 (m, 2H), 3.67 (d, J=5.0 Hz, 2H), 2.74 (d, J=4.9 Hz, 1H), 1.93 (d, J=2.5 Hz, 2H), 1.87-1.70 (m, 3H), 1.70-1.58 (m, 1H), 1.58-1.43 (m, 2H).

$^{19}$F NMR (376 MHz, Chloroform-d) δ -120.94 (s).

LCMS-ESI$^+$ (m/z): [M+H]$^+$ calculated for $C_{22}H_{22}ClFN_3O_4$: 446.13; found: 446.3.

Example 9

Preparation of Compound 9

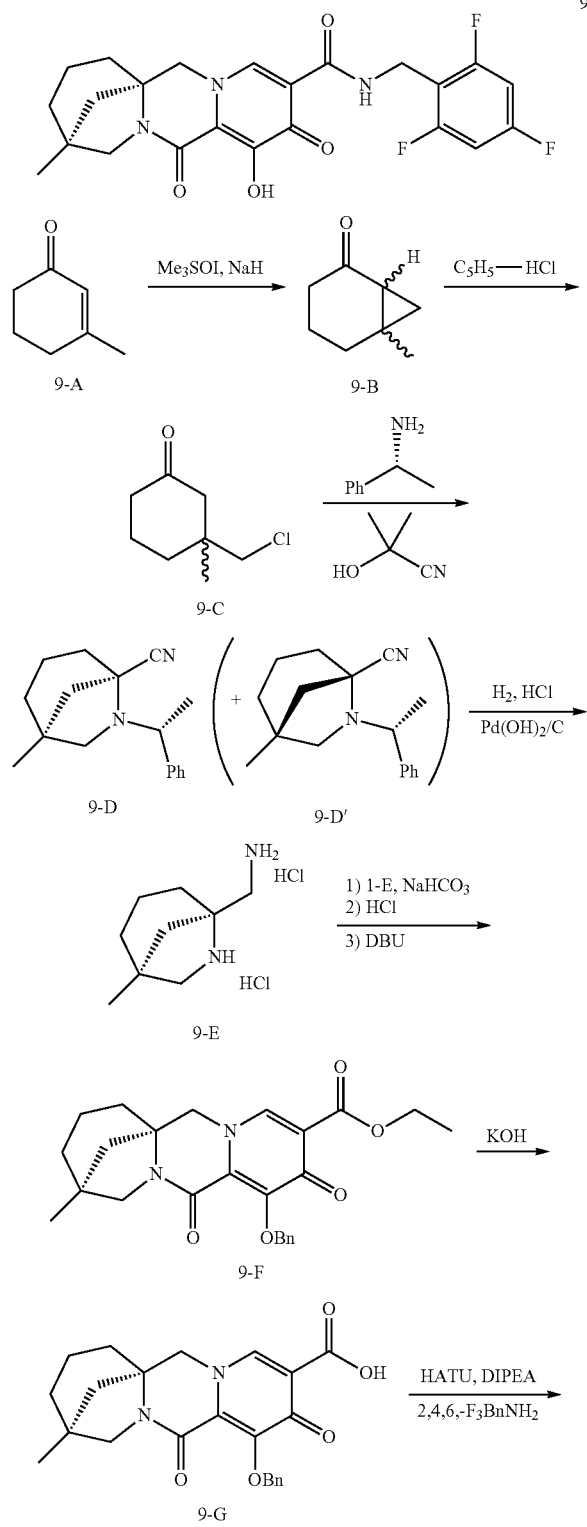

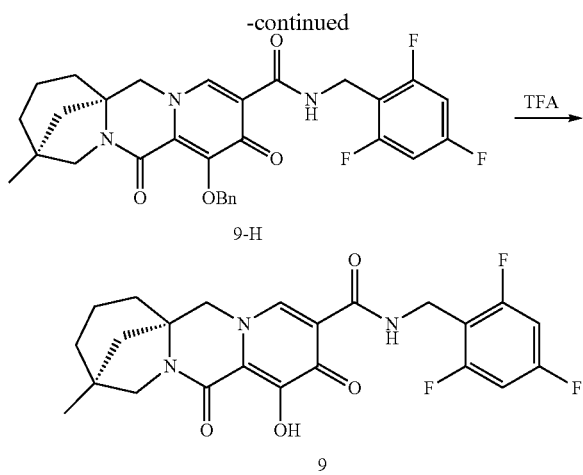

Step 1

A flask containing DMSO (22 mL) was stirred in a water bath (−18° C.) as small portions of NaH (60%, 1.235 g, 30.88 mmol) was added slowly while the inner temperature of the mixture was maintained below 20° C. After addition, Me₃SOI (6.79 g, 30.85 mmol) was added portionwise while the temperature was kept below 20° C. After addition, the mixture was stirred at the water bath (~16-18° C.) for 45 min. To the mixture was added a solution of compound 9-A (3.15 mL, 27.77 mmol) in DMSO (3.95 mL) dropwise. The resulting mixture was stirred at room temperature for 30 min and then at 50° C. for 2 hours. The reaction mixture was poured to ~60 g of ice and the resulting mixture was transferred to a separatory funnel before the product was extracted with ether (~50-70 mL twice). The extracts were washed with water, combined, dried (MgSO₄), and concentrated. The residue was purified by column chromatography on silica gel using hexanes-ethyl acetate as eluents. Collected fractions were concentrated to a small volume at ~20° C. bath by rotorvap to provide compound 9-B.

$^1$H NMR (400 MHz, Chloroform-d) δ 2.35-2.23 (m, 1H), 2.08-1.89 (m, 2H), 1.78-1.66 (m, 2H), 1.60 (qd, J=8.7, 7.8, 4.8 Hz, 2H), 1.40 (t, J=4.8 Hz, 1H), 1.21 (s, 3H), 0.91 (dd, J=10.0, 5.1 Hz, 1H).

Step 2

A mixture of compound 9-B (3.824 g, 54% purity, 16.57 mmol) and pyridine HCl (7.680 g, 66.46 mmol) in acetonitrile (40 mL) was refluxed at 90° C. for 24 hours. The reaction mixture was diluted with water (150 mL) and the product was extracted with ether (~80 mL×3). The extracts were washed with water, combined, dried (MgSO₄), and concentrated. The residue was purified by column chromatography on silica gel using hexanes-ethyl acetate as eluents. Product containing fractions were combined and concentrated by rotorvap to provide compound 9-C.

$^1$H NMR (400 MHz, Chloroform-d) δ 3.38 (s, 2H), 2.39 (d, J=13.9 Hz, 1H), 2.30 (dddd, J=14.7, 13.4, 7.8, 4.7 Hz, 2H), 2.17 (dt, J=13.8, 1.7 Hz, 1H), 2.01-1.79 (m, 3H), 1.58 (dd, J=10.0, 5.1 Hz, 1H), 1.03 (s, 3H).

Step 3

A solution of gamma-chloroketone compound 9-C (3.666 g, 56% purity, 12.78 mmol), (R)-1-phenylethylamine (1.72 mL, 13.46 mmol), and acetone cyanohydrine (3.5 mL, 38.25 mmol) in MeOH (11 mL) was refluxed in 75° C. bath. After 41.5 hours, the reaction mixture was diluted with CH₂Cl₂ and washed with aq. NaHCO₃ and water. After the aqueous fractions were extracted with CH₂Cl₂, the organic fractions were combined, dried (MgSO₄), and concentrated. The residue was purified by column chromatography on silica gel using hexane-ethyl acetate as eluents to obtain compounds 9-D and 9-D'.

$^1$H NMR (400 MHz, Chloroform-d) δ 7.34 (m, 4H), 7.28-7.19 (m, 1H), 4.10 (q, J=6.7 Hz, 1H), 2.80-2.62 (m, 1H), 2.37 (t, J=9.8 Hz, 1H), 2.28 (dd, J=21.2, 10.4 Hz, 2H), 1.78 (q, J=10.0, 7.9 Hz, 3H), 1.70-1.47 (m, J=5.8, 4.4 Hz, 4H), 1.46-1.29 (m, 2H), 0.96 (s, 3H).

LCMS-ESI⁺ (m/z): [M+H]⁺ calculated for C₁₇H₂₃N₂: 255.19; found: 254.9.

Step 4

A mixture of compound 9-D (229 mg, 0.900 mmol) and 20% Pd(OH)₂/C (118 mg) in EtOH (7 mL) and 4 N HCl in dioxane (0.9 mL) was stirred under H₂ atmosphere. After 3 hours, additional 20% Pd(OH)₂/C (55 mg) was added. After 2.5 hours, additional 20% Pd(OH)₂/C (61 mg) was added. After 2.5 hours, the reaction mixture was filtered and the filtrate was concentrated to provide compound 9-E.

$^1$H NMR (400 MHz, DMSO-d₆) δ 3.49 (d, J=14.0 Hz, 1H), 3.40 (d, J=14.0 Hz, 1H), 3.37-3.32 (m, 1H), 3.17-3.09 (m, 1H), 2.05-1.86 (m, 3H), 1.86-1.70 (m, 3H), 1.70-1.61 (m, 1H), 1.61-1.43 (m, 1H), 1.19 (s, 3H).

LCMS-ESI⁺ (m/z): [M+H]⁺ calculated for C₉H₁₉N₂: 155.15; found: 155.1.

Step 5

The mixture of compound 9-E, compound 1-E (314 mg, 0.907 mmol), and NaHCO₃ (305 mg, 3.631 mmol) in water (3 mL) and EtOH (3 mL) was stirred at room temperature. After 1 hour, the reaction mixture was concentrated to dryness and the residue was dissolved in CH₂Cl₂ before drying (MgSO₄). After the dried solution was concentrated, the residue was dissolved in CH₂Cl₂ (1.5 mL) and 4 N HCl in dioxane (4.5 mL). After stirred at room temperature for 20 min, the solution was concentrated to dryness and co-evaporated with toluene.

A suspension of the residue and DBU (0.7 mL, 4.681 mmol) in toluene (7 mL) was stirred at 100° C. bath for 20 min. After the mixture was concentrated, the residue was purified by column chromatography on silica gel using ethyl acetate-20% MeOH/ethyl acetate as eluents to obtain compound 9-F $^1$H NMR (400 MHz, Chloroform-d) δ 8.21 (s, 1H), 7.64 (dd, J=7.2, 1.4 Hz, 2H), 7.36-7.22 (m, 3H), 5.49 (d, J=9.9 Hz, 1H), 5.17 (d, J=9.9 Hz, 1H), 4.39 (q, J=7.1 Hz, 2H), 4.15-4.06 (m, 1H), 4.01 (d, J=12.7 Hz, 1H), 3.48-3.33 (m, 2H), 1.67 (s, 3H), 1.65-1.48 (m, 2H), 1.39 (t, J=7.1 Hz, 3H), 1.48-1.30 (m, 3H), 1.17 (s, 3H).

LCMS-ESI⁺ (m/z): [M+H]⁺ calculated for C₂₅H₂₉N₂O₅: 437.21; found: 437.3.

Step 6

A mixture of compound 9-F (243 mg, 0.557 mmol) in THF (2 mL) and EtOH (2 mL) was stirred at room temperature as 1 N KOH (1.15 mL) was added. After 30 min, the reaction mixture was diluted with water and acidified with 1 N HCl (1.5 mL), the product was extracted with CH₂Cl₂ (×2). The combined extracts were dried (MgSO₄), concentrated, and dried under vacuum to obtain compound 9-G.

LCMS-ESI⁺ (m/z): [M+H]⁺ calculated for C₂₃H₂₅N₂O₅: 409.18; found: 409.2.

Step 7

A mixture of compound 9-G (188 mg, 0.460 mmol), 2,4,6-trifluorobenzylamine (99 mg, 0.614 mmol), and HATU (270 mg, 0.710 mmol) in CH₂Cl₂ (5 mL) was stirred at room temperature as DIPEA (0.595 mL, 3.414 mmol) was added. After 30 min, the reaction mixture was diluted with ethyl acetate, and washed with saturated NH$_4$Cl (×2), water), saturated NaHCO$_3$ (×2), and brine. After the aqueous fractions were extracted with ethyl acetate, the two organic fractions were combined, dried (MgSO$_4$) and concentrated. The residue was purified by column chromatography on silica gel using ethyl acetate-20% MeOH/ethyl acetate as eluents to obtain compound 9-H.

$^1$H NMR (400 MHz, Chloroform-d) δ 10.48-10.31 (m, 1H), 8.36 (s, 1H), 7.57 (dt, J=6.1, 1.5 Hz, 2H), 7.37-7.21 (m, 3H), 6.74-6.57 (m, 2H), 5.40 (d, J=10.0 Hz, 1H), 5.18 (d, J=10.0 Hz, 1H), 4.69 (dd, J=14.5, 5.7 Hz, 1H), 4.61 (dd, J=14.5, 5.5 Hz, 1H), 4.04 (s, 2H), 3.43 (d, J=12.2 Hz, 1H), 3.36 (d, J=12.2 Hz, 1H), 1.73-1.52 (m, 4H), 1.52-1.27 (m, 4H), 1.17 (s, 3H).

$^{19}$F NMR (377 MHz, Chloroform-d) δ −72.06 (s 1F), −109.08, −111.85 (s, 2F).

LCMS-ESI$^+$ (m/z): [M+H]$^+$ calculated for C$_{30}$H$_{29}$F$_3$N$_3$O$_4$: 552.21; found: 552.3.

Step 8

Compound 9-H (200 mg, 0.363 mmol) was dissolved in TFA (2 mL) and stirred at room temperature. After 30 min, the solution was concentrated and the residue was dissolved in CH$_2$Cl$_2$ before washing with 0.1 N HCl. After the aqueous fraction was extracted with CH$_2$Cl$_2$ (×2), the organic fractions were combined, dried (MgSO$_4$), and concentrated. The residue was purified by column chromatography on silica gel using CH$_2$Cl$_2$-20% MeOH in CH$_2$Cl$_2$ as eluents to obtain compound 9.

$^1$H NMR (400 MHz, Chloroform-d) δ 10.42 (s, 1H), 8.62-7.93 (m, 1H), 6.76-6.53 (m, 2H), 4.71-4.56 (m, 2H), 4.24-3.94 (m, 2H), 3.61 (d, J=12.3 Hz, 1H), 3.35-3.20 (d, J=12.3 Hz, 1H), 1.87-1.71 (m, 4H), 1.66 (d, J=8.7 Hz, 1H), 1.58-1.36 (m, 3H), 1.22 (s, 3H).

$^{19}$F NMR (377 MHz, Chloroform-d) δ −108.11-−110.11 (s, 1F), −111.95 (s, 2F).

LCMS-ESI$^+$ (m/z): [M+H]$^+$ calculated for C$_{23}$H$_{23}$F$_3$N$_3$O$_4$: 462.16; found: 462.3.

Example 10

Preparation of Compound 10

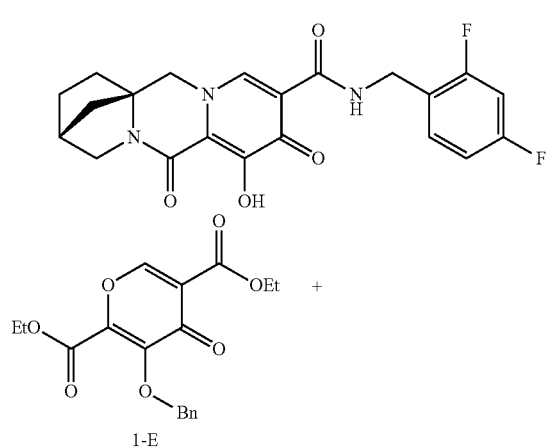

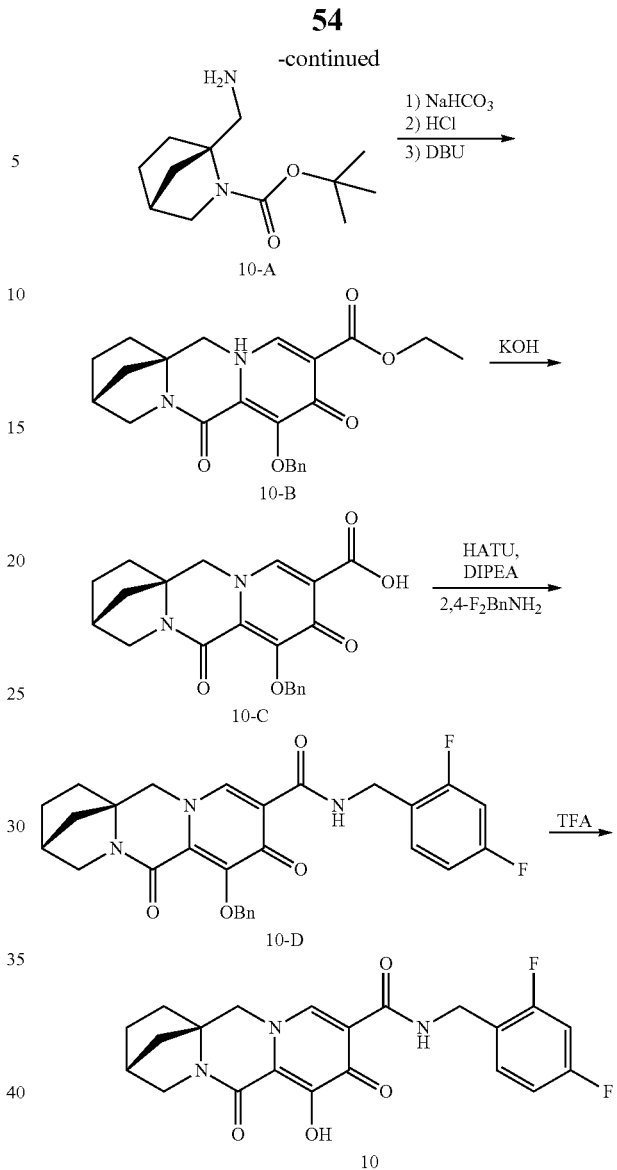

Step 1

A mixture of compound 1-E (300 mg, 0.876 mmol), compound 10-A (*Tetrahedron: Asymmetry* 2006, 17, 252-258; 220 mg, 0.837 mmol), and NaHCO$_3$ (156 mg, 1.857 mmol) in water (3 mL) and EtOH (3 mL) was stirred at room temperature. After 2 hours, the reaction mixture was diluted with water and extracted with ethyl acetate. After the extracts were washed with water, the organic fractions were combined, dried (Na$_2$SO$_4$), and concentrated. The residue was dried under vacuum and used for the next reaction.

To a solution of the above residue in CH$_2$Cl$_2$ (2 mL) was added 4 N HCl in dioxane (4 mL) at room temperature. After 1.5 hours, the solution was concentrated and dried in vacuum for 1 hour. A suspension of the residue and DBU (0.55 mL, 3.678 mmol) in toluene (5 mL) was stirred at 110° C. bath for 30 min. After the mixture was concentrated, the residue was purified by column chromatography on silica gel using ethyl acetate-20% MeOH/ethyl acetate as eluent to obtain compound 10-B.

LCMS-ESI$^+$ (m/z): [M+H]$^+$ calculated for C$_{23}$H$_{25}$N$_2$O$_5$: 409.18; found 409.4.

Step 2 and Step 3

A solution of compound 10-B (200 mg, 0.49 mmol) in THF (2 mL) and MeOH (2 mL) was stirred at room temperature as 1N KOH (0.35 mL) was added. After 2.25 hours, the reaction mixture was concentrated, acidified with 1 N HCl (~0.4 mL), and diluted with brine before extraction with CH$_2$Cl$_2$. The combined extracts were dried (Na$_2$SO$_4$) and concentrated. The resulting crude 10-C was used for the next reaction directly.

A mixture of the crude 10-C, 2,4-difluorobenzylamine (40 mg, 0.355 mmol), and HATU (93 mg, 0.245 mmol) in CH$_2$Cl$_2$ (3 mL) was stirred at room temperature as DIPEA (0.20 mL, 1.148 mmol) was added. After ~30 min, the reaction mixture was diluted with ethyl acetate, and washed with saturated NH$_4$Cl, water, saturated NaHCO$_3$, and brine. After the aq. fractions were extracted with ethyl acetate, the organic fractions were combined, dried (Na$_2$SO$_4$) and concentrated. The resulting residue was purified by column chromatography on silica gel using ethyl acetate-20% MeOH/ethyl acetate as eluent to obtain compound 10-D:

$^1$H NMR (400 MHz, Chloroform-d) δ 8.40 (s, 1H), 7.60 (d, J=7.4 Hz, 2H), 7.45-7.36 (m, 1H), 7.36-7.27 (m, 3H), 6.90-6.73 (m, 2H), 5.38 (d, J=9.9 Hz, 1H), 5.20 (d, J=9.9 Hz, 1H), 4.74-4.56 (m, 2H), 4.49 (d, J=12.9 Hz, 1H), 4.23 (d, J=12.9 Hz, 1H), 3.61 (dt, J=11.4, 3.0 Hz, 1H), 3.45 (d, J=11.2 Hz, 1H), 2.74 (s, 1H), 1.92 (dd, J=16.5, 7.4 Hz, 2H), 1.71 (d, J=9.7 Hz, 1H), 1.67-1.57 (m, 1H), 1.57-1.46 (m, 2H), 1.36-1.12 (m, 3H), 0.94-0.63 (m, 1H).

LCMS-ESI$^+$ (m/z): [M+H]$^+$ calculated for C$_{28}$H$_{26}$F$_2$N$_3$O$_4$: 506.19; found 506.6.

Step 4

Compound 10-D (90 mg, 0.146 mmol) was dissolved in TFA (1 mL) and stirred at room temperature. After 30 min, the solution was concentrated and the residue was purified by column chromatography on silica gel using CH$_2$Cl$_2$-20% MeOH in CH$_2$Cl$_2$ as eluents to obtain compound 10 (3R, 12aS)-N-(2,4-difluorobenzyl)-7-hydroxy-6,8-dioxo-2,3,4,6,8,12-hexahydro-1H-3,12a-methanodipyrido[1,2-a:1',2'-d]pyrazine-9-carboxamide:

$^1$H NMR (400 MHz, Acetonitrile-d3) δ 12.75 (s, 1H), 10.46 (s, 1H), 8.37 (s, 1H), 7.46-7.40 (m, 1H), 7.00-6.93 (m, 2H), 4.60-4.56 (m, 2H), 4.53-4.40 (m, 2H), 3.51-3.43 (m, 2H), 2.72 (s, 1H), 1.86-1.71 (m, 3H), 1.61-1.53 (m, 2H).

LCMS-ESI$^+$ (m/z): [M+H]$^+$ calculated for C$_{21}$H$_{20}$F$_2$N$_3$O$_4$: 416.14; found 416.3.

Example 11

Preparation of Compound 11

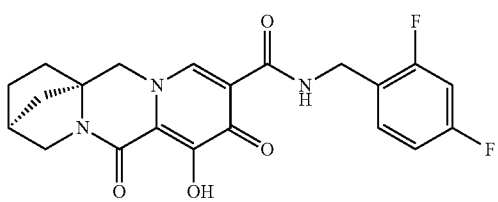

11

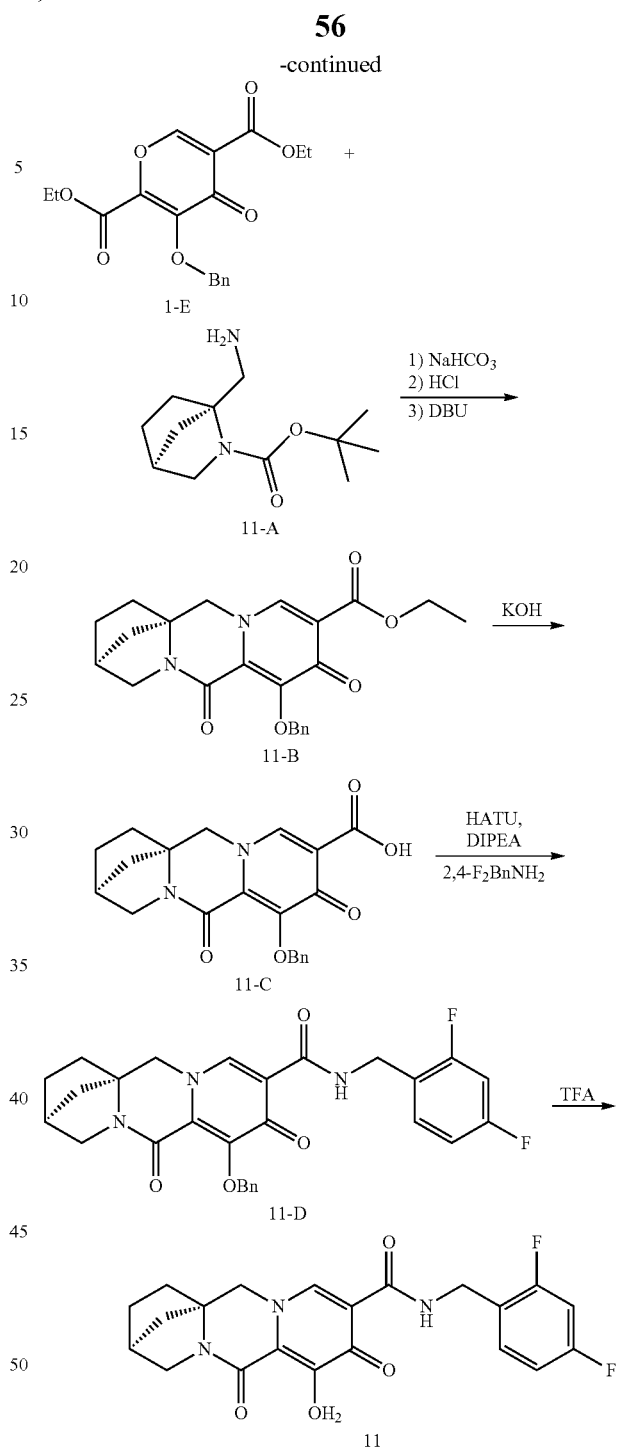

Compound 11 was synthesized as described above for compound 10, using (220 mg, 0.837 mmol) of compound 11-A (Tetrahedron: Asymmetry 2006, 17, 252-258) in place of compound 10-A.

$^1$H NMR (400 MHz, acetonitrile-d3) δ 12.75 (s, 1H), 10.46 (s, 1H), 8.37 (s, 1H), 7.42 (m, 1H), 6.99-6.93 (m, 2H), 4.59 (d, J=6.0 Hz, 2H), 4.47 (q, J=12.8 Hz, 2H), 3.55-3.42 (m, 2H), 2.75 (s, 1H), 1.93 (m, 2H), 1.82-1.79 (m, 3H), 1.60-1.53 (m, 2H).

LCMS-ESI$^+$ (m/z): [M+H]$^+$ calculated for C$_{21}$H$_{20}$F$_2$N$_3$O$_4$: 416.14; found 416.3.

Example 12

Preparation of Compound 12

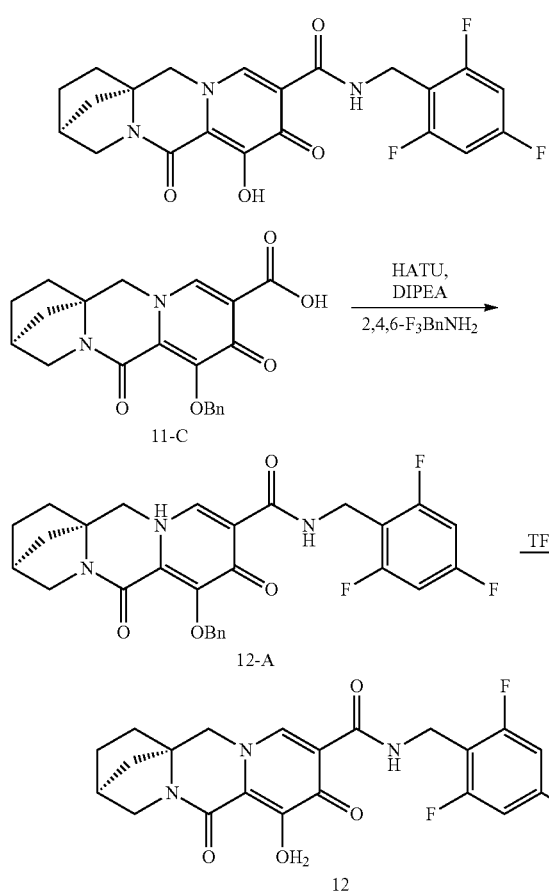

Step 1

To compound 11-C (0.0850 g, 0.223 mmol) and 2,4,6-trifluorobenzylamine (0.0701 g, 0.435 mmol, 2 equiv.) in CH$_2$Cl$_2$ (5 mL) was added DIPEA (0.28 mL, 1.56 mmol, 7 equiv.) and HATU (0.1277 g, 0.335 mmol, 1.5 equiv.). After 60 minutes, the reaction was diluted with CH$_2$Cl$_2$ (10 mL), and washed with sat. NH$_4$Cl (10 mL) and water (10 mL). The combined aqueous layers were extracted with CH$_2$Cl$_2$ (2×20 mL). The combined organics were dried over Na$_2$SO$_4$, concentrated in vacuo and purified by column chromatography on silica gel (0-10% MeOH:EtOAc) to obtain compound 12-A.

$^1$H NMR (400 MHz, DMSO-d$_6$) δ –10.45 (t, J=5.8 Hz, 1H), 8.53 (s, 1H), 8.18 (s, OH), 7.63-7.45 (m, 2H), 7.39-7.27 (m, 3H), 7.21 (dd, J=9.2, 8.1 Hz, 2H), 5.12 (d, J=10.3 Hz, 1H), 5.01 (d, J=10.3 Hz, 1H), 4.79 (d, J=13.2 Hz, 1H), 4.57 (dd, J=8.7, 3.7 Hz, 2H), 3.62 (pd, J=6.6, 3.9 Hz, 1H), 3.29-3.22 (m, 1H), 3.14 (qd, J=7.3, 4.2 Hz, 1H), 2.63 (s, 1H), 1.83 (d, J=9.3 Hz, 2H), 1.71-1.58 (m, 2H), 1.43 (q, J=11.1 Hz, 2H).

$^{19}$F NMR (376 MHz, DMSO-d$_6$) δ –109.28 (tt, J=9.3, 6.4 Hz), –112.37 (t, J=7.2 Hz).

LCMS-ESI$^+$ (m/z): [M+H]$^+$ calculated for C$_{28}$H$_{25}$F$_3$N$_3$O$_4$: 524.18; found: 524.14.

Step 2

To compound 12-A (0.117 g, 0.223 mmol) was added trifluoroacetic acid (5 mL). After 40 minutes, the mixture was concentrated in vacuo. Trituration with Et$_2$O provided compound 12.

$^1$H NMR (400 MHz, DMSO-d$_6$) δ 12.58 (s, 1H), 10.42 (t, J=5.8 Hz, 1H), 8.43 (s, 1H), 7.20 (t, J=8.6 Hz, 2H), 4.81 (d, J=13.2 Hz, 1H), 4.57-4.47 (m, 3H), 3.44 (m, 2H), 2.69 (m, 1H), 1.89 (m, 2H), 1.72 (m, 3H), 1.51 (m, 1H), 1.25 (m, 2H).

$^{19}$F NMR (376 MHz, DMSO-d$_6$) δ –109.35 (ddd, J=15.4, 9.3, 6.3 Hz), –112.48 (t, J=7.3 Hz).

LCMS-ESI$^+$ (m/z): [M+H]$^+$ calculated for C$_{21}$H$_{19}$F$_3$N$_3$O$_4$: 434.13; found: 434.28.

Example 13

Preparation of Compound 13

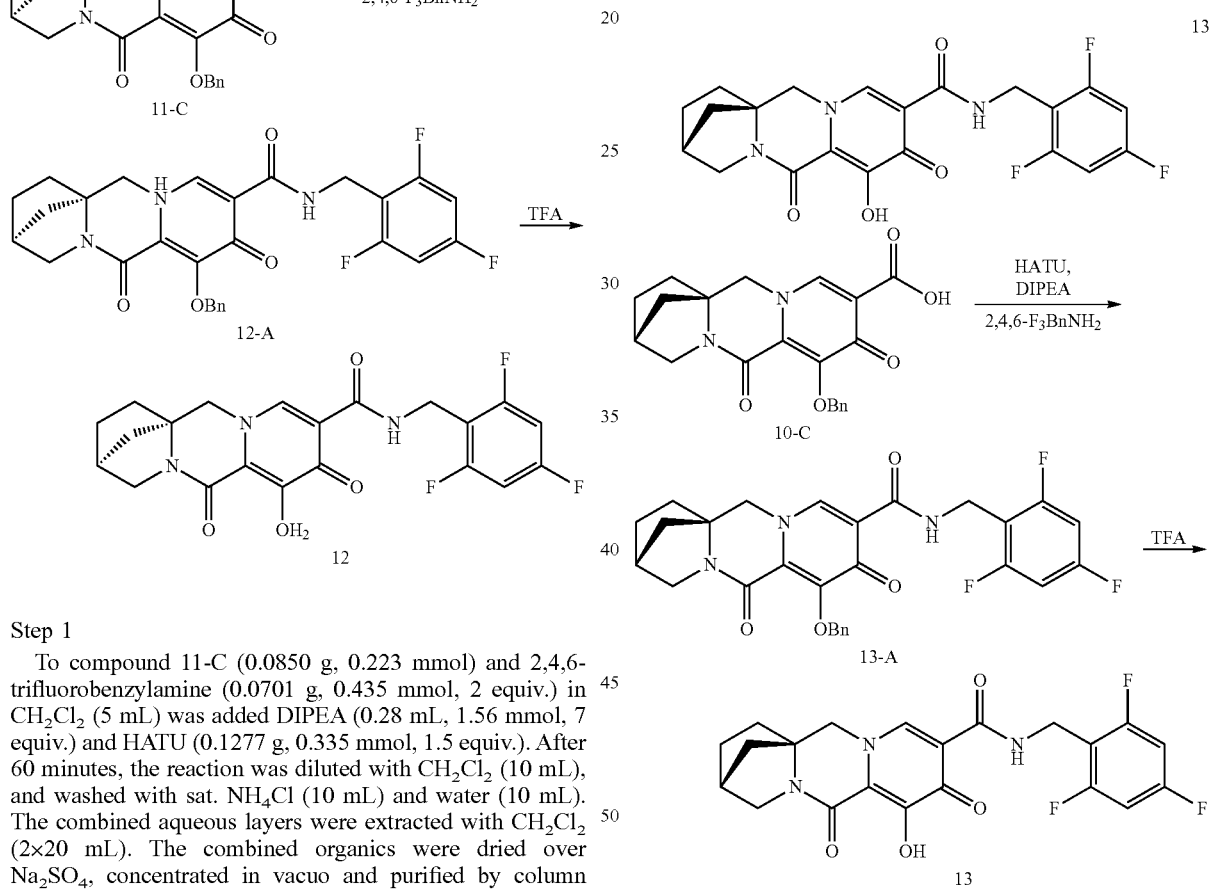

Compound 13 is synthesized as described above for compound 10, except 2,4,6-difluorobenzyl amine (0.0701 g, 0.435 mmol, 2 equiv.) was used in Step 3 rather than 2,4-difluorobenzyl amine.

Step 1

To 10-C (0.0601 g, 0.158 mmol) and 2,4,6-trifluorobenzylamine (0.0463 g, 0.287 mmol, 1.8 equiv.) in CH$_2$Cl$_2$ (5 mL) was added DIPEA (0.20 mL, 1.10 mmol, 7 equiv.) and HATU (0.0953 g, 0.237 mmol, 1.5 equiv.). After 60 minutes, the reaction was diluted with CH$_2$Cl$_2$ (10 mL), and washed with sat. NH$_4$Cl (10 mL) and water (10 mL). The combined aqueous layers were extracted with CH$_2$Cl$_2$ (2×20 mL). The combined organics were dried over Na$_2$SO$_4$ and concentrated in vacuo. Purification by column chromatography on silica gel (0-10% MeOH:EtOAc) afforded 13-A (0.1064 g, 97%). $^1$H NMR (400 MHz, DMSO-d$_6$) δ 10.45 (t, J=5.8 Hz, 1H), 8.53 (s, 1H), 7.61-7.45 (m, 2H), 7.38-7.27 (m, 3H), 7.27-7.16 (m, 2H), 5.12 (d, J=10.3 Hz, 1H), 5.01 (d, J=10.3 Hz, 1H), 4.79 (d, J=13.2 Hz, 1H), 4.62-4.50 (m, 3H), 3.62 (pd, J=6.5, 3.8 Hz, 1H), 3.26 (d, J=10.9 Hz, 1H), 3.14 (qd, J=7.3, 4.2 Hz, 1H), 1.83 (d, J=9.3 Hz, 2H), 1.71-1.59 (m, 2H), 1.42 (p, J=10.1, 9.4 Hz, 2H). $^{19}$F NMR (376 MHz, DMSO-d$_6$) δ −109.21−−109.34 (m), −112.38 (t, J=7.3 Hz). LCMS-ESI$^+$ (m/z): [M+H]$^+$ calculated for C$_{28}$H$_{25}$F$_3$N$_3$O$_4$: 524.18; found: 524.28.

Step 2

To 13-A (0.083 g, 0.159 mmol) was added trifluoroacetic acid (5 mL). After 45 minutes, the mixture was concentrated in vacuo. Trituration with Et$_2$O afforded 13.

$^1$H NMR (400 MHz, DMSO-d$_6$) δ 12.57 (s, 1H), 10.42 (t, J=5.8 Hz, 1H), 8.43 (s, 1H), 7.20 (t, J=8.6 Hz, 2H), 4.81 (d, J=13.2 Hz, 1H), 4.55 (d, J=5.8 Hz, 2H), 4.51 (d, J=13.0 Hz, 1H), 3.50-3.40 (m, 2H), 2.68 (m, 1H), 1.89 (m, 2H), 1.73 (m, 3H), 1.55-1.42 (m, 1H), 1.25 (m, 2H).

$^{19}$F NMR (376 MHz, DMSO-d$_6$) δ −109.36 (ddd, J=15.5, 9.6, 6.4 Hz), −112.49 (t, J=7.3 Hz).

LCMS-ESI$^+$ (m/z): [M+H]$^+$ calculated for C$_{21}$H$_{19}$F$_3$N$_3$O$_4$: 434.13; found: 434.21.

Example 14

Preparation of Compound 14

Step 1

A mixture of compound 3-G (75 mg, 0.184 mmol) in THF (1.25 mL) and MeOH (1.25 mL) was stirred at room temperature as 1 N KOH (0.97 mL) was added. After 30 minutes at room temperature, the reaction mixture was concentrated and diluted with water before washing with ether (×1). The aqueous fraction was acidified with 1 N HCl (~3.3 mL), and extracted with ethyl acetate (×2). The extracts were washed with brine (×1), combined, dried (Na$_2$SO$_4$), and concentrated to provide the crude acid.

LCMS-ESI$^+$ (m/z): [M+H]$^+$ calculated for C$_{21}$H$_{21}$N$_2$O$_5$: 381.15; found: 381.09.

A mixture of the crude acid from the previous step (64 mg, 0.168 mmol), (R)-1-(2,4,6-trifluorophenyl)ethylamine (34 mg, 0.193 mmol), and HATU (83 mg, 0.219 mmol) in DMF (2 mL) was stirred at room temperature as DIPEA (0.21 mL, 1.178 mmol) was added. After 2 hours, the mixture was diluted with ethyl acetate, washed with saturated NH$_4$Cl and saturated NaHCO$_3$. After the aqueous fractions were extracted with ethyl acetate, the organic fractions were combined, dried (Na$_2$SO$_4$), and concentrated to provide compound 14-A.

LCMS-ESI$^+$ (m/z): [M+H]$^+$ calculated for C$_{29}$H$_{27}$F$_3$N$_3$O$_4$: 538.20; found: 538.06.

Step 2

Compound 14-A (85 mg, 0.158 mmol) was dissolved and stirred in TFA (1.2 mL) at room temperature. After 15 minutes, the solution was concentrated and the residue was purified by preparative HPLC and the collected fraction was freeze-dried to provide compound 14.

$^1$H NMR (400 MHz, Chloroform-d) δ 10.76 (d, J=8.1 Hz, 1H), 8.36 (s, 1H), 6.63 (t, J=8.4 Hz, 2H), 5.64 (p, J=7.4 Hz, 1H), 4.81 (t, J=4.8 Hz, 1H), 4.50-4.16 (m, 2H), 2.10-1.43 (m, 12H).

LCMS-ESI$^+$ (m/z): [M+H]$^+$ calculated for C$_{22}$H$_{21}$F$_3$N$_3$O$_4$: 448.15; found: 448.18.

Example 15

Preparation of Compound 15

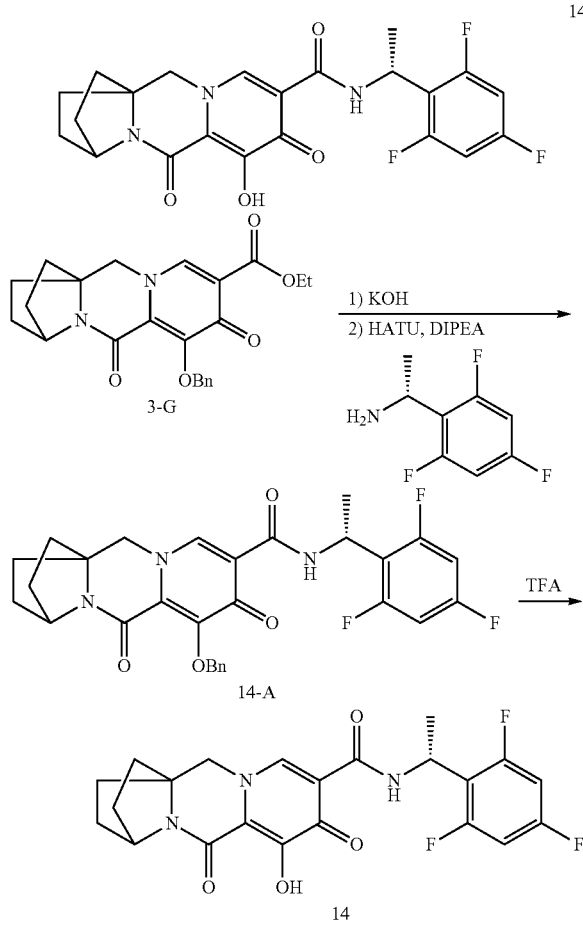

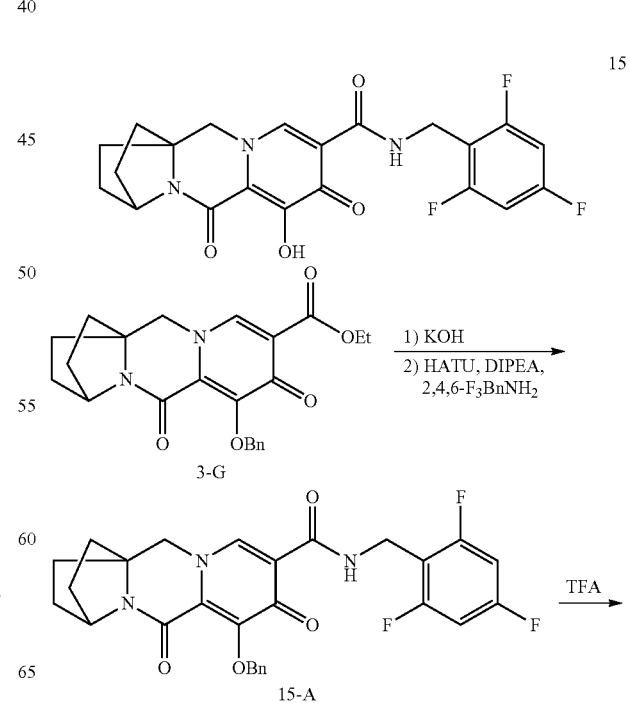

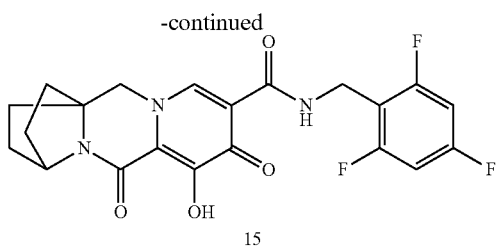

15

Step 1

A mixture of compound 3-G (165 mg, 0.404 mmol) in THF (2.5 mL) and MeOH (2.5 mL) was stirred at room temperature as 1 N KOH (2.13 mL) was added. After 30 minutes at room temperature, the reaction mixture was concentrated and diluted with water, acidified with 1 N HCl, and extracted with ethyl acetate (×2). The extracts were combined, dried (Na$_2$SO$_4$), and concentrated to provide the crude acid.

LCMS-ESI$^+$ (m/z): [M+H]$^+$ calculated for C$_{21}$H$_{21}$N$_2$O$_5$: 381.15; found: 381.13.

A mixture of the crude acid from the previous step (150 mg, 0.394 mmol), 2,4,6-trifluorobenzylamine (76 mg, 0.47 mmol), and HATU (188 mg, 0.49 mmol) in DMF (3 mL) was stirred at room temperature as DIPEA (0.48 mL, 2.76 mmol) was added. After 2 hours, additional 2,4,6-trifluorobenzylamine (32 mg, 0.20 mmol), HATU (105 mg, 0.28 mmol), and DIPEA (0.14 mL, 0.79 mmol) were added and the resulting mixture was stirred at room temperature. After 2 days, additional 2,4,6-trifluorobenzylamine (32 mg, 0.20 mmol), HATU (105 mg, 0.28 mmol), and DIPEA (0.14 mL, 0.79 mmol) were added and the resulting mixture was stirred at room temperature for 2 hours. The mixture was diluted with water, extracted with ethyl acetate (×3), and combined extracts were dried (Na$_2$SO$_4$), and concentrated to provide crude compound 15-A.

LCMS-ESI$^+$ (m/z): [M+H]$^+$ calculated for C$_{28}$H$_{25}$F$_3$N$_3$O$_4$: 524.18; found: 524.15.

Step 2

Compound 15-A (205 mg, 0.392 mmol) was dissolved and stirred in TFA (3 mL) at room temperature. After 15 minutes, the solution was concentrated and the residue was purified by preparative HPLC and the collected fraction was freeze-dried to provide compound 15.

$^1$H NMR (400 MHz, DMSO-d$_6$) δ 12.65 (s, 1H), 10.38 (t, J=5.8 Hz, 1H), 8.44 (s, 1H), 7.30-7.07 (m, 2H), 4.65 (m, 3H), 4.55 (d, J=5.7 Hz, 2H), 1.91-1.75 (m, 4H), 1.69 (dtt, J=21.9, 9.5, 3.9 Hz, 4H).

LCMS-ESI$^+$ (m/z): [M+H]$^+$ calculated for C$_{21}$H$_{19}$F$_3$N$_3$O$_4$: 434.13; found: 434.19.

Antiviral Assay

Example 16

Antiviral Assays in MT4 Cells

For the antiviral assay utilizing MT4 cells, 0.4 μL of 189× test concentration of 3-fold serially diluted compound in DMSO was added to 40 μL of cell growth medium (RPMI 1640, 10% FBS, 1% penicilline/Streptomycine, 1% L-Glutamine, 1% HEPES) in each well of 384-well assay plates (10 concentrations) in quadruplicate.

1 mL aliquots of 2×10$^6$ MT4 cells are pre-infected for 1 and 3 hours respectively at 37° C. with 25 μL (MT4) or of either cell growth medium (mock-infected) or a fresh 1:250 dilution of an HIV-IIb concentrated ABI stock (0.004 m.o.i. for MT4 cells). Infected and uninfected cells are diluted in cell growth medium and 35 μL of 2000 (for MT4) cells is added to each well of the assay plates.

Assay plates were then incubated in a 37° C. incubator. After 5 days of incubation, 25 μL of 2× concentrated CellTiter-Glo™ Reagent (catalog #G7573, Promega Biosciences, Inc., Madison, Wis.) was added to each well of the assay plate. Cell lysis was carried out by incubating at room temperature for 2-3 minutes, and then chemiluminescence was read using the Envision reader (PerkinElmer).

Compounds of the present invention demonstrate antiviral activity in this assay as depicted in Table 1 below. Accordingly, the compounds of the invention may be useful for treating the proliferation of the HIV virus, treating AIDS, or delaying the onset of AIDS or ARC symptoms.

TABLE 1

| Compound Number | nM in MT-4 | |
|---|---|---|
| | EC$_{50}$ | CC$_{50}$ |
| 1 | 3.5 | 49911 |
| 2 | 4.4 | 53192 |
| 3 | 1.9 | 26191 |
| 4 | 1.6 | 10963 |
| 5 | 1.3 | 10630 |
| 6 | 2.6 | 9659 |
| 7 | 2.8 | 12992 |
| 8 | 2.3 | 5303 |
| 9 | 1.4 | 8665 |
| 10 | 2.3 | 24021 |
| 11 | 3.2 | 27861 |
| 12 | 3.2 | 53192 |
| 13 | 1.7 | 24340 |
| 14 | 6.2 | 13196 |
| 15 | 2.3 | 24021 |

The data in Table 1 represent an average over time for each compound. For certain compounds, multiple assays have been conducted over the life of the project. Thus, the data reported in Table 1 include the data reported in the priority documents, as well as data from assays run in the intervening period.

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound having a Formula (I):

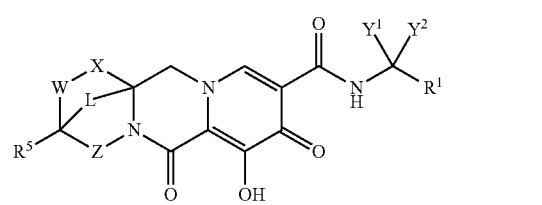

Formula (I)

or a pharmaceutically acceptable salt or stereoisomer thereof, wherein:

L is —C($R^a$)$_2$—;

each $R^a$ is independently hydrogen, halogen, hydroxy, or $C_{1-4}$alkyl;

W is a bond;

X is —CHR$^2$—;

R$^2$ is hydrogen or C$_{1-3}$alkyl;

Z is —CHR$^4$—;

R$^4$ is hydrogen or C$_{1-3}$alkyl;

R$^5$ is hydrogen, C$_{1-3}$ alkyl, or C$_{1-3}$haloalkyl;

Y$^2$ is hydrogen, C$_{1-3}$alkyl, or C$_{1-3}$haloalkyl;

Y$^2$ is hydrogen, C$_{1-3}$alkyl, or C$_{1-3}$haloalkyl; and

R$^1$ is phenyl, wherein the phenyl is substituted with one, two, or three independently selected halogen substituents.

2. The compound of claim 1, wherein the compound has Formula (IV):

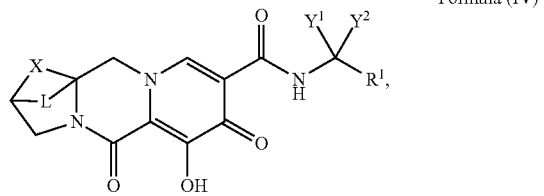

Formula (IV)

or a pharmaceutically acceptable salt or stereoisomer thereof.

3. The compound of claim 2, wherein the compound has Formula (IV—A):

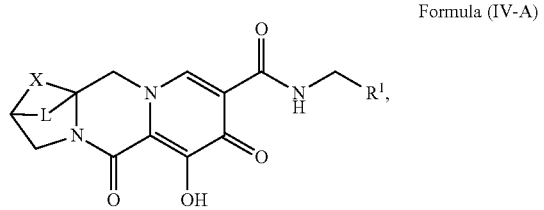

Formula (IV-A)

or a pharmaceutically acceptable salt or stereoisomer thereof.

4. The compound of claim 1, or a pharmaceutically acceptable salt or stereoisomer thereof, wherein each $R^a$ is independently hydrogen.

5. The compound of claim 1, or a pharmaceutically acceptable salt or stereoisomer thereof, wherein R$^5$ is hydrogen or C$_{1-3}$alkyl.

6. The compound of claim 1, or a pharmaceutically acceptable salt or stereoisomer thereof, wherein R$^5$ is hydrogen.

7. The compound of claim 1, or a pharmaceutically acceptable salt or stereoisomer thereof, wherein R$^5$ is CH$_3$.

8. The compound of claim 1, or a pharmaceutically acceptable salt or stereoisomer thereof, wherein R$^1$ is phenyl, wherein the phenyl is substituted with one halogen substituent.

9. The compound of claim 8, or a pharmaceutically acceptable salt or stereoisomer thereof, wherein R$^1$ is or 2 fluorophenyl or 4-fluorophenyl.

10. The compound of claim 1, or a pharmaceutically acceptable salt or stereoisomer thereof, wherein R$^1$ is phenyl, wherein the phenyl is substituted with two independently selected halogen substituents.

11. The compound of claim 10, or a pharmaceutically acceptable salt or stereoisomer thereof, wherein R$^1$ is 2,3-difluorophenyl, 2,4-difluorophenyl, 2,6-difluorophenyl, 3,4-difluorophenyl, 3,5-difluorophenyl, 3-chloro-2-fluorophenyl, 4-chloro-2-fluorophenyl, or 4-chloro-3-fluorophenyl.

12. The compound of claim 10, or a pharmaceutically acceptable salt or stereoisomer thereof, wherein R$^1$ is 2,3-difluorophenyl, 2,4-difluorophenyl, 2,6-difluorophenyl, 3,4-difluorophenyl, 3,5-difluorophenyl, 4-chloro-2-fluorophenyl, or 4-chloro-3-fluorophenyl.

13. The compound of claim 12, or a pharmaceutically acceptable salt or stereoisomer thereof, wherein R$^1$ is 2,4-difluorophenyl.

14. The compound of claim 1, or a pharmaceutically acceptable salt or stereoisomer thereof, wherein R$^1$ is phenyl, wherein the phenyl is substituted with three independently selected halogen substituents.

15. The compound of claim 14, or a pharmaceutically acceptable salt or stereoisomer thereof, wherein R$^1$ is 2,3,4-trifluorophenyl or 2,4,6-trifluorophenyl.

16. The compound of claim 15, or a pharmaceutically acceptable salt or stereoisomer thereof, wherein R$^1$ is 2,4,6-trifluorophenyl.

17. A pharmaceutical composition comprising a pharmaceutically acceptable carrier, diluent, or excipient and the compound of claim 1, or a pharmaceutically acceptable salt or stereoisomer thereof.

18. A method for modulating human immunodeficiency virus proliferation in a human, wherein the method comprises administering to the human in need thereof a therapeutically effective amount of the compound of claim 1, or a pharmaceutically acceptable salt or stereoisomer thereof.

19. The method of claim 18, wherein the human is at risk of having a human immunodeficiency virus infection or the human has a human immunodeficiency virus infection.

20. A method for modulating human immunodeficiency virus proliferation in a human, wherein the method comprises administering to the human in need thereof a therapeutically effective amount of the pharmaceutical composition of claim 17.

21. The method of claim 20, wherein the human is at risk of having a human immunodeficiency virus infection or the human has a human immunodeficiency virus infection.

22. A compound having the following formula:

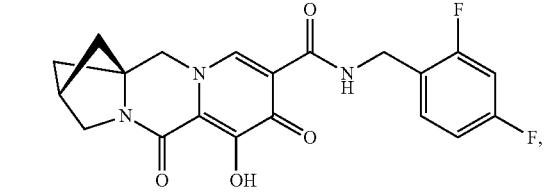 [SMILES: O=C(NCc1ccc(F)cc1F)c1cn2c(c(O)c1=O)C(=O)N1C[C@H]3C[C@]1(C2)C3]

or a pharmaceutically acceptable salt thereof.

* * * * *